United States Patent [19]
Gammill et al.

[11] Patent Number: 5,703,075
[45] Date of Patent: Dec. 30, 1997

[54] ANTIATHEROSCLEROTIC AND ANTITHROMBOTIC 1-BENZOPYRAN-4-ONES AND 2-AMINO-1,3-BENZOXAZINE-4-ONES

[75] Inventors: Ronald B. Gammill; Thomas M. Judge; Joel Morris, all of Kalamazoo, Mich.

[73] Assignee: Pharmacia & Upjohn Company, Kalamazoo, Mich.

[21] Appl. No.: 484,584

[22] Filed: Jun. 7, 1995

Related U.S. Application Data

[63] Continuation of Ser. No. 292,316, Aug. 19, 1994, abandoned, which is a continuation of Ser. No. 106,965, Aug. 16, 1993, abandoned, which is a continuation of Ser. No. 718,391, Jun. 19, 1991, abandoned, which is a continuation-in-part of Ser. No. 541,126, Jun. 20, 1990, abandoned, which is a continuation-in-part of Ser. No. 287,796, Dec. 21, 1988, abandoned.

[51] Int. Cl.$^6$ .............. A61K 31/535; A61K 31/54; C07D 413/04; C07D 413/14
[52] U.S. Cl. ............ 514/233.5; 514/228.2; 514/228.5; 514/235.2; 514/235.5; 514/235.8; 514/253; 514/320; 544/120; 544/121; 544/122; 544/124; 544/129; 544/141; 544/151; 544/376; 544/61; 544/90; 544/91; 544/92
[58] Field of Search ............ 544/120, 121, 544/122, 124, 129, 141, 151; 514/235.8, 235.5, 235.2, 233.5

[56] References Cited

U.S. PATENT DOCUMENTS

| | | | |
|---|---|---|---|
| 3,491,092 | 1/1970 | Grigat et al. | 544/73 |
| 4,092,416 | 5/1978 | Winter et al. | 514/253 |

FOREIGN PATENT DOCUMENTS

| | | | |
|---|---|---|---|
| B-73815/87 | 10/1987 | Australia | C07D 405/12 |
| A-32505/89 | 12/1989 | Australia | C07D 311/92 |
| 2205913 | 8/1973 | Germany | C07D 7/34 |
| 6412966 | 5/1965 | Netherlands | |
| 1389186 | 2/1973 | United Kingdom | C07D 311/22 |

OTHER PUBLICATIONS

Lee, K.T. "Atherosclerosis" Annals of N.Y. Academy of Science, v. 454, p. 42 (1985) * copy in parent case.
Derwent Abstract, Accession No. 79169A/44 (Japanese JA–025657) (1979).
Derwent Abstract, Accession No. 87–150605/21 (Japanese JP–259603) (1987).
Eaton, R. P., "High Density Lipoprotein—Key to Anti–Atherogenesis", J. Chron. Dis. 31:131–135 (1978).
Haust, M. D., "Reaction Patterns of Intimal Mesenchyme to Injury and Repair in Atherosclerosis", Adv. Exp. Med. Biol. 43:35–57 (1974).
Schurr, P. E., et al., "High Volume Screening Procedure for Hypobetalipoproteinemic Activity in Rats", Adv. Exp. Med. Biol. 67:215–229, Plasma Press (1975).

Day, C. E., et al., "Utility of a Selected Line (SEA) of the Japanese Quail (Coturnix Coturnix Japonica) for the Discovery of New Anti–Atherosclerosis Drugs", Lab. An. Sci. 27(5):817–821 (1977).
Mazzei, M., et al., "Ricerche Chimiche E Farmacologiche Su Derivati Piranici", Farmaco, Ed. Sci. 40:895–908 (1985).
Mazzei, M., et al., "Ricerche Chimiche E Farmacologiche Su Derivati Piranici", Farmaco. Ed. Sci. 41:611–621 (1986).
Balbi, A., et al., "Ricerche Chimiche E Farmacologiche Su Derivati Piranici", Farmaco. Ed. Sci. 37:582–596 (1982).
Ermili, A., et al., "Ricerche Chimiche E Farmacologiche Su Derivati Piranici", Farmaco. Ed. Sci. 32:375–387 (1977).
Ermili, A., et al., "Ricerche Chimiche E Farmacologiche Su Derivati Piranici", Farmaco. Ed. Sci. 32:713–724 (1977).
Balbi, A., et al., "Nitroderivati Di 2–(Dialchilammino)Cromoni", Farmaco. Ed. Sci. 38:784–793 (1983).
Balbi, A., et al., "Nitroderivati Di 2–(Dialchilammino)Cromoni", Farmaco. Ed. Sci. 41(7):548–547 (1986).
Mouysset, G., et al., "Pharmacomodulation d'adreénolytiques α en série benzopyrqnnique", Eur. J. Med. Chem. 22(6):539–544 (1987).
Eiden, F., et al., "Über die Reaktion von 3–Hydroxychromon mit Aminen", Arch. Pharm. (Weinheim Ger.) 308:385–388 (1975).
Ali, S. A., et al., "The Chemistry of Fungi. Part LXVII. Synthesis of Di–O–methyleitromycinone and Related Pyrano[3,2–c]benzopyran–4,5–diones", J. Chem. Soc. Perkin Trans. I:173–174 (1973).
Eiden, F. and G. Rademacher, "Synthese und Reaktionen von 3–Acyl–2–methylthio–chromonen", Arch. Pharm. (Weinheim Ger.) 316:34–42 (1983).
Bantick, J. R. and J. L. Suschitzky, "Synthesis of 2–Aminochromones. Studies on the Nucleophilic Displacement of Sulphinyl and Sulphonyl Groups in the 2–Position of 5,8–Dimethoxychromone", J. Heterocyclic Chem. 18:679–684 (1981).
Mazzei, M., et al., "Synthesis and Anti–Platelet Activity of Some 2–(Dialkylamino)Chromones", Eur. J. Med. Chem. 23:237–242 (1988).

(List continued on next page.)

*Primary Examiner*—Ceila Chang
*Attorney, Agent, or Firm*—William G. Jameson

[57] ABSTRACT

This invention relates to compounds of Formula I

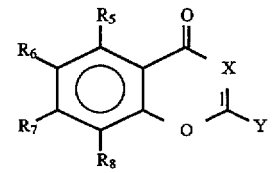

which are useful in association with a pharmaceutical carrier as antiatherosclerotic agents. In addition, various compounds of Formula I are useful inhibitors of cell proliferation.

12 Claims, No Drawings

OTHER PUBLICATIONS

Tronchet, J. M. J., et al., "Enaminosucres et sucres halogénoacétyléniques", Helv. Chim. Acta 59:941–944 (1976).

Grigat, E., et qal., "4H–1.3–Benzoxazinon–Derivate aus aromatischen Cyansäureestern mit einer ortho–ständigen carbonsäurefunktion", Chem. Ber. 97:3036–3044 (1964).

Jpn. Tokkyo Koho 79 20,504, "Oxazine and Thiazine Derivatives", CA 91:157755b, p. 644, (1979).

Jpn. Kokai 72 17,781, "Oxazine or Thiazine Derivatives", CA 77:140107e, p. 454 (1972).

Kokel, B., et al., "A New 'One Pot' Preparation of 2–N, N–Dialkylamino–1,3–Benzoxazines and Naphth[1,2–e][1, 3]Oxazines from Corresponding Ortho Hydroxynitriles and Phosgeniminium Salts", Tet. Letters, 25(35):3837–3840 (1984).

Palazzo, S. and L. I. Giannola, "Reazione Della 2H–1, 3–Benzossazina–2–Tione–4(3H)–One Con Ammine Primarie", Atti. Acad. Sci. Lett., Parte 1. 34(2):83–87 (1976).

Brunetti, H. and C. E. Lothi, "Die Synthese von Asymmetrisch Substituierten o–Hydroxyphenyl–s–triazinen", Helv. Chim. Acta, 55:1566–1595 (1972).

ANTIATHEROSCLEROTIC AND ANTITHROMBOTIC 1-BENZOPYRAN-4-ONES AND 2-AMINO-1,3-BENZOXAZINE-4-ONES

This application is a continuation of U.S. Ser. No. 08/292,316, filed Aug. 19, 1994; which is a continuation of U.S. Ser. No. 08/106,965, filed Aug. 16, 1993; which is a continuation of U.S. Ser. No. 08/718,391, filed Jun. 19, 1991, now abandoned; which is a continuation-in-part of PCT application No. PCT/US91/04140, fled Jun. 18, 1991; which is a continuation-in-part of U.S. Ser. No. 07/541326, filed Jun. 20, 1990, now abandoned, which is a continuation-in-part of Application No. PCT/US89/05526, filed Dec. 15, 1989; which is a continuation-in-part of U.S. Ser. No. 07/287,796, filed Dec. 21, 1988, now abandoned.

BACKGROUND OF THE INVENTION

The present specification provides methods for use of pharmacologically active substances. Further the present specification provides novel compositions of matter and novel methods of their preparation.

Atherosclerosis in mammals is a disease characterized by the deposition of atherosclerotic plaque on arterial walls. While atherosclerosis exhibits many varied forms and consequences, typical consequences of atherosclerotic diseases include angina pectoris, myocardial infarction, stroke and transient cerebral ischemic attacks. Other forms of atherosclerotic diseases include certain peripheral vascular diseases and other ischemias (e.g., bowel and renal).

Medical science now recognizes that certain forms of atherosclerosis may be preventable or reversible. Agents capable of preventing or reversing atherosclerosis are characterized as exhibiting antiatherosclerotic activity. Since serum lipids have a recognized association with atherogenesis, an important class of antiatherosclerotic agents are those with serum lipid-modifying effects. Serum lipids implicated in atherogenesis include serum cholesterol, serum triglycerides, and serum lipoproteins.

With respect to serum lipoproteins, at least three different classes of these substances have been characterized; high density lipoproteins (HDL's), low density lipoproteins (LDL's), and very low density lipoproteins (VLDL's). HDL's are often referred to as alphalipoproteins, while LDL's and VLDL's are referred to as betalipoproteins. The enhancement of HDL levels (hyperalphalipoproteinemic activity) is postulated to have direct antiatherosclerotic effects. See Eaton, R. P., J. Chron. Dis 31:131–135 (1978). In contrast, agents which reduce serum LDL's and serum VLDL's (hypobetalipoproteinemic agents) are also associated with antiatherogenic effects. See Haust, M. D., "Reaction Patterns of Intimal Mesenchyme to Injury and Repair in Atherosclerosis", Adv. Exp. Med. Biol. 43:35–57 (1974), which postulates that serum LDL is a factor in atherosclerotic lesion formation.

Numerous animal models have been developed for assessing antiatherosclerotic activity. Principal among these are models for assessing hypolipoproteinemic activity in the rat and antiatherosclerotic activity in the Japanese quail. For a description of the operation of the hypobetalipoproteinemic rat model, refer to the known methods of Schurr, P. E., et al., "High Volume Screening Procedure for Lypobetalipoproteinemia Activity in Rats", Adv. Exp. Med. Biol. 67: Atherosclerotic Drug Discovery, pp. 215–229, Plenum Press (1975). For a description of the Japanese quail model, see Day, C. E. et al., "Utility of a Selected Line (SEA) of the Japanese Quail (Corturnic Corturnix japonica) for the Discovery of New Anti-Atherosclerosis Drugs", Laboratory Animal Science 27:817–821 (1977).

2-Aminochromones (4H-1-benzopyran-4-ones) are known in the literature. For example, the antiallergic activity of 2-aminochromones has been described in the literature by Mazzei, Balbi, Ermili, Sottofattori and Roma (Mazzei, M., Ballbi, A., Ernili, A., Sottofattori, E., Roma, G., Farmaco. Ed. Sci., (1985) 40, 895 and Mazzei, M., Ermili, A., Balbi, A., Di Braccio, M., Farmaco. Ed. Sci., (1986), 41, 611; CA 106:18313w). The CNS activity of 2-aminochromones has also been described (Balbi, A., Roma, G., Ermili, A., Farmaco. Ed. Sci., (1982) 37, 582; Ermili, A., Mazzei, M., Roma, G., Cacciatore, C., Farmaco. Ed. Sci., (1977), 32, 375 and 713). The nitro derivatives of various 2-aminochromones have recently been described (Balbi, A., Roma, G., Mazzei, M., Ermili, A., Farmaco. Ed. Sci., (1983) 38, 784) and Farmaco. Ed. Sci., 41(7), 548–57. 2-Amino-3-hydroxychromones are described in DE 2205913 and GB 1389186.

U.S. Pat. No. 4,092,416 (see also DE 2555290 and CA 87:102383r) discloses various benzopyrone derivatives exhibiting anti-allergic activity, including 2-{2-[4-(2-methoxyphenyl)-piperazinyl-1]-ethyl}-5-methoxy-4-oxo-4H-1-benzopyran and 2-{2-[4-(2-methoxyphenyl)-piperazinyl-1]-ethyl}-5-(2-hydroxypropoxy)-4-oxo-4H-1-benzopyran.

JA-025657 and JP-259603 descrive various 2-amino-3-carboxamide derivatives and 3-phenyl (optionally substituted)-2-aminochromone derivatives as useful as oncostatic and immunosuppressive agents.

The pharmacomodulation of α-adrenergic blocking agents by a series of benzopyrans, including 2-(1-piperidinylmethylene) -4H-1-benzopyran-4-one, is described in Eur. J. Med. Chem., 1987, 22(6), 539–44; CA 109:92718k.

Structurally, the closest compounds in the literature to 2-(4-morpholinyl)-4H-1-benzopyran-4-one (Cpd 2) is believed to be the 3-hydroxy, 3-methoxy and 3-acetyloxy analogues (i.e., 2-(4-morpholinyl)-3-hydroxychromone, 2-(4-morpholinyl) -3-methoxychromone and 3-(acetyloxy)-2-(4-morpholinyl)chromone) reported by Eiden and Docher (Eiden, F., Dolcher, D., Arch. Pharm. (Weinheim Ger.) (1975) 308, 385) and DE 2205913; CA 83(11):96942w and CA79(19):1154408. 6,7-dimethoxy-2-(4-morpholinyl) chromone is disclosed in J. Chem. Soc., Perkins Trans. 1, (2), 173–4; CA78(9);58275v. 3-Acetyl-2-(4-morpholinyl) chromone is disclosed in Arch. Pharm. 316(1), 34–42; CA98(15):12915 g. 3-hydroxy-2-[4-(2-hydroxyethyl)-1-piperazinyl]-4H-1-benzopyran-4-one and 3-hydroxy-2-(4-methyl -1-piperazinyl)-4H-1-benzopyran-4-one are disclosed in Arch. Pharm 308(5), 385–8; CA83(11):96942w. 5,8-dimethoxy-2-(4-methyl -1-piperazinyl)-4H-1-benzopyran-4-one is disclosed in J. Heterocycl. Chem., 18(4), 679–84; CA95(17):150348v.

The synthesis of 2-aminochromones from the corresponding 2-sulphonyl and 2-sulphinyl analogues has been reported by Bantick and Suschitzky (Bantick, J. R., Suschitzky, J. L., J. Heterocyclic Chem., (1981) 18, 679). Also described in this report is the preparation of the HCL and $H_2SO_4$ salts of several 2-aminochromones.

The anti-platelet activity of some 2-(dialkylamino) chromones, namely: 2-(diethylamino)-5,6-dimethyl-4H-1-benzopyran-4-one,2-(diethylamino)-6,7-dimethyl-4H-1-benzopyran-4-one,2-(diethylamino)-7-hydroxy-5-methyl-4H-1-benzopyran-4-one, 2-(diethylamino)-5-hydroxy-7- methyl-4H-1-benzopyran-4-one, 2-(diethylamino)-6-chloro-8-isopropyl-4H-1-benzopyran-4-one, 2-(diethylamino)-5,7-methoxy-4H-1-benzopyran-4-one, 2-(ethylamino)-5-hydroxy-4H-1-benzopyran-4-one, 2-(ethylamino)-7-hydroxy-4H-1-benzopyran-4-one, 2-(diethylamino)-7-hydroxy-6-nitro-4H-1-benzopyran-4-one, 2-(diethylamino)-4H-1-benzopyran-4-one,2-(dimethylamino)-7-methoxy-4H-1-benzopyran-4-one, 2-(diethylamino)-7-methoxy-4H-1-benzopyran-4-one, 2-(1-pyrrolidinyl)-7-methoxy-4H-1-benzopyran-4-one, 2-(1-piperidinyl)-7-methoxy-4H-1-benzopyran-4-one, 2-(diethylamino)-7-hydroxy-4H-1-benzopyran-4-one, 2-(1-piperdinyl)-7-hydroxy-4H-1-benzopyran-4-one, 2-(ethylamino)-7-methoxy-4H-1-benzopyran-4-one, 2-(diethylamino)-5-hydroxy-4H-1-benzopyran-4-one, 2-(diethylamino)-5-methyl-8-isopropyl-4H-1-benzopyran-4-one, and 2-(diethylamino)-3-(4-morpohoinomethyl)-7-methoxy-4H-1-benzopyran-4-one, was reported by Mazzei et al. in Eur. J. Med. Chem. 23, 237–242 (May-June 1988); CA 110:75246h.

The literature on the use of an ynamine in the synthesis of a 2-aminochromones has been reported by Tronchet, Bachler and Bonenfant (Tronchet, J. M. J., Bachler, B., Bonenfant, A., Helv. Chim. Acta. (1976), 59, 941). In this report, a 2-amino-3-glycosylchromone was prepared.

2-Amino-1,3-benzoxazin-4-ones are also known in the literature. Specifically, 2-morpholinyl-4H-1,3-benzoxazin-4-one (Cpd98) and 8-methyl-2-(4-morpholinyl) -4H-1,3-benzoxazin-4-one (Cpd84) are described in Netherlands patent application 6,412,966 (see also U.S. Pat. No. 3,491,092), and in the literature (Grigat, E., Putter, R., Schneider, K., Wedemeyer, K., Chem. Ber., (1964) 97, 3036).

The fungicide and analgesic activity of 2-amino-1,3-benzoxazin-4-ones are also claimed by Sankyo in Japn. Tokkyo Koho 79 20,504 (CA 91:157755b) and in Japan (Kokai 72, 17,781 (CA 77:140107e). These patents appear to cover 2-(4-morpholinyl) -4H-1,3-benzoxazin-4-one (Cpd 98) and 6,7-substituted -2-(4-morpholinyl) analogues for the above indications.

The synthesis of 2-dialkylamino-1,3-benzoxazin-4-ones has been described by Kokel et al (see Tet. Letters (1984) 3837).

2-N-Alkyl and 2-N-aryl-1,3-benzoxazin-4-ones have been described by Palazzo and Giannola (Palazzo, S., Giannola, L. I., Atti. Accad. Sci. Lett. Arti Palermo, Parte 1, (1976) 34(2), 83–7).

2-Benzamidino-1,3-benzoxazin-4-one have been described by Brunetti, H., and Luthi, C. E. (in Helv. Chim. Acta., (1972) 55, 1566).

PCT/US89/05526, filed 15 Dec. 1989 (published 28 Jun. 1990) discloses various 1-benzopyran-4-ones and 2-amino-1,3-benzoxazines-4-ones, including 2-(4-morpholinyl) -4H-1-benzopyran-4-one, 8-Methyl-2-(4-morpholinyl)-(7-phenylmethoxy)-4H-benzopyran-4-one, 7-[(1-cyclohexyl -1H-tetrazol-5-yl)methoxy]-8-methyl-2-(4-morpholinyl)-4H-1-benzopyran-4-one, 8-Methyl-2-(4-morpholinyl)-7-(2-(1-piperidinyl)ethyl)oxy-4H-1-benzopyran-4-one, 8-Methyl-2-(4-morpholinyl)-7-(2-(1-pyrrolidinyl)ethyl)oxy-4H-1-benzopyran-4-one, 7-[2-(ethylphenylamino)ethoxy]-8-methyl-2-(4-morpholinyl)-4H-1-Benzopyran-4-one, as well as their antiatherosclerotic, antithrombotic activity, cell proliferation (inhibitive) and/or inhibitive of platelet aggregation.

BRIEF DESCRIPTION OF THE INVENTION

This invention relates to compounds of the Formula I which are useful in association with a pharmaceutical carrier as antiatherosclerotic agents. In addition, various compounds of the Formula I are useful inhibitors of cell proliferation and/or platelet aggregation.

DETAILED DESCRIPTION OF THE INVENTION

The compounds of this invention are represented by Formula I wherein

X is N, or CZ where Z is H, $C_1$–$C_5$ alkyl, amino (—$NM_2$) or a halogen atom;

when X is CZ, Y is selected from the group consisting of —$(CH_2)_nNR_9R_{10}$ wherein $R_9$ and $R_{10}$, being the same or different, are selected from the group consisting of (a) hydrogen, with the provisio that $R_9$ and $R_{10}$ are not both hydrogen;

(b) $C_1$–$C_{12}$ alkyl;

(c) phenyl optionally substituted with one, 2 or 3 $C_1$–$C_4$ alkyl, $C_1$–$C_4$ alkoxy, halo, OH, trifluoromethyl or -$CO_2$ ($C_1$–$C_4$ alkyl);

(d) $(CH_2)_n$phenyl [wherein phenyl is optionally substituted with one, 2 or 3 $C_1$–$C_4$ alkyl, $C_1$–$C_4$ alkoxy, halo, OH, trifluoromethyl or -$CO_2$($C_1$–$C_4$alkyl)], (e) -$(CH_2)_n$pyridinyl or (f) wherein $R_9$ and $R_{10}$, taken together with N, form a saturated or unsaturated heterocyclic amine ring selected from the group consisting of (aa) 4-morpholine optionally substituted with one or two members selected from the group consisting of $C_1$–$C_4$ alkyl, $C_1$–$C_4$ alkoxy, halo or trifluoromethyl, (bb) 4-thiomorpholine optionally substituted with one or two members selected from the group consisting of $C_1$–$C_4$ alkyl, $C_1$–$C_4$ alkoxy, halo or trifluoromethyl, (cc) 3-amino-1-pyrrolidine, (dd) 1-pyrrolidine optionally substituted with one or two members selected from the group consisting of $C_1$–$C_4$ alkyl, $C_1$–$C_4$ alkoxy, halo, OH, -$CH_2$OH, or trifluoromethyl, (ee) 1-piperidine optionally substituted with one or two members selected from the group consisting of $C_1$–$C_4$ alkyl, $C_1$–$C_4$ alkoxy, halo, trifluoromethyl, -$(CH_2)_q$OH, -$CO_2$H, -$CO_2CH_3$, -$CO_2CH_2CH_3$ or phenyl (wherein phenyl is optionally substituted with one, 2 or 3 $C_1$–$C_4$ alkyl, $C_1$–$C_4$ alkoxy, halo or trifluoromethyl), (ff) 1-piperazine, 4-($C_1$–$C_4$alkyl)-1-piperazine (preferably 4-methyl-1-piperazine), 4-(cyclo$C_3$–$C_6$alkyl) -1-piperazine, 4-phenyl-1-piperazine (wherein phenyl is optionally substituted with one, 2 or 3 $C_1$–$C_4$ alkyl, $C_1$–$C_4$ alkoxy, halo or trifluoromethyl) or 4-pyridinyl-1-piperazine optionally substituted with one or two members selected from the group consisting of $C_1$–$C_4$ alkyl, $C_1$–$C_4$ alkoxy, halo, OH, trifluoromethyl, -$CH_2$OH, -$CO_2$H, -$CO_2CH_3$ or -$CO_2CH_2CH_3$ (gg) thiazolidine, thiazolidine-4-carboxylic acid, pipecolinic acid, p-piperazinacetophenone, 1-homopiperazine, 1-methylhomopiperazine, 4-phenyl-1,2-3,6-tetrahydropyridine, proline, tetrahydrofurylamine, 1-(3-hydroxy)pyrrolidine, nipecotamide, 1,2,3,4-tetrahydroisoquinoline or imidazole;

and $R_5$, $R_6$, $R_7$ and $R_8$, being the same or different, are selected from the group consisting of hydrogen, $C_1$–$C_8$ alkyl, -$(CH_2)_n$phenyl [wherein phenyl is optionally substituted with one, 2 or 3 $C_1$–$C_4$ alkyl, $C_1$–$C_4$ alkoxy, halo, OH, trifluoromethyl or -$CO_2$($C_1$–$C_4$ alkyl)], -$(CH_2)_n$naphthyl , -$(CH_2)_n$pyridinyl -$(CH_2)_q$$NR_9R_{10}$, -$CH$=$CH$-phenyl [wherein phenyl is optionally substituted with one, 2 or 3

$C_1$–$C_4$ alkyl, $C_1$–$C_4$ alkoxy, halo, OH, trifluoromethyl or -$CO_2(C_1$–$C_4$alkyl)], -$CH_2$-CH=$CH_2$, -CH=CH-$CH_3$, -CH=$CH_2$, -O-$CH_2$-CH=$CH_2$, -C≡C-phenyl [wherein phenyl is optionally substituted with one, 2 or 3 $C_1$–$C_4$ alkyl, $C_1$–$C_4$ alkoxy, halo, OH, trifluoromethyl or -$CO_2(C_1$-$C_4$alkyl)], -O-$(CH_2)_p$(N-methylpiperdin-3-yl), -O-$(CH_2)_p NR_9 R_{10}$, -O-$CH_2 CH(OCH_3)_2$, -O-$(CH_2)_p OR_{15}$ {wherein $R_{15}$ is selected from H, $C_1$–$C_5$ alkyl, -$(CH_2)_n$phenyl [phenyl optionally substituted with one, 2 or 3 $C_1$–$C_4$ alkyl, $C_1$–$C_4$ alkoxy, halo, OH, trifluoromethyl or -$CO_2(C_1$–$C_4$alkyl)], -$(CH_2)_n$pyridin-1-yl, -$(CH_2)_n$pyridin-2-yl, -$(CH_2)_n$pyridin-3-yl, -$(CH_2)_n$pyridin-4-yl, -$(CH_2)_n$-1-($C_1$–$C_4$alkyl)-1H-5-tetrazole, -$(CH_2)_n$-pyrimidine, -$(CH_2)_n$-2-benzoxazole, -$(CH_2)_n$-2-benzothiazole, -$(CH_2)_n$-($C_1$–$C_4$alkyl) -triazole, -$(CH_2)_n$-($C_1$–$C_4$alkyl)-imidazole}, -O-$(CH_2)_p$-O-$(CH_2)_p$-$OR_{15}$, -O-$(CH_2)_p$-S-$R_{15}$, -O-$(CH_2)_p$-O-$(CH_2)_p NR_9 R_{10}$, -O-$(CH_2)_p$-S-$(CH_2)_p NR_9 R_{10}$, -O-$(CH_2)_p$-S-$(CH_2)_p$-$OR_{15}$, -O-$(CH_2)_p$-S(O)-$R_{15}$, -O-$(CH_2)_p$-S($O_2$)-$R_{15}$, -O-$(CH_2)_p$-S(O)-$(CH_2)_p NR_9 R_{10}$, -O-$(CH_2)_p$-S-(O)-$(CH_2)_p$-$OR_{15}$, -O-$(CH_2)_p$-S($O_2$) -$(CH_2)_p NR_9 R_{10}$, -O-$(CH_2)_p$-S($O_2$) -$(CH_2)_p$-$OR_{15}$, -O-$(CH_2)_p$-[4-[$(CH_2)_p OR_{15}$]-1-piperazine], -O-$(CH_2)_p$-[4-(CH)(phenyl)$_2$-1-piperazine] [phenyl optionally substituted with one, 2 or 3 $C_1$–$C_4$ alkyl, $C_1$–$C_4$ alkoxy, halo, OH, trifluoromethyl or -$CO_2$ ($C_1$–$C_4$alkyl)], -O-$(CH_2)_p$-[4-$(CH_2)_q$phenyl-1-piperazine] [phenyl optionally substituted with one, 2 or 3 $C_1$–$C_4$ alkyl, $C_1$–$C_4$ alkoxy, halo, OH, trifluoromethyl or -$CO_2(C_1$–$C_4$alkyl)], -O-$(CH_2)_p$-[4-$(CH_2)_q$pyridinyl-1-piperazine] [pyridinyl optionally substituted with one, 2 or 3 $C_1$–$C_4$ alkyl, $C_1$–$C_4$ alkoxy, halo, OH, trifluoromethyl, $NR_9 R_{10}$ or -$CO_2$ ($C_1$–$C_4$alkyl)], O-$(CH_2)_p$-[4-($NR_9 R_{10}$ substituted pyridinyl)-1-piperazine, -O-$(CH_2)_p$-(OH substituted 1-piperidine), -O-$(CH_2)_p$-1-pyrrolidin-2-one, -$(CH_2)_n C(O)$-$(CH_2)_n R_9$, -$(CH_2)_n C(O)O$-$(CH_2)_p R_9$, -$(CH_n C(O)O$-$(CH_2)_p NR_9 R_{10}$, -$(CH_2)_n C(O)(CH_2)_n NR_9 R_{10}$, $NO_2$, -O-$(CH_2)_n C(O)$-$(CH_2)_p R_9$, -O-$(CH_2)_n C(O)O$-$(CH_2)_p R_9$, -O-$(CH_2)_n C(O)$-$(CH_2)_n NR_9 R_{10}$, -$NR_9 R_{10}$, -N($R_9$)($CH_2)_n C(O)$-$(CH_2)_n R_{10}$, -N ($R_9$)-$(CH_2)_n C(O)O$-$(CH_2)_n R_{10}$, N($R_9$)($CH_2)_n C(O)$-$(CH_2)_n NR_9 R_{10}$, -O-$(CH_2)_n$phenyl[wherein phenyl is optionally substituted with one, 2 or 3 $C_1$–$C_4$ alkyl, $C_1$–$C_4$ alkoxy, halo, OH, trifluoromethyl or -$CO_2$ ($C_1 C_4$alkyl)], -O-$(CH_2)_n$pyridine, -O($CH_2)_n C(O)$-$(CH_2)_n$pyridine, -O-$(CH_2)_n C(O)O$-$(CH_2)_n$pyridine, -O($CH_2)_n C(O)$-N($R_9$)($CH_2)_n$pyridine, -O-$(CH_2)_n$quinoxalinyl, -O-$(CH_2)_n$quinolinyl, -O-$(CH_2)_n$pyrazinyl, -O-$(CH_2)_n$naphthyl, -O-$(CH_2)_n C(O)$-$(CH_2)_n$naphthyl, -O-$(CH_2)_n C(O)O$-$(CH_2)_n$naphthyl, -O-$(CH_2)_n C(O)NR_9$-$(CH_2)_n$naphthyl, halo (fluoro, chloro, bromo, iodo), OH, -$(CH_2)_q$-OH, $(CH_2)_q OC(O)R_9$, -$(CH_2)_q OC$-(O)-$NR_9 R_{10}$, -(1-cyclohexyl-1H-tetrazol-5-yl) $C_1$–$C_4$ alkoxy, -[1-($C_1$–$C_5$alkyl)-1H-tetrazol-5-yl]$C_1$–$C_4$ alkoxy (including -(1-cycloC$_3$–$C_5$alkyl-1H-tetrazol-5-yl) $C_1 C_4$alkoxy), -[1-(phenyl)-1H-tetrazol-5-yl]$C_1$–$C_4$ alkoxy [wherein phenyl is optionally substituted with one, 2 or 3 $C_1$–$C_4$ alkyl, $C_1$–$C_4$ alkoxy, halo, OH, trifluoromethyl or -$CO_2(C_1$–$C_4$alkyl)], -[1-(pyridinyl)-1H-tetrazol -5-yl]$C_1$–$C_4$ alkoxy, -[1-(1-phenylethyl)-1H-tetrazol -5-yl]$C_1$–$C_4$ alkoxy, -$C_1$–$C_4$ alkoxyl, or a group of Formula II (see Formula Sheet) wherein R' is methyl or carboxy, R" is hydrogen and R'" is selected from benzyl [optionally substituted with one, two or three groups selected from hydroxy, halogen or phenoxy (optionally substituted with one, two or three groups selected from hydroxy or halogen)], $C_1$–$C_5$ alkyl, -$(CH_2)_n CO_2 H$, -$CH_2 SH$, -$CH_2 SCH_3$, imidazolinylmethylene, indolinylmethylene, $CH_3 CH(OH)$, $CH_2 OH$, $H_2 N(CH_2)_4$-(optionally in protected form) or $H_2 NC(NH)NH(CH_2)_3$ (optionally in protected form); with the overall proviso that when Y is other than -$(CH_2)_n$morpholinyl, at least one member of $R_5$, $R_6$, $R_7$ or $R_8$ is other than hydrogen, $C_1$–$C_8$ alkyl, $NO_2$, OH, $C_1$–$C_4$ alkoxy, a halogen atom, phenyl, benzyl, 4-morpholinylmethyl, $NH_2$, or dimethyamino; with the further proviso that when Y is 4-morpholinyl, the compound is other than:

6,7-dimethoxy-2-(4-morpholinyl)-4H-1-benzopyran-4-one;

7,8-(Bis)-(3-trifluoromethyl)phenylmethoxy-2-(4-morpholinyl)-4H-1-benzopyran-4-one;

N-cyclohexyl-2-[[8-methyl-2-(4-morpholinyl)-4-oxo-4H-1-benzopyran-7-yl]oxy]-acetamide;

2-[[8-methyl-2-(4-morpholinyl)-4-oxo-4H-1-benzopyran-7-yl]oxy]-N-phenyl-acetamide;

6-[(1-cyclohexyl-1H-tetrazol-5-yl)methoxy]-2-(4-morpholinyl)-4H-1-benzopyran-4-one;

2-[[8-methyl-2-(4-morpholinyl)-4-oxo-4H-1-benzopyran-7-yl]oxy]-N-(1-phenylethyl)-acetamide;

with the further provisio that when Y is dimethylamino, the compound is other than:

2-(Dimethylamino)-8-methyl-4-oxo-4H-1-benzopyran-7-yl carbamic acid dimethyl ester;

(Dimethylamino)-4-oxo-4H-1-benzopyran-6-yl carbamic acid dimethyl ester;

2-(Dimethylamino)-4-oxo-4H-1-benzopyran-7-yl carbamic acid dimethyl ester;

when X is N, Y is selected from the group consisting of -$NR_9 R_{10}$ wherein $R_9$ and $R_{10}$, being the same or different, are selected from the group consisting of (a) hydrogen, with the provisio that $R_9$ and $R_{10}$ are not both hydrogen;

(b) $C_1$–$C_{12}$ alkyl;

(c) phenyl optionally substituted with one, 2 or 3 $C_1$–$C_4$ alkyl, $C_1$–$C_4$ alkoxy, halo, OH, trifluoromethyl or -$CO_2$ ($C_1$–$C_4$alkyl);

(d) -$(CH_2)_n$phenyl [wherein phenyl is optionally substituted with one, 2 or 3 $C_1$–$C_4$ alkyl, $C_1$–$C_4$ alkoxy, halo, OH, trifluoromethyl or -$CO_2(C_1$–$C_4$alkyl)], (e) -$(CH_2)_n$pyridinyl or (f) wherein $R_9$ and $R_{10}$, taken together with N, form a saturated or unsaturated heterocyclic amine ring selected from the group consisting of (aa) 4-morpholine optionally substituted with one or two members selected from the group consisting of $C_1$–$C_4$ alkyl, $C_1$–$C_4$ alkoxy, halo or trifluoromethyl, (bb) 4-thiomorpholine optionally substituted with one or two members selected from the group consisting of $C_1$–$C_4$ alkyl, $C_1$–$C_4$ alkoxy, halo or trifluoromethyl, (cc) 3-amino-1-pyrrolidine, (dd) 1-pyrrolidine optionally substituted with one or two members selected from the group consisting of $C_1$–$C_4$ alkyl, $C_1$–$C_4$ alkoxy, halo, OH, -$CH_2 OH$, or trifluoromethyl, (ee) 1-piperidine optionally substituted with one or two members selected from the group consisting of $C_1$–$C_4$ alkyl, $C_1$–$C_4$ alkoxy, halo, trifluoromethyl, -$(CH_2)_q OH$, -$CO_2 H$, -$CO_2 CH_3$, -$CO_2 CH_2 CH_3$ or phenyl (wherein phenyl is optionally substituted with one, 2 or 3 $C_1$–$C_4$ alkyl, $C_1$–$C_4$ alkoxy, halo or trifluoromethyl), (ff) 1-piperazine, 4-($C_1$–$C_4$alkyl)-1-piperazine (preferably 4-methyl-1-piperazine), 4-phenyl-1-piperazine (wherein phenyl is optionally substituted with one, 2 or 3 $C_1$–$C_4$ alkyl, $C_1$–$C_4$ alkoxy, halo or trifluoromethyl) or 4-pyridinyl-1-piperazine optionally substituted with one or two members selected from the group consisting of $C_1$–$C_4$ alkyl, $C_1$–$C_4$ alkoxy, halo, OH, trifluoromethyl, -$CH_2OH$, -$CO_2H$, -$CO_2CH_3$ or -$CO_2CH_2CH_3$, and (gg) thiazolidine, thiazolidine-4-carboxylic acid, pipecolinic acid, p-piperazinacetophenone, 1-homopiperazine, 1-methylhomopiperazine, 4-phenyl-1,2-3,6-tetrahydropyridine, proline, tetrahydrofurylamine, 1-(3-hydroxy)pyrrolidine, nipecotamide, 1,2,3,4-tetrahydroisoquinoline or imidazole;

and $R_5$, $R_6$, $R_7$ and $R_8$, being the same or different, are selected from the group consisting of hydrogen, $C_1$–$C_8$ alkyl, -$(CH_2)_n$phenyl [wherein phenyl is optionally substituted with one, 2 or 3 $C_1$–$C_4$ alkyl, $C_1$–$C_4$ alkoxy, halo, OH, trifluoromethyl or -$CO_2(C_1$–$C_4$alkyl)], -$(CH_2)_n$naphthyl, -$(CH_2)_n$pyridinyl, -$(CH_2)_q NR_9 R_{10}$, -CH=CH-phenyl [wherein phenyl is optionally substituted with one, 2 or 3 $C_1$–$C_4$ alkyl, $C_1$–$C_4$ alkoxy, halo, OH, trifluoromethyl or -$CO_2(C_1$–$C_4$alkyl)], -$CH_2$-CH=$CH_2$, -CH=CH-$CH_3$, -CH=$CH_2$, -O-$CH_2$-CH=$CH_2$, -C≡C-phenyl [wherein phenyl is optionally substituted with one, 2 or 3 $C_1$–$C_4$ alkyl, $C_1$–$C_4$ alkoxy, halo, OH, trifluoromethyl or -$CO_2(C_1$–$C_4$alkyl)], -O$(CH_2)_p$(N-methylpiperdin-3-yl), -O-$(CH_2)_p NR_9 R_{10}$, -O-$CH_2CH(OCH_3)_2$, -O-$(CH_2)_p OR_{15}$ {wherein $R_{15}$ is selected from H, $C_1$–$C_5$ alkyl, -$(CH_2)_n$phenyl [phenyl optionally substituted with one, 2 or 3 $C_1$–$C_4$ alkyl, $C_1$–$C_4$ alkoxy, halo, OH, trifluoromethyl or -$CO_2(C_1$–$C_4$alkyl)], -$(CH_2)_n$pyridin-1-yl, -$(CH_2)_n$pyridin-2-yl, -$(CH_2)_n$pyridin-3-yl, -$(CH_2)_n$pyridin-4-yl, -$(CH_2)_n$-1-$(C_1$–$C_4$alkyl)-1H-5-tetrazole, -$(CH_2)_n$-pyrimidine, -$(CH_2)_n$-2-benzoxazole, -$(CH_2)_n$-2-benzothiazole, -$(CH_2)_n$-$(C_1$–$C_4$alkyl)-triazole, -$(CH_2)_n$-$(C_1$–$C_4$alkyl)-imidazole}, -O-$(CH_2)_p$-O-$(CH_2)_p$-$OR_{15}$, -O-$(CH_2)_p$-S-$R_{15}$, -O-$(CH_2)_p$-O-$(CH_2)_p NR_9 R_{10}$, -O-$(CH_2)_p$-S-$(CH_2)_p NR_9 R_{10}$, -O-$(CH_2)_p$-S-$(CH_2)_p$-$OR_{15}$, -O-$(CH_2)_p$-S(O)-$R_{15}$, -O-$(CH_2)_p$-$S(O_2)$-$R_{15}$, -O-$(CH_2)_p$-S(O)-$(CH_2)_p NR_9 R_{10}$, -O-$(CH_2)_p$-S(O)-$(CH_2)_p$-$OR_{15}$, -O-$(CH_2)_p$-$S(O_2)$-$(CH_2)_p NR_9 R_{10}$, -O-$(CH_2)_p$-$S(O_2)$-$(CH_2)_p$-$OR_{15}$, -O-$(CH_2)_p$-[4-[$(CH_2)_p OR_{15}$]-1-piperazine], -O-$(CH_2)_p$-[4-(CH) (phenyl)$_2$-1-piperazine] [phenyl optionally substituted with one, 2 or 3 $C_1$–$C_4$ alkyl, $C_1$–$C_4$ alkoxy, halo, OH, trifluoromethyl or -$CO_2$ $(C_1$–$C_4$alkyl)], -O-$(CH_2)_p$-[4-$(CH_2)_q$phenyl-1-piperazine] [phenyl optionally substituted with one, 2 or 3 $C_1$–$C_4$ alkyl, $C_1$–$C_4$ alkoxy, halo, OH, trifluoromethyl or -$CO_2(C_1$–$C_4$alkyl)], -O-$(CH_2)_p$-[4-$(CH_2)_q$pyridinyl-1-piperazine] [pyridinyl optionally substituted with one, 2 or 3 $C_1$–$C_4$ alkyl, $C_1$–$C_4$ alkoxy, halo, OH, trifluoromethyl, $NR_9 R_{10}$ or -$CO_2$ $(C_1$–$C_4$alkyl)], O-$(CH_2)_p$-[4-$(NR_9 R_{10}$ substituted pyridinyl) -1-piperazine, -O-$(CH_2)_p$-(OH substituted 1-piperidine) , -O-$(CH_2)_p$-1-pyrrolidin-2-one, -$(CH_2)_n C(O)$-$(CH_2)_n R_9$, -$(CH_2)_n C(O)O$-$(CH_2)_p R_9$, -$(CH)_n C(O)O$-$(CH_2)_p NR_9 R_{10}$, -$(CH_2)_n C(O)$ $(CH_2)_n NR_9 R_{10}$, $NO_2$, -O-$(CH_2)_n C(O)$-$(CH_2)_p R_9$, -O-$(CH_2)_n C(O)O$-$(CH_2)_p R_9$, -O-$(CH_2)_n C(O)$-$(CH_2)_n NR_9 R_{10}$, -$NR_9 R_{10}$, -$N(R_9)$ $(CH_2)_n C(O)$-$(CH_2)_n R_{10}$, -$N(R_9)$-$(CH_2)_n C(O)O$-$(CH_2)_n R_{10}$, $N(R_9)$ $(CH_2)_n C(O)$-$(CH_2)_n NR_9 R_{10}$, -O-$(CH_2)_n$phenyl [wherein phenyl is optionally substituted with one, 2 or 3 $C_1$–$C_4$ alkyl, $C_1$–$C_4$ alkoxy, halo, OH, trifluoromethyl or -$CO_2$ $(C_1$–$C_4$alkyl), -O-$(CH_2)_n$pyridine, -O$(CH_2)_n C(O)$-$(CH_2)_n$pyridine, -O-$(CH_2)_n C(O)O$-$(CH_2)_n$pyridine, -O$(CH_2)_n C(O)$-N$(R_9)$ $(CH_2)_n$pyridine, -O-$(CH_2)_n$quinoxalinyl, -O-$(CH_2)_n$quinolinyl, -O-$(CH_2)_n$pyrazinyl, -O-$(CH_2)_n$naphthyl, -O-$(CH_2)_n C(O)$-$(CH_2)_n$naphthyl, -O-$(CH_2)_n C(O)O$-$(CH_2)_n$naphthyl, -O-$(CH_2)_n C(O)$ $NR_9$-$(CH_2)_n$naphthyl, halo (fluoro, chloro, bromo, iodo), OH, -$(CH_2)_q$-OH, -$(CH_2)_q OC(O)$ $R_9$, -$(CH_2)_q OC$-(O)-$NR_9 R_{10}$, -(1-cyclohexyl-1H-tetrazol-5-yl)$C_1$–$C_4$ alkoxy, -[1-($C_1$–$C_5$alkyl)-1H-tetrazol-5-yl]$C_1$–$C_4$ alkoxy (including -(1-cyclo$C_3$–$C_5$ alkyl-1H-tetrazol-5-yl) $C_1 C_4$alkoxy) , -[1-($_p$henyl) -1H-tetrazol-5-yl]$C_1$–$C_4$ alkoxy [wherein phenyl is optionally substituted with one, 2 or 3 $C_1$–$C_4$ alkyl, $C_1$–$C_4$ alkoxy, halo, OH, trifluoromethyl or -$CO_2(C_1$–$C_4$alkyl)], -[1-(pyridinyl)-1H-tetrazol-5-yl]$C_1$–$C_4$ alkoxy, -[1-(1-phenylethyl)-1H-tetrazol-5-yl]$C_1$–$C_4$ alkoxy, or -$C_1$–$C_4$ alkoxyl, or a group of Formula II (see Formula Sheet) wherein R' is methyl or carboxy, R" is hydrogen and R'" is selected from benzyl [optionally substituted with one, two or three groups selected from hydroxy, halogen or phenoxy (optionally substituted with one, two or three groups selected from hydroxy or halogen)], $C_1$–$C_5$ alkyl, -$(CH_2)_n CO_2 H$, -$CH_2 SH$, -$CH_2 SCH_3$, imidazolinylmethylene, indolinylmethylene, $CH_3 CH(OH)$, $CH_2 OH$, $H_2 N(CH_2)_4$-(optionally in protected form) or $H_2 NC(NH)NH(CH_2)_3$ (optionally in protected form);

n is 0–5, preferably 0 or one;

p is 2–5, preferably 2 or 3;

q is 1–5, preferably 1 or 2;

and pharmaceutically acceptable salts thereof.

X is preferably CZ where Z is H or $C_1$–$C_5$ alkyl, more preferably H or methyl, most preferably H.

When X is CZ, Y is preferably selected from the group consisting of -$(CH_2)_n NR_9 R_{10}$ wherein $R_9$ and $R_{10}$, taken together with N, form a saturated or unsaturated heterocyclic amine ring selected from the group consisting of:

(aa) 4-morpholine optionally substituted with one or two members selected from the group consisting of $C_1$–$C_4$ alkyl, $C_1$–$C_4$ alkoxy, halo or trifluoromethyl, (bb) 4-thiomorpholine optionally substituted with one or two members selected from the group consisting of $C_1$–$C_4$ alkyl, $C_1$–$C_4$ alkoxy, halo or trifluoromethyl, (cc) 3-amino-1-pyrrolidine, (dd) 1-pyrrolidine optionally substituted with one or two members selected from the group consisting of $C_1$–$C_4$ alkyl, $C_1$–$C_4$ alkoxy, halo, OH, -$CH_2OH$, or trifluoromethyl, (ee) 1-piperidine optionally substituted with one or two members selected from the group consisting of $C_1$–$C_4$ alkyl, $C_1$–$C_4$ alkoxy, halo, trifluoromethyl, -$(CH_2)_q OH$, -$CO_2H$, -$CO_2CH_3$, -$CO_2CH_2CH_3$ or phenyl (wherein phenyl is optionally substituted with one, 2 or 3 $C_1$–$C_4$ alkyl, $C_1$–$C_4$ alkoxy, halo or trifluoromethyl), and (ff) 1-piperazine, 4-methyl-1-piperazine, 4-phenyl-1-piperazine (wherein phenyl is optionally substituted with one, 2 or 3 $C_1$–$C_4$ alkyl, $C_1$–$C_4$ alkoxy, halo or trifluoromethyl) or 4-pyridinyl-1-piperazine optionally substituted with one or two members selected from the group consisting of $C_1$–$C_4$ alkyl, $C_1$–$C_4$ alkoxy, halo, trifluoromethyl, -$CH_2OH$, -$CO_2H$, -$CO_2CH_3$ or -$CO_2CH_2CH_3$.

When X is CZ wherein Z is H or $C_1$–$C_5$ alkyl (most preferably H), Y is more preferably selected from the group consisting of -$(CH_2)_n NR_9 R_{10}$ wherein n is 0 or 1 (most preferably 0) and $R_9$ and $R_{10}$, taken together with N, form:

(aa) morpholine (preferably 4-morpholine) optionally substituted with one or two members selected from the group consisting of $C_1$–$C_4$ alkyl or phenyl (wherein phenyl is optionally substituted with one or 2 $C_1$–$C_4$ alkyl, $C_1$–$C_4$ alkoxy, halo or trifluoromethyl);

and preferably, at least one member selected from $R_5$, $R_6$, $R_7$ or $R_8$ is selected from the group consisting of -$(CH_2)_p$phenyl [wherein phenyl is optionally substituted with one, 2 or 3 $C_1$–$C_4$ alkyl, $C_1$–$C_4$ alkoxy, halo, OH, trifluoromethyl or -$CO_2$($C_1$-$C_4$alkyl)], -$(CH_2)_n$naphthyl, -$(CH_2)_n$pyridinyl, -$(CH_2)_q$$NR_9R_{10}$, -CH=CH-phenyl [wherein phenyl is optionally substituted with one, 2 or 3 $C_1$-$C_4$ alkyl, $C_1$-$C_4$ alkoxy, halo, OH, trifluoromethyl or -$CO_2$ ($C_1$-$C_4$alkyl)], -$CH_2$-CH=$CH_2$, -CH=CH-$CH_3$, -O-$CH_2$-CH=$CH_2$, -C≡C-phenyl [wherein phenyl is optionally substituted with one, 2 or 3 $C_1$-$C_4$ alkyl, $C_1$-$C_4$ alkoxy, halo, OH, trifluoromethyl or $CO_2$($C_1$-$C_4$alkyl)], -O($CH_2$)$_p$(N-methylpiperdin-3-yl) , -O-$(CH_2)_p$$NR_9R_{10}$, -O-$CH_2CH(OCH_3)_2$, -O-$(CH_2)_p$$OR_{15}$, -O-$(CH_2)_p$-S-$R_{15}$, -$(CH_2)_n$C(O)-$(CH_2)_p$$R_9$, -$(CH_2)_n$C(O)O-$(CH_2)_p$$R_9$, -$(CH)_n$C(O)O-$(CH_2)_p$$NR_9R_{10}$, -$(CH_2)_n$C(O)$(CH_2)_n$$NR_9R_{10}$, -O-$(CH_2)_n$C(O)-$(CH_2)_p$$R_9$, -O-$(CH_2)_n$C(O)O-$(CH_2)_p$$R_9$, -O-$(CH_2)_n$C(O)-$(CH_2)_n$$NR_9R_{10}$, -$NR_9R_{10}$, -N($R_9$) $(CH_2)_n$C(O)-$(CH_2)_n$$R_{10}$, -N($R_9$)-$(CH_2)_n$C(O)O-$(CH_2)_n$$R_{10}$, N($R_9$) $(CH_2)_n$C(O)-$(CH_2)_n$$NR_9R_{10}$, -O-$(CH_2)_n$phenyl [wherein phenyl is optionally substituted with one, 2 or 3 $C_1$-$C_4$ alkyl, $C_1$-$C_4$ alkoxy, halo, OH, trifluoromethyl or -$CO_2$ ($C_1$-$C_4$alkyl)], -O-$(CH_2)_n$pyridine, -O($CH_2$)$_n$C(O)-$(CH_2)_n$pyridine, -O-$(CH_2)_n$C(O)O-$(CH_2)_n$pyridine, -O($CH_2$)$_n$C(O)-N($R_9$)$(CH_2)_n$pyridine, -O-$(CH_2)_n$quinoxalinyl, -O-$(CH_2)_n$quinolinyl, -O-$(CH_2)_n$pyrazinyl, -O-$(CH_2)_n$naphthyl, -O-$(CH_2)_n$C(O)-$(CH_2)_n$naphthyl, -O-$(CH_2)_n$C(O)O-$(CH_2)_n$naphthyl, -O-$(CH_2)$ C(O)N$R_9$-$(CH_2)_n$naphthyl, -$(CH_2)_q$-OH, -$(CH_2)_q$OC(O)$R_9$, $(CH_2)_q$OC(O)-N$R_9R_{10}$, -(1-cyclohexyl-1H-tetrazol-5-yl)$C_1$-$C_4$ alkoxy, -[1-($C_1$-$C_5$alkyl)-1H-tetrazol-5-yl]$C_1$-$C_4$ alkoxy, -[1-($_p$henyl)-1H-tetrazol-5-yl]$C_1$-$C_4$ alkoxy [wherein phenyl is optionally substituted with one, 2 or 3 $C_1$-$C_4$ alkyl, $C_1$-$C_4$ alkoxy, halo, OH, trifluoromethyl or -$CO_2$($C_1$-$C_4$alkyl)], -[1-(pyridinyl)-1H-tetrazol-5-yl]$C_1$-$C_4$ alkoxy, -[1-(1-phenylethyl)-1H-tetrazol-5-yl]$C_1$-$C_4$ alkoxy, or -$C_1$-$C_4$ alkoxyl; more preferably, (i) $R_5$, $R_6$, $R_7$ and $R_8$ are each hydrogen; or (ii) $R_5$, $R_6$, and $R_8$ are each hydrogen, and $R_7$ is selected from: -O-$(CH_2)_n$phenyl (wherein phenyl is optionally substituted with one, 2 or 3 $C_1$-$C_4$ alkyl, $C_1$-$C_4$ alkoxy, halo or trifluoromethyl), -C≡C-phenyl (wherein phenyl is optionally substituted with one, 2 or 3 $C_1$-$C_4$ alkyl, $C_1$-$C_4$ alkoxy, halo or trifluoromethyl), or -$(CH_2)_n$phenyl (wherein phenyl is optionally substituted with one, 2 or 3 $C_1$-$C_4$ alkyl, $C_1$-$C_4$ alkoxy, halo or trifluoromethyl); or (iii) $R_5$ and $R_6$ are hydrogen, $R_8$ is hydrogen, halo or $C_1$-$C_5$alkyl, and $R_7$ is selected from: -O-$(CH_2)_n$phenyl (wherein phenyl is optionally substituted with one, 2 or 3 $C_1$-$C_4$ alkyl, $C_1$-$C_4$ alkoxy, halo or trifluoromethyl), -O-$(CH_2)_n$pyridinyl (wherein pyridinyl is optionally substituted with one, 2 or 3 $C_1$-$C_4$ alkyl, $C_1$-$C_4$ alkoxy, halo or trifluoromethyl), -O-$(CH_2)_n$naphthyl, -$(CH_2)_n$phenyl (wherein phenyl is optionally substituted with one, 2 or 3 $C_1$-$C_4$ alkyl, $C_1$-$C_4$ alkoxy, halo or trifluoromethyl), -$(CH_2)_p$pyridinyl (wherein pyridinyl is optionally substituted with one, 2 or 3 $C_1$-$C_4$ alkyl, $C_1$-$C_4$ alkoxy, halo or trifluoromethyl), -$(CH_2)_p$(1-piperidinyl), -$(CH_2)_p$(1-pyrrolidinyl), -O-$(CH_2)_p$$NR_9R_{10}$, -O-$(CH_2)_p$-O-$R_{15}$, -O-$(CH_2)_p$-S-$R_{15}$, or -[(1-cyclohexyl-1H-tetrazol-5-yl)-$C_1$-$C_4$alkoxy; or (iv) $R_5$, $R_7$ and $R_8$ are each hydrogen, and $R_6$ is -NH-C(O)-O-$CH_2$phenyl; or (v) $R_5$ and $R_6$ are hydrogen, $R_8$ is hydrogen, -CH=$CH_2$, halo or $C_1$-$C_5$ alkyl, and $R_7$ is selected from: -O-$(CH_2)_n$phenyl (wherein phenyl is optionally substituted with one, 2 or 3 $C_1$-$C_4$ alkyl, $C_1$-$C_4$ alkoxy, halo or trifluoromethyl), -O-$(CH_2)_n$pyridinyl (wherein pyridinyl is optionally substituted with one, 2 or 3 $C_1$-$C_4$ alkyl, $C_1$-$C_4$ alkoxy, halo or trifluoromethyl), -O-$(CH_2)_n$naphthyl, -$(CH_2)_n$phenyl (wherein phenyl is optionally substituted with one, 2 or 3 $C_1$-$C_4$ alkyl, $C_1$-$C_4$ alkoxy, halo or trifluoromethyl), -$(CH_2)_p$pyridinyl (wherein pyridinyl is optionally substituted with one, 2 or 3 $C_1$-$C_4$ alkyl, $C_1$-$C_4$ alkoxy, halo or trifluoromethyl), -$(CH_2)_p$(1-piperidinyl), -$(CH_2)_p$(1-pyrrolidinyl), -O-$(CH_2)_p$$NR_9R_{10}$ [preferably-O-$(CH_2)_p$-4-($C_1$-$C_4$alkyl)-1-piperazine, -O-$(CH_2)_p$(1-piperidinyl), -O-$(CH_2)_p$(1-pyrrolidinyl), more preferably -O-$(CH_2)_2$-4-methyl-1-piperazine], -O-$(CH_2)_p$-O-$R_{15}$, -O-$(CH_2)_p$-S-$R_{15}$, -[1-($C_1$-$C_5$alkyl)-1H-tetrazol-5-yl]$C_1$-$C_4$ alkoxy, or -[(1-cyclohexyl-1H-tetrazol-5-yl]$C_1$-$C_4$ alkoxy; or (vi) $R_5$, $R_6$ and $R_7$ are hydrogen, and $R_8$ is selected from: -C≡C-phenyl (wherein phenyl is optionally substituted with one, 2 or 3 $C_1$-$C_4$ alkyl, $C_1$-$C_4$ alkoxy, halo or trifluoromethyl), -O-$(CH_2)_n$phenyl (wherein phenyl is optionally substituted with one, 2 or 3 $C_1$-$C_4$ alkyl, $C_1$-$C_4$ alkoxy, halo or trifluoromethyl), -O-$(CH_2)_n$pyridinyl (wherein pyridinyl is optionally substituted with one, 2 or 3 $C_1$-$C_4$ alkyl, $C_1$-$C_4$ alkoxy, halo or trifluoromethyl), -O-$(CH_2)_n$naphthyl, -$(CH_2)_n$phenyl (wherein phenyl is optionally substituted with one, 2 or 3 $C_1$-$C_4$ alkyl, $C_1$-$C_4$ alkoxy, halo or trifluoromethyl), -$(CH_2)_p$pyridinyl (wherein pyridinyl is optionally substituted with one, 2 or 3 $C_1$-$C_4$ alkyl, $C_1$-$C_4$ alkoxy, halo or trifluoromethyl), -$(CH_2)_p$(1-piperidinyl), -$(CH_2)_p$(1-pyrrolidinyl), -O-$(CH_2)_p$$NR_9R_{10}$ [preferably -O-$(CH_2)_p$-4-($C_1$-$C_4$alkyl)-1-piperazine, -O-$(CH_2)_p$(1-piperidinyl), -O-$(CH_2)_p$(1-pyrrolidinyl), more preferably -O-$(CH_2)_2$-4-methyl-1-piperazine], -O-$(CH_2)_p$-O-$R_{15}$, -O-$(CH_2)_p$-S-$R_{15}$, -[1-($C_1$-$C_5$alkyl)-1H-tetrazol-5-yl]$C_1$-$C_4$ alkoxy, or -[(1-cyclohexyl-1H-tetrazol-5-yl]$C_1$-$C_4$ alkoxy.

A further embodiment of the subject invention is when X is CZ wherein Z is H or $C_1$-$C_5$ alkyl (most preferably H), Y is more preferably selected from the group consisting of -$(CH_2)_n$$NR_9R_{10}$ wherein n is 0 or 1 (most preferably 0) and $R_9$ and $R_{10}$, taken together with N, form:

(aa) morpholine (preferably 4-morpholine) optionally substituted with one or two members selected from the group consisting of $C_1$-$C_4$ alkyl or phenyl (wherein phenyl is optionally substituted with one or 2 $C_1$-$C_4$ alkyl, $C_1$-$C_4$ alkoxy, halo or trifluoromethyl);

and preferably, at least one member selected from $R_5$, $R_6$, $R_7$ or $R_8$ is selected from the group consisting of -O-$(CH_2)_p$-S-$R_{15}$, -O-$(CH_2)_p$-[4-(CH)phenyl)$_2$-1-piperazine], -CH=$CH_2$, or -O-$(CH_2)_p$O-$(CH_2)_p$$OR_{15}$; more preferably, (i) $R_5$, $R_6$, and $R_7$ are each hydrogen, and $R_8$ is selected from: -O-$(CH_2)_p$-[4-(CH)phenyl)$_2$-1-piperazine], or -O-$(CH_2)_p$-S-$R_{15}$; or (ii) $R_5$ and $R_6$ are hydrogen, $R_8$ is hydrogen, halo, -CH=$CH_2$, or $C_1$-$C_5$ alkyl, and $R_7$ is selected from: -O-$(CH_2)_p$-[4-(CH)phenyl)$_2$-1-piperazine], or -O-$(CH_2)_p$-S-$R_{15}$.

X is most preferably CH.

Y is most preferably 4-morpholinyl.

$R_8$ is preferably hydrogen or $C_1$-$C_5$ alkyl, more preferably hydrogen or methyl.

$R_{15}$ is preferably hydrogen, $C_1$-$C_5$ alkyl, -$(CH_2)_n$phenyl, -$(CH_2)_n$pyridin-2-yl or -$(CH_2)_n$pyridin-3-yl.

Examples of preferred compounds include: Compounds 2, 3, 14, 19, 28, 51, 72, 76, 84, 95, 96, 98, 112, 128, 139, 163, 164, 171, 188, 204, 208, 233, 266, 283, 293, 304, 326, 332 and 347; as well as salts thereof. Compound 208 and salts thereof (e.g., Compound 239) is particularly preferred.

Accordingly the present invention includes the novel 2-amino(4H)-1-benzopyran-4-ones and 2-aminoalkyl (4H)-

1-benzopyran-4-ones of Formula I when X is CZ and the antiatherosclerotic utility of said compounds as well as the antiatherosclerotic utility of the known compounds of Formula I, including the 2-amino-1,3-benzoxazine-4-ones of Formula IB.

The carbon content of various hydrocarbon containing moieties is indicated by a prefix designating the minimum and maximum number of carbon atoms in the moiety, i.e., the prefix $C_i$-$C_j$ indicates a carbon atoms content of the integer "i" to the integer "j" carbon atoms, inclusive. Thus, $C_1$-$C_3$ alkyl refers to alkyl of 1–3 carbon atoms, inclucive, or methyl, ethyl, propyl, and isopropyl.

With respect to the above, $C_1$-$C_4$ alkyl is methyl, ethyl, propyl, or butyl, including isomeric forms thereof. Similarly, $C_1$-$C_6$ alkyl is methyl, ethyl, propyl, butyl, pentyl, hexyl, and isomeric forms thereof.

The term "halo" includes fluoro, chloro, bromo and iodo.

All temperatures throughout the specification are expressed in degrees Celcius (°C.).

Examples of $C_1$-$C_8$ alkylthiomethyl are methylthiomethyl, ethylthiomethyl, propylthiomethyl, butylthiomethyl, pentylthiomethyl, hexylthiomethyl, and heptylthiomethyl, and isomeric forms thereof.

Examples of $C_1$-$C_8$ alkoxymethyl are methoxymethyl, ethoxymethyl, propoxymethyl, butoxymethyl, pentoxymethyl, butoxymethyl, pentoxymethyl, hexoxymethyl, and heptoxymethyl, and isomeric forms thereof.

Examples of heterocylic amines corresponding to heterocyclic amine rings according to -$NR_9N_{10}$ are:
4-morpholine,
4-phenyl-1-piperazine,
4-(2-pyridinyl)-1-piperazine,
2,6-dimethyl-4-morpholine,
1-pyrrolidine,
4-methyl-1-piperazine,
1-piperidine,
4-phenyl-1-piperidine
thiazolidine,
3-piperidine methanol,
2-piperidine methanol,
pipecolic acid,
3-piperidine ethanol,
2-piperidine ethanol,
1-piperazine propanol,
p-piperazinoacetophenone,
4-phenyl-1,2,3,6-tetrahydropyridine,
4-phenylpiperidine,
proline,
1-(3-hydroxy)pyrrolidine,
tetrahydrofurylamine,
pyrrolidimethanol,
3-pyrroline,
thiazolidine-4-carboxylic acid,
thiomorpholine,
nipecotamide,
2-methylpiperidine,
3-methylpiperidine,
4-methylpiperidine,
N-methylpiperazine,
1-methylhomopiperazine,
1-acetylpiperazine,
N-carboethoxypiperazine,
3-methylpiperazine-2-carboxylic acid,
2-methylpiperazine,
2,3,5,6,-tetramethylpiperazine,
1,4-dimethylpiperazine,
2,6-dimethylpiperazine,
2-methyl-1-phenylpiperazine,
1-(1-phenylethyl)piperazine,
1-(2-pyrazinyl)piperazine,
1-cyclopropylpiperazine,
1-cyclobutylpiperazine,
1,2,3,4-tetrahydroisoquinoline,
imidazole,
homopiperdine, and pharmaceutically acceptable salts and hydrates thereof.

Examples of -$O(CH_2)_p$(N-methylpiperdin-3-yl) include (2-(N-methylpiperdin-3-yl)ethyl)oxy, (3-(N-methylpiperdin-3-yl)propyl)oxy, (4-(N-methylpiperdin-3-yl)butyl)oxy.

Examples of -$O-(CH_2)_pNR_9R_{10}$ include (2-(1-piperidinyl)ethyl)oxy, (2-(4-morpholinyl)ethyl)oxy, (2-(1-pyrrolidinyl)ethyl)oxy, (3-(N-methylpiperazinyl)propyl)oxy, (4-(N-ethyl-N-phenylamino)butyl)oxy, (5-(diethylamino)pentyl)oxy, (2-(4-benzylpiperazinyl)ethyl)oxy, and (3-(N,N-diisopropyl)propyl)oxy.

Examples of $O-(CH_2)_pOR_{15}$ include (2-methoxyethyl)oxy, (3-butoxypropyl)oxy, (4-phenoxybutyl)oxy, (2-benzyloxyethyl)oxy, (2-(2-(1-piperidinyl)ethoxy)ethyl)oxy and (3-(3-picolylmethoxy)propyl)oxy.

Examples of -$(CH_2)_n$pyridinyl include 2-pyridyl, 3-pyridylmethyl and 4-pyridylethyl.

Examples of -$(CH_2)_n$piperdinyl include 1-piperidinyl, 1-peiperidinylmethyl, 2-(1-piperidinyl)ethyl and 3-(1-piperidinyl)propyl.

Examples of -$(CH_2)qNR9R10$ include (1-piperidinyl)methyl, 2-(4-morpholinyl)ethyl, 3-(1-pyrrolindinyl)propyl and 4-(1-piperazinyl)butyl.

Examples of -$(CH_2)_nC(O)-(CH_2)_nR_9$ include acetyl, acetylmethyl, methylacetylmethyl, methylacetylethyl, phenylacetyl, phenylacetylmethyl, 2-(phenylacetyl)ethyl, 2-pyridylacetyl, 3-pyridylacetylmethyl, 3-(t-butylacetyl)propyl and 4-(ethylacetyl)butyl.

Examples of -$(CH_2)_nC(O)O-(CH_2)_pR_9$ include carbomethoxy, carbomethoxymethyl, 2-(carbomethoxy)ethyl, carbophenylmethoxy, carbophenylmethoxymethyl, 2-(carbo(3-pyridyl)methoxy)ethyl, carboethoxymethyl and 3-(carbopropoxy)propoxy.

Examples of -$(CH_2)_nC(O)O-(CH_2)_pNR_9R_{10}$ include -$_c$(O)O-(CH_2)_2N(ethyl)_2$,-$(CH_2)C(O)O-(CH_2)_2N(CH_3)(phenyl)$, -$(CH_2)_3C(O)O-(CH_2)_3$ (1-pyrrolidine), -$(CH_2)_3C(O)O-(CH_2)_2$ (1-piperidinyl), and -$(CH_2)C(O)O-(CH_2)_2$(4-morpholinyl).

Examples of -$(CH_2)_nC(O) (CH_2)_nNR_9R_{10}$ include -$(CH_2)C(O)(CH_2)_2N(ethyl)_2$, -$(CH_2)_2C(O) (CH_2)_2N(methyl)(phenyl)$, -C(O) (1-pyrrolidine), -$(CH_2)_2C(O)(CH_2)_3$(1-piperidine), and -$(CH_2)_3C(O) (CH_2)$ (4-morpholine).

Examples of -$O-(CH_2)_nC(O)-(CH_2)_pR_9$ include -$O-(CH_2)C(O)-(CH_2) (CH_3)$, -$O-C(O)-(CH_2)_2 (CH_3)$, -$O-(CH_2)_3C(O)-(CH_2)$ phenyl, -$O-(CH_2)_2C(O)-(CH_2)_3$ (2-pyridyl), -$O-(CH_2)C(O)-(CH_2)_2$(3-pyridyl) and -$O-(CH_2)_4C(O)-(CH_2)_4$ (t-butyl).

Examples of -$O-(CH_2)_nC(O)O-(CH_2)_pR_9$ include -$O-(CH_2) C(O)O-(CH_2) (CH_3)$, -$O-C(O)O-(CH_2)_2(CH_3)$, -$O-(CH_2)_2C(O)O-(CH_2)_3(phenyl)$ and -$O-(CH_2)_3C(O)O-(CH_2)_2$(3-pyridyl).

Examples of -$O-(CH_2)_nC(O)-(CH_2)_nNR_9R_{10}$ include -$O-(CH_2) C(O)-(CH_2)N(CH_3)_2$,-$O-C(O)-(CH_2)$ (1-pyrrolidine), -$O-(CH_2) C(O)-(1-piperidine)$, -$O-(CH_2)_2C(O)-(CH_2)_2$(1-N-methylpiperazine), -$O-(CH_2) C(O)-(CH_2)_2$(4-morpholine) , -$O-(CH_2) C(O)-(CH_2)_3$(cyclohexylamine), -$O-(CH_2)_2C(O)-(CH_2)_3$(t-butylamine), -$O-(CH_2)C(O)-(CH_2)_2$(1-Phenylethylamine) , -$O-(CH_2) C(O)-(CH_2)_2$ (aniline), -O-(CH$_2$)C(O)-(CH$_2$)(L-phenylalanine ethyl ester) and -O-(CH$_2$)$_2$nC(O)-(CH$_2$)$_3$ (3-pyridylamine).

Examples of -N(R$_9$)(CH$_2$)$_n$C(O)-(CH$_2$)$_n$R$_{10}$ include -N(CH$_3$) C(O)-(CH$_3$), -N(H) (CH$_2$)$_2$C(O)-(CH$_2$) (phenyl), -N(H) (CH$_2$)C(O)-(CH$_2$)$_2$(3-pyridyl) and -N(CH$_3$) (CH$_2$)$_3$C (O)-(CH$_2$) (CH$_3$).

Examples of -N(R$_9$)-(CH$_2$)$_n$C(O)O-(CH$_2$)$_n$R$_{10}$ include -N(H)-(CH$_2$)C(O)O-(CH$_3$), -N(H)-(CH$_2$)$_2$C(O)O-(CH$_2$) (benzyl), -N(H)-(CH$_2$)$_2$-C(O)O-(CH$_2$) (3-pyridyl) and -N(CH$_3$)-(CH$_2$)C(O)O-(CH$_2$)$_2$(t-butyl).

Examples of -N(R$_9$) (CH$_2$)$_n$C(O)-(CH$_2$)$_n$NR$_9$R$_{10}$ include -N(H) (CH$_2$)C(O)-(CH$_2$)N(CH$_3$)$_2$, -N(H)C(O)-(CH$_2$) (1-pyrrolidine), -N(H) (CH$_2$)$_2$C(O)-(CH$_2$)$_2$(1-piperidine), and -N(CH$_3$) (CH$_2$) C(O)-(CH$_2$)$_2$ (4-morpholine).

Examples of -O-(CH$_2$)$_n$phenyl include 2-(4-trifluoromethylphenyl)ethoxy, 4-chlorophenoxy, 4-fluorophenylmethoxy, 3-(4-methoxyphenyl)propoxy, 4-(2-methyl-4-fluorophenyl)butoxy, 2-(2-methoxyphenyl) ethoxy, 3-methoxyphenylmethoxy, 4-carbomethoxyphenylmethoxy, 2-(3,4-dichlorophenyl) ethoxy, 4-ethoxyphenylmethoxy, 3-(4-nitrophenyl)propoxy, 4-t-butylphenylmethoxy, 4-benzyloxyphenylmethoxy and 2-(3-triflouromethylphenyl)ethoxy.

Examples of -O-(CH$_2$)$_n$pyridine include 2-pyridyloxy, 3-pyridylmethoxy and 2-(4-pyridyl)ethoxy.

Examples of -O(CH$_2$)$_n$C(O)-(CH$_2$)$_n$pyridine include -O(CH$_2$)C(O)-(CH$_2$) (2-pyridine), -O(CH$_2$)$_3$C(O)-(CH$_2$) (3-pyridine) and -O(CH$_2$)$_2$C(O)-(CH$_2$)$_3$(4-pyridine)

Examples of -O-(CH$_2$)$_n$C(O)O-(CH$_2$)$_n$pyridine include -O(CH$_2$)C(O)O-(CH$_2$) (2-pyridine), -O(CH$_2$)$_3$C(O)O-(CH$_2$) (3-pyridine) and -O(CH$_2$)$_2$C(O) O-(CH$_2$)$_3$(4-pyridine).

Examples of -O(CH$_2$)$_n$C(O)-N(R$_9$)(CH$_2$)$_n$pyridine include -O(CH$_2$)C(O)-N(CH$_3$) (CH$_2$) (2-pyridine), -O(CH$_2$)$_2$C(O)-N(CH$_3$) (CH$_2$) (3-pyridine) and -O(CH$_2$)C (O)-N(benzyl) (CH$_2$)$_2$(4-pyridine).

Examples of -O-(CH$_2$)$_n$quinoxalinyl include 2-quinoxalinyloxy, 2-quinoxalinylmethoxy and 2-(2-quinoxalinyl)ethoxy.

Examples of -O-(CH$_2$)$_n$quinolinyl include 2-quinolinyloxy, 2-quinolinylmethoxy and 2-(2-quinolinyl) ethoxy.

Examples of -O-(CH$_2$)$_n$pyrazinyl include 2-pyrazinyloxy, 2-pyrazinylmethoxy and 2-(2-pyrazinyl)ethoxy.

Examples of -O-(CH$_2$)$_n$naphthyl include 1-naphthyloxy, 2-naphthylmethoxy and 2-(1-naphthyl)ethoxy.

Examples of -O-(CH$_2$)$_n$C(O)-(CH$_{2,n}$)naphthyl include -O-(CH$_2$)C(O)-(CH$_2$) (1-naphthyl), -O-(CH$_2$)$_2$C(O)-(CH$_2$) (2-naphthyl), -O-C(O)-(CH$_2$) (1-naphthyl) and -O-(CH$_2$)$_2$C (O)-(CH$_2$)$_2$(2-naphthyl).

Examples of -O-(CH$_2$)$_n$C(O)O-(CH$_2$)$_n$naphthyl include -O-(CH$_2$)C(O)O-(CH$_2$) (1-naphthyl), -O-(CH$_2$)$_2$C(O) O-(CH$_2$) (2-naphthyl), -O-C(O)O-(CH$_2$) (1-naphthyl) and -O-(CH$_2$)$_2$C(O)O-(CH$_2$)$_2$(2-naphthyl).

Examples of -O-(CH$_2$)$_n$C(O)NR$_9$-(CH$_2$)$_n$naphthyl include -O-(CH$_2$)C(O)N(H) (CH$_2$) (1-naphthyl), -O-(CH$_2$) C(O)N(CH$_3$) (CH$_2$)$_2$(2-naphthyl) and -O-(CH$_2$)C(O)N (benzyl) (CH$_2$)$_3$(1-naphthyl).

Examples of -(CH$_2$)$_q$-OH include hydroxymethyl, hydroxyethyl and hydroxybutyl.

Examples of (CH$_2$)$_q$OC(O)R$_9$ include (CH$_2$)OC(O) methyl, (CH$_2$)$_2$OC(O)ethyl, (CH$_2$)$_3$OC(O)phenyl, (CH$_2$)$_4$OC(O) (3-pyridyl) and (CH$_2$)OC(O)thiophene.

Examples of -(CH$_2$)$_q$OC(O)-NR$_9$R$_{10}$ include -(CH$_2$) OC(O)-N(CH$_2$)$_2$, -(CH$_2$)$_2$OC(O)-N (ethyl)$_2$, -(CH$_2$)$_3$OC(O) -(1-pyrrolidine), -(CH$_2$)$_4$OC(O)-(1-piperidine) and -(CH$_2$) OC(O)-N-benzylamine.

Examples of -(1-cyclohexyl-1H-tetrazol-5-yl)C$_1$–C$_4$ alkoxy, -[1-(C$_1$–C$_5$alkyl)-1H-tetrazol-5-yl]C$_1$–C$_4$ alkoxy include -(1-cyclohexyl-1H-tetrazol-5-yl)methoxy, -(1-cyclohexyl-1H-tetrazol-5-yl)ethoxy, -[1-(methyl)-1H-tetrazol-5-yl]methoxy, -[1-(cyclopropyl)-1H-tetrazol-5-yl] ethoxy,-[1-(1-tert-butyl)-1H-tetrazol-5-yl]propoxy and -[1-(cyclopenyl)-1H-tetrazol-5-yl]methoxy.

Examples of -[1-(phenyl)-1H-tetrazol-5-yl]C$_1$–C$_4$ alkoxy (wherein phenyl is optionally substituted with one, 2 or 3 C$_1$–C$_4$ alkyl, C$_1$–C$_4$ alkoxy, halo or trifluoromethyl) include -[1-(phenyl)-1H-tetrazol-5-yl]methoxy, -[1-(phenyl)-1H-tetrazol-5-yl]ethoxy, -[1-(4-methoxyphenyl)-1H-tetrazol-5-yl]methoxy, -[1-(4-fluorophenyl)-1H-tetrazol-5-yl]propoxy.

Examples of -[1-(pyridinyl)-1H-tetrazol-5-yl]C$_1$–C$_4$ alkoxy or -[1-(1-phenylethyl)-1H-tetrazol-5-yl]C$_1$–C$_4$ alkoxy include -[1-(2-pyridinyl)-1H-tetrazol-5-yl]methoxy, -[1-(3-pyridinyl)-1H-tetrazol-5-yl]ethoxy, -[1-(4-pyridinyl)-1H-tetrazol-5-yl]propoxy, -[1-(1-phenylethyl)-1H-tetrazol-5-yl]methoxy, -[1-(1-phenylethyl)-1H-tetrazol-5-yl]ethoxy.

Examples of -(CH$_2$)$_n$-1-(C$_1$–C$_4$alkyl)-1H-5-tetrazole include -CH$_2$-1-methyl-1H-5-tetrazole, 1-methyl-1H-5-tetrazole, and -(CH$_2$)$_2$-1-methyl-1H-5-tetrazole.

Examples of -(CH$_2$)$_n$-pyrimidine include -CH$_2$-pyrimidine, -(CH$_2$)$_2$-pyrimidine, pyrimidine.

Examples of -(CH$_2$)$_n$-2-benzoxazole include -(CH$_2$)-2-benzoxazole, -(CH$_2$)$_2$-2-benzoxazole, and 2-benzoxazole.

Examples of -(CH$_2$)$_n$-2-benzothiazole include -(CH$_2$)-2-benzothiazole, -(CH$_2$)$_2$-2-benzothiazole, and 2-benzothiazole.

Examples of -(CH$_2$)$_n$-(C$_1$–C$_4$alkyl)-triazole include -(CH$_2$)-methyl-triazole, -(CH$_2$)$_2$-methyl-triazole, and -methyl-triazole. Examples of -(CH$_2$)$_n$-(C$_1$–C$_4$alkyl)-imidazole include -(CH$_2$)-methyl-imidazole, -(CH$_2$)$_2$-methyl-imidazole, and -methylimidazole.

Examples of -O-(CH$_2$)$_p$-O-(CH$_2$)$_p$-OR$_{15}$ include -O-(CH$_2$)$_2$-O-(CH$_2$)$_2$-O-benzyl, -O-(CH$_2$)$_2$-O-(CH$_2$)$_2$-O-methyl, -O-(CH$_2$)$_2$-O-(CH$_2$)$_2$-O-phenyl, and -O-(CH$_2$)$_2$-O-(CH$_2$)$_2$-O-pyridinyl.

Examples of -O-(CH$_2$)$_p$-S-R$_{15}$ include -O-(CH$_2$)$_2$-S-1-methyl-1H-5-tetatrazole, -O-(CH$_2$)$_2$ -S-pyrimidine, -O-(CH$_2$)$_2$ -S-pyridine, -O-(CH$_2$)$_2$-S-benzyl.

Examples of -O-(CH$_2$)$_p$-O-(CH$_2$)$_p$NR$_9$R$_{10}$ include -O-(CH$_2$)$_2$ -O-(CH$_2$)$_2$-1-piperidine, -O-(CH$_2$)$_2$-O-(CH$_2$)$_2$-4-methyl-1-piperazine, -O-(CH$_2$)$_2$-O-(CH$_2$)$_2$-diethylamine, and -O-(CH$_2$)$_2$-O-(CH$_2$)$_2$-4-pyridinyl-1-piperazine.

Examples of -O-(CH$_2$)$_p$-S-(CH$_2$)$_p$NR$_9$R$_{10}$ include -O-(CH$_2$)$_2$-S-(CH$_2$)$_2$-1-piperidine, -O-(OH$_2$)$_2$-S-(OR$_2$)$_2$-4-methyl-1-piperazine, -O-(CH$_2$)$_2$-S-(CH$_2$)$_2$-diethylamine, -O-(CH$_2$)$_2$-S-(CH$_2$)$_2$-4-pyridinyl-1-piperazine.

Examples of -O-(CH$_2$)$_p$-S-(CH$_2$)$_p$-OR$_{15}$ include -O-(CH$_2$)$_2$-S-(CH$_2$)$_2$-O-benzyl, -O-(CH$_2$)$_2$-S-(CH$_2$)$_2$-O-methyl, -O-(CH$_2$)$_2$-S-(CH$_2$)$_2$-O-phenyl, -O-(CH$_2$)$_2$-S-(CH$_2$)$_2$-O-pyridinyl.

Examples of -O-(CH$_2$)$_p$-S(O)-R$_{15}$ include -O-(CH$_2$)$_2$-S (O)-1-methyl-1H-5-tetatrazole, -O-(CH$_2$)$_2$-S(O)-pyrimidine, -O-(CH$_2$)$_2$-S(O)-pyridine, and -O-(CH$_2$)$_2$-S(O)-benzyl.

Examples of -O-(CH$_2$)$_p$-S(O$_2$)-R$_{15}$ include -O-(CH$_2$)$_2$-S (O$_2$)-1-methyl-1H-5-tetatrazole, -O-(CH$_2$)$_2$-S(O$_2$)-pyrimidine, -O-(CH$_2$)$_2$-S(O$_2$)-pyridine, and -O-(CH$_2$)$_2$-S (O$_2$)-benzyl.

Examples of -O-(CH$_2$)$_p$-S(O)-(CH$_2$)$_p$NR$_9$R$_{10}$ include -O-(CH$_2$)$_2$-S(O)-(CH$_2$)$_2$-1-piperidine, -O-(CH$_2$)$_2$-S(O)-(CH$_2$)$_2$-4-methyl-$_1$-piperazine, -O-(CH$_2$)$_2$-S(O)-(CH$_2$)$_2$-diethylamine, and -O-(CH$_2$)$_2$-S(O)-(CH$_2$)$_2$-4-pyridinyl-1-piperazine.

Examples of -O-(CH$_2$)$_p$-S(O)-(CH$_2$)$_p$-OR$_{15}$ include -O-(CH$_2$)$_2$-S(O)-(CH$_2$)$_2$-O-benzyl, -O-(CH$_2$)$_2$-S(O)-(CH$_2$)$_2$-O- methyl, -O-$(CH_2)_2$-S(O)-$(CH_2)_2$-O-phenyl, and -O-$(CH_2)_2$-S(O)-$(CH_2)_2$-O-pyridinyl.

Examples of -O-$(CH_2)_p$-S($O_2$)-$(CH_2)_p$$NR_9R_{10}$ include -O-$(CH_2)_2$, -S($O_2$)-$(CH_2)_2$-1-piperidine, -O-$(CH_2)_2$-S($O_2$)-$(CH_2)_2$-4-methyl-1-piperazine, -O-$(CH_2)_2$-S($O_2$)-$(CH_2)_2$-diethylamine, and -O-$(CH_2)_2$-S($O_2$)-$(CH_2)_2$-4-pyridinyl-1-piperazine.

Examples of -O-$(CH_2)_p$-S($O_2$)-$(CH_2)_p$-$OR_{15}$ include -O-$(CH_2)_2$-S($O_2$)-$(CH_2)_2$-O-benzyl, -O-$(CH_2)_2$-S($O_2$)-$(CH_2)_2$-O-methyl, -O-$(CH_2)_2$-S($O_2$)-$(CH_2)_2$-O-phenyl, and -O-$(CH_2)_2$-S($O_2$)-$(CH_2)_2$-O-pyridinyl.

Examples of -O-$(CH_2)_p$-[4-[$(CH_2)_p$$OR_{15}$]-1-piperazine] include -O-$(CH_2)_2$-[4-[$(CH_2)_2$OH]-1-piperazine], -O-$(CH_2)_2$-[4-[$(CH_2)_2$Obenzyl]-1-piperazine], and -O-$(CH_2)_2$-[4-[$(CH_2)_2$-Opyridinylmethyl]-1-piperazine].

Examples of -O-$(CH_2)_p$-[4-(CH) (phenyl)$_2$-1-piperazine] include -O-$(CH_2)_2$-[4-(CH) (phenyl) (p-chlorophenyl)-1-piperazine], -O-$(CH_2)_2$-[4-(CH)(phenyl)$_2$-1-piperazine], and -O-$(CH_2)_2$-[4-(CH)(p-fluorophenyl)$_2$-1-piperazine].

Examples of -O-$(CH_2)_p$-[4-$(CH_2)_q$phenyl-1-piperazine] include -O-$(CH_2)_2$-[4-$(CH_2)$phenyl-1-piperazine], -O-$(CH_2)_2$-[4-$(CH_2)_2$phenyl-1-piperazine], and -O-$(CH_2)_2$-[4-$(CH_2)$-m-trifluoromethylphenyl-1-piperazine].

Examples of -O-$(CH_2)_p$-[4-$(CH_2)_q$pyridinyl-1-piperazine] include -O-$(CH_2)_2$-[4-$(CH_2)$pyridinyl-1-piperazine], and -O-$(CH_2)_2$-[4-$(CH_2)_2$pyridinyl-1-piperazine].

Examples of -O-$(CH_2)_p$-[4-($NR_9R_{10}$ substituted pyridinyl)-1-piperazine] include -O-$(CH_2)_2$[4-(3-ethylamino-2-pyridinyl)-1-piperazine, -O-$(CH_2)_2$-[4-(3-piperidinyl-2-pyridinyl)-1-and piperazine, -O-$(CH_2)_2$-[4-(3-amino-2-pyridinyl)-1-piperazine.

Examples of -O-$(CH_2)_p$-(OH substituted 1-piperidine) include -O-$(CH_2)_2$-(4-hydroxy-1-piperidine) and -O-$(CH_2)_2$-(3-hydroxy-1-piperidine).

Examples of -O-$(CH_2)_p$-1-pyrrolidin-2-one include -O-$(CH_2)_2$-1-pyrrolidin-2-one and -O-$(CH_2)_3$-1-pyrrolidin-2-one.

Examples of optionally substituted piperazines include 2-hydroxymethyl4methyl-1-piperazine, 2-carboxy-4-phenyl-1-piperazine, 2-methoxy-1-piperazine, 3-methyl-4-phenyl-1-piperazine, and 2-carbomethoxy-4-methyl-1-piperazine.

The tertiary amines and aromatic heterocyclic amines of the subject specification and claims include the N-oxides thereof.

Pharmaceutically acceptable salts means salts useful for administering the compounds of this invention and include mesylate, hydrochloride, hydrobromide, hydroiodide, sulfate, phosphate, acetate, propionate, lactate, maleate malate, succinate, tartrate, and the like. These salts may be in hydrated form.

The compounds of Formula I are all characterized by pronounced antiatherogenic activity, rendering these compounds useful in the treatment and prophylaxis of atherosclerosis.

Various compounds including 2-(4-morpholinyl) -4H-benzopyran-4-one (Cpd#2),2-(4-morpholinyl)-4H -1,3-benzoxazin-4-one (Cpd #98), 8-methyl-2-(4-morpholinyl)-4H-1,3-benzoxazin-4-one (Cpd #84),2-(1-(4-thiomorpholinyl)) -4H-1,3-benzoxazin-4-one (Cpd #95) and 2-(4-methyl-1-piperazinyl) -4H-1,3-benzoxazin-4-one (Cpd #96) reduced arterial cholesterol accumulation in the SEA Japanese quail model. The reduction in arterial cholesterol was accompanied with reduced serum cholesterol levels with Compounds 84 and 95, but not with Compounds 2, 98 and 96. In normal cholesterolemic SEA Japanese quail, Compound 84 also lowered serum cholesterol. For a description of the Japanese quail model, see Day, C. E. et al., "Utility of a Selected Line (SEA) of the Japanese Quail (Coturnic Coturnix japonica) for the Discovery of New Anti-Atherosclerosis Drugs", Laboratory Animal Science 27:817–821 (1977).

Preferred antiatherosclerotic compounds include Compounds 2, 3, 14, 19, 28, 51, 72, 76, 84, 95, 96, 98, 112, 128, 139, 163, 164, 171, 188, 204, 208, 233, 266, 283, 293, 304, 326, 332 and 347.

In addition, various compounds of Formula I are also potent inhibitors of cell proliferation and are contemplated as useful in the treatment of proliferative diseases such as cancer, rheumatoid arthritis, psoriasis, pulmonary fibrosis, scleroderma, cirrhosis of the liver and for the improved utilization of artificial prosthetic devices such as arterial grafts. These agents may also be useful in the prevention or treatment of obstruction or restenosis of arteries by subsequent administration of drug in cases such as by-pass surgery, coronary by-pass surgery, balloon angioplasty (and other procedures directed at re-establishing patency in occluded or partly occluded vessels, i.e atherectomy, laser or ultrasonic procedures), transplants, and post-thrombotic restenosis.

Compounds of Formula I which are inhibitors of cell proliferation are those active in the test procedure described in Pledger W. J., Stiles C. D., Antniades H. N., Scher C. D., [Proc. Natl. Acad. Sci (USA) (1977). Examples of inhibitors of cell proliferation include Compounds 1–14; 16–17; 19–23; 25 and 26; 28; 30–34; 36–39; 42; 46–48; 51, 52; 54–56; 58–76; 81, 100–103; 105–112; 120–122; 125–133; 135–145; 149; 155 and 156; 158–160; 163; 165 and 166; 171; 173–180, 183–190, 193, 204, 206, 207, 208, 209, 211–213, 216–219, 221–226, 229, 230, 232–238, 346, 348–352.

In addition, various compounds of Formula I are also inhibitors of ADP induced platelet aggregation and are useful in the prevention or treatment of thrombotic diseases and related complications by, for example, inhibition or reversal of platelet aggregation, or platelet adhesion or blood coagulation.

Compounds of Formula I which are inhibitors of platelet aggregation are those active in the test procedure described in Born, G. R., Cross M. J., J. Physiol., 168, p. 178 (1963). Examples of inhibitiors of ADP induced platelet aggreation include: Compounds 2–3, 5–6, 9–11, 13, 20–22, 25–26, 28, 31–32, 34, 36–39, 31, 36–38, 51–53, 56, 58–59, 63, 65, 69, 72–76, 80, 100, 102, 104, 106–107, 109–113, 115, 116, 118, 120–123, 125–131, 133, 136–140, 147, 149, 154–160, 162–167, 169, 171, 172, 178, 181–188, 192–198, 207, 208–217, 219, 223, 239–241, 245–248, 250, 253–255, 257–263, 265, 266, 268–273, 275–282, 285–291, 293–296, 298–303, 308–310, 312, 314–331, 333–346, 347, 348–349, 351, and 352.

Several of these compounds, including compounds 239, 240, 340, 343, 344, 345 and 347, have been found to significantly inhibit platelet thrombus formation in a canine model of platelet-dependent coronary thrombus formation. Shebuski, R. J., Ramjit, D. R., Bencen, G. H. and Polokoff, M. A. J. Biol. Chem. 264:21550, 1989. Compound 239 accelerates the rate of thrombolysis and prevents reocclusion following successful thrombolysis in a canine model of coronary thrombosis. Shebuski, R. J., Stabilito L J., Sitko, G. R., and Polokoff, M. H., Circulation 82:169–177, 1990.

In addition, various compounds of Formula I are also potent vasodilators and are useful in the treatment of hypertension, peripheral vascular disease, vascular complications of diabetes and tissue ischemia due to poor blood flow or poor oxygen delivery. Compounds of Formula I which are vasodilators are those active in the test procedure described in Papadopoulos S. M., Gilbert B. A., Webb R. C., D'Amato C. J. [Neurosurgery 26:2605–2608 (1990)] using phenylephrine and other constricting agents in addition to endothelin. Examples of inhibitors of vasoconstrictors include compounds 51, 112, 125, 127, 128, 139, 163–165, 194, 208—210, 212, 213, 215, 223–225, 227, 231–234, 237, 243, 250, 254, 255, 257, 259, 263, 268, 269, 271, 278, 279, 281–283, 285, 347–349.

Accordingly, in using compounds of Formula I for the prevention or treatment of atherosclerotic disease or thrombotic diseases, an oral route of administration, either by conventional oral dosage forms or by mixture with food, represents the preferred method of their systemic administration. Alternatively, however, these compounds may be administered by other convenient routes of administration whereby systemic activity is obtained. These other routes of administration would include rectal, vaginal, subcutaneous, intramuscular, intravenous, and like routes.

In using compounds of Formula I for use in angioplasty, an oral route of administration represents the preferred method of their systemic administration. Alternatively, however, these compounds may be administered by other convenient routes of administration whereby systemic activity is obtained.

The patient or animal being treated must be given periodic doses of the drug in amounts effective to reduce serum and/or arterial cholesterol, and reduce arterial atherosclerotic lesion size (as determined by angiogram, ultrasound, NMR, etc.); or, by the inhibition or reversal of platelet aggregation, platelet adhesion or blood coagulation; or, by preventing arterial occlusion in vascular trauma associated with procedures such as by-pass grafts, coronary by-passes, angioplasty, post-thrombotic re-stenosis and transplants.

Such effective dosages are readily determined by methods known in the art. For example, small daily doses of the drug (e.g., 0.01–200 mg/kg) may be administered initially with higher succeeding doses until levels of serum and/or arterial cholesterol are favorably affected. By this regimen, a compound of Formula I is administered initially at doses as low as about 0.01 mg/kg per patient per day, with increasing doses up to about 200 mg/kg per patient per day. In the event the antiatherogenic response in a patient being treated at a dose of 200 mg/kg per day is insufficient, higher doses are also utilized to the extent patient tolerance permits further increases in dose.

While the preferred dosage regimen is with single daily dosing of patients, also preferred for obtaining more uniform serum levels of drug are multiple dosages per day (e.g., up to 4–6 times daily). Accordingly, when 4 daily doses of drug are to be administered, each such dose may be about 50 mg/kg per patient per dose, or higher depending on tolerance.

Similar doses are employed in non-human mammals, e.g. 0.01–200 mg/kg/day.

Charts A–L herein describe various methods by which the compounds of Formula I are prepared. With respect to these Charts, X, Y, $R_5$, $R_6$, $R_7$, $R_8$, $R_9$ and $R_{10}$ are as defined above.

With respect to Chart A, the compounds of Formula I are prepared by mixing the salicylic acid ester with the morpholine ynamine neat, or in an organic solvent, with stirring. After several minutes, a tertiary amine base, e.g. TEA (triethylamine), is added and the reaction stirred for a period of time. The product can be isolated by recrystallization or column chromatography.

With respect to Chart B, the compounds of Formula I are prepared by reaction of a ortho-hydroxyacetophenone with an amideacetal, e.g., N,N-dimethylformamide dimethylacetal, to yield a vinylogous amide. Treatment of that amide with a halogen (Br, Cl, I or F) in an organic solvent such as $CHCl_3$ or CHCN then affords a 3-halochromone. Treatment of that halochromone with amines, either neat or in the presence of organic solvents, then yields the desired 2-aminochromone. With respect to Chart C, the compounds of Formula I are prepared by treating a ortho-hydroxyacetophenone with carbon disulfide in the presence of base followed by treatment with acid which yields the 2-mercaptochromone. Treatment of the resulting mercaptan with the appropriate amine then affords the desired 2-aminochromone.

With respect to Chart D, the compounds of Formula I are prepared by hydrogenation of the corresponding benzylmethoxy analogues which are prepared by the methods described in Charts A,B and C, followed by alkylation of the resulting phenol.

With respect to Chart E, these compounds can be prepared by treatment of a o-hydroxy acetophenone with an iminium salt such as morpholine-4-phosgene iminium chloride, in the presence of boron trifluoride etherate. Subsequent hydrolysis and alkylation yields the desired compounds.

With respect to Chart F, these compounds can be prepared by the treatment of an o-hydroxy acetophenone containing a trifluoromethyl sulfonate group with an iminium salt such as 4-morpholine dichloromethyleniminium chloride, in the presence of boron trifluoride etherate. Subsequent hydrolysis and alkylation yields the 2-aminochromone. Treatment of the 2-aminochromone with an acetylene in the presence of a palladium catalyst such as (bis)triphenylphosphine palladium dichloride and copper iodide yields a 2-aminochromone with a substituted acetylene. Hydrogenation of the acetylene yields the desired derivative.

With respect to Chart G, the treatment of an o-hydroxy acetophenone containing a halogen group with an iminium salt such as 4-morpholine dichloromethyleniminium chloride, in the presence of boron trifluoride etherate. Subsequent hydrolysis and alkylation yields the 2-aminochromone. Treatment of the 2-aminochromone with a tetraalkyl tin reagent in the presence of a palladium catalyst such as (bis)triphenylphosphine palladium dichloride and a salt such as lithium chloride affords a 2-aminochromone substituted with an alkyl substituent.

With respect to Chart I, the compounds of formula I are prepared by treating 4-benzyloxy-2-hydroxy-3-methylacetophenone with sodium hydride, then ethyl α-methylthioacetate and finally acid to yield 7-benzyloxy-8-methyl-2-methylthiomethyl-4H -[1]-benzopyran-4-one. Treatment of that compound with methyl iodide affords the corresponding 7-benzyloxy-8-methyl-2-iodomethyl -4H-[1] -benzopyran-4-one. Treatment of that compound with the appropriate amine then afforded the compounds of formula I. Compounds of formula I were also prepared by treating a formula I compound such as 7-benzyloxy-8-methyl-2-(4-morpholiniylmethyl)-4H-[1]-benzopyran-4-one with a transition metal catalyst in an atmosphere of hydrogen to yield 7-hydroxy-8-methyl-2-(4-morpholiniylmethyl)-4H-[1]-benzopyran-4-one. Alkylation of that phenol with the appropriate group also afforded compounds of formula I.

Alternatively, compounds of formula I can also be prepared by hydrogenation of a $R_{5-8}$ benzyloxy2-amino-4H-1-benzopyran-4-one followed by alkylation of the resulting phenol as illustrated in chart H.

With respect to Chart J, these compounds are prepared by initial alkylation of the appropriate 2-aminochromone phenol (e.g. prepared according to the methods of Charts D or E) with 1,2-dibromoethane under phase transfer catalysis. Direct substitution of the bromine with an appropriate amine nucleophile affords the 2-aminochromone with a 2-aminoethyloxy substitutent.

With respect to Chart K, these compounds are prepared by treatment of a O-hydroxyacetophenone with potassium t-butoxide and an α-amino acetate, such as methy-2-(4-morpholinyl)-acetate, followed by acidification of the initial adduct.

With respect to Chart L, a procedure for the preparation of 2-aminochromones is contemplated in which a salicylic ester is treated with the anion of an acetyl amine (such as from lithium diisopropyl amide deprotonation of acetyl-4-morpholine) to afford an initial β-ketoamide. This compound, upon cyclodehydration with a reagent such as polyphosphoric ester, would give the 2-aminochromone.

The synthesis of the compounds of the present invention is more completely understood by the following examples:

Procedure 1: Preparation of 1-ethynyl morpholine.

Part A: Preparation of trichloroacetylmorpholine.

Morpholine (4.0 mL, 45 mmol) is dissolved in EtOAc (50 mL) and saturated K2CO3 (40 mL) added. The mixture is cooled in an ice bath and trichloroacetyl chloride (5.0 mL, 45 mmol) added drop-wise. The reaction is stirred for 20 min then diluted with EtOAc (200 mL) and washed with aq. K2CO3 (20 mL), water (2×50 mL) and brine (30 mL). The organic layer is dried over MgSO4. Rotary evaporation gives trichloroacetylmorpholine.

Mp=80°–1° C.

1H NMR (300 MHz, CDCl$_3$) 3.81-3.76 (m)

UV (EtOH) 224 (4.520)

IR (mull) 2955, 2926, 2859, 1657, 1431, 1270, 1239, 1116, 962, 852, 848, 842, 810, 777.

MS m/e (relative intensity) 233 (12), 231 (12), 115 (8), 114 (100), 86 (10), 70 (67), 56 (26), 42 (20), 28 (18), 27 (8)

HRMS calc'd. for C6H8NO2Cl3: 230.9621; found: 230.9629; anal. calc'd. for C6H8NO2Cl3: C, 31.00, H, 3.47, N, 6.02, Cl, 45.75;

FOUND: C, 31.15, H, 3.43, N, 6.07, Cl, 45.88.

Part B: Preparation of tricholorvinylmorpholine.

Trichloroacetylmorpholine (8.3 g, 36 mmol) is dissolved in toluene and triphenylphosphine (9.44 g, 36 mmol) added. The mixture is brought to reflux for 1.5 h, then cooled and solvent removed in vacuo. The residue is fractionally distilled at reduced pressure to give trichlorovinylmorpholine. BP=85–7 ° C., 20 mm Hg.

Part C: Preparation of the morpholine ynamine.

Trichlorovinylmorpholine (5.50 g, 24.5 mmol) is dissolved in anhydrous ether (30 mL) under a nitrogen atmosphere. The mixture is cooled to –30° C. and butyllithium (50 mL, 1.5 M, 75 mmol) added slowly, then the mixture is allowed to warm to 23° C. for 2 h. The mixture is cooled to –30 ° C. again and poured into cold 20% ammonium hydroxide (20 mL), ether (50 mL) added and the solutions quickly separated. The organic layer is filtered through anhydrous K2CO3 (5 cm) and concentrated in vacuo to a yellow orange oil that is fractionally distilled (0.9 mm Hg, BP=53° C.) to give the ynamine, 1-ethynyl morpholine, as a colorless oil (1.1 g, 40%).

IR (film) 2970, 2940, 2870, 2137, 1647, 1458, 1382, 1272, 1123 cm$^{-1}$. $^1$H-NMR (CDCl$_3$, δ) 3.81, 3.12, 2.36.

EXAMPLE 1

Preparation of 6-chloro-2-(4-morpholinyl)-4H-1-benzopyran-4-one, Compound 1

The methyl ester of 5-chlorosalicylic acid (2.00 g, 10.7 mmol) is mixed with ethynyl morpholine (neat, 1.00 g, 9.00 mmol) dropwise. The reaction is exothermic. When the mixture cools, triethylamine (TEA, 1 drop) is added and the liquid mixture immediately crystallized. The mixture is chromatographed (flash, SiO$_2$, CH$_2$Cl$_2$/EtOH, 95:5) to yield 6-chloro-2-(4-morpholinyl)-4H-1benzopyran-4-one (1.07 g, 45%). Mp 194°–5° C.; IR (mull) 2949, 2946, 2869, 2855, 1640, 1615, 1566, 1464, 1450, 1437, 1345, 1246, 1118, 822, 787 cm$^{-1}$; 1H-NMR (CDCl$_3$, 200 MHz, δ) 8.11 (d, J=2.5 Hz, 1H), 7.49 (dd, J=8.7, 2.5 Hz, 1 H), 7.23 (d, J=8.7 Hz, 1H), 5.49 (s, 1H), 3.85-3.82 (m, 4 H), 3.53-3.50 (m, 4 H); UV (EtOH) λ max (ε) 217 (31,360), 230 (24,900), 245 sh (12,100), 2908 h (11,170), 301 (15,810) , 315 (16,070); Mass Spectrum: ions at m/e (relative intensity) 267 (35), 265 (100), 210 (24) 209 (22), 208 (74), 207 (31), 180 (47), 154 (27), 126 (19), 52 (21); High resolution MS calc'd. for C$_{13}$H$_{12}$NO$_3$Cl: 265.0506. Found: 265.0512. Anal. calc'd. for C$_{13}$H$_{14}$NO$_3$Cl: C, 58.77; H, 4.55; N, 5.27; Cl, 13.34. Found: C, 58.52; H, 4.66; N, 5.11; Cl, 13.58.

Following the general procedure of Example 1, but employing the appropriate o-hydroxy salicylic methyl ester in place of the methyl ester of 5-chlorosalicylic acid and, depending upon the reactivity of the methyl ester, carried out either neat, in methylene chloride, toluene or triethylamine, there are prepared the following products:

Cpd 2 2-(4-morpholinyl)-4H-1-benzopyran-4-one, Mp 160°–61° C.;

Cpd 4 7-Chloro-2-(4-morpholinyl)-4H-1-benzopyran-4-one, Mp 160°–1° C. (from CH$_2$Cl$_2$/EtOH);

Cpd 5 8-Chloro-2-(4-morpholinyl)-4H-1-benzopyran-4-one, Mp 190°–1° C. (from CH$_2$C1$_2$/Et$_2$O);

Cpd 6 6-Bromo-2-(4-morpholinyl)-4H-1-benzopyran-4-one, Mp 164°–5° C. (from CH$_2$Cl$_2$/Et$_2$O);

Cpd 7 6-Fluoro-2-(4-morpholinyl)-4H-1-benzopyran-4-one, Mp 198°–9° C. (from CH$_2$Cl$_2$/Et$_2$O);

Cpd 8 6-Methyl-2-(4-morpholinyl)-4H-1-benzopyran-4-one, Mp 166°–7° C. (from CH$_2$Cl$_2$/Et$_2$O);

Cpd 9 7-Methyl-2-(4-morpholinyl)-4H-1-benzopyran-4-one, Mp 163°–4° C. (from CH$_2$Cl$_2$/Et$_2$O);

Cpd 10 8-Methyl-2-(4-morpholinyl)-4H-1-benzopyran-4-one, Mp 169°–70° C. (from EtOAc/hexane);

Cpd 11 6-Methoxy-2-(4-morpholinyl)-4H-1-benzopyran-4-one, Mp 148°–9° C. (from EtOH/CH$_2$Cl$_2$);

Cpd 12 7-Methoxy-2-(4-morpholinyl)-4H-1-benzopyran-4-one, Mp 173°–4° C. (from EtOH/hexane);

Cpd 13 6-(Phenylmethoxy)-2-(4-morpholinyl)-4H-1-benzopyran-4-one, Mp 210°–12° C.;

Cpd 14 8-(Phenylmethoxy)-2-(4-morpholinyl)-4H-1-benzopyran-4-one, Mp 192°–4° C.;

Cpd 15 [2-(4-morpholinyl)-4-oxo-4H-1-benzopyran-6-yl] -1,1-dimethylethyl carbamic acid ester;

Cpd 16 6-(3-pyridinecarboxamide)-2-(4-morpholinyl)-4H-1-benzopyran-4-one.

EXAMPLE 17

Preparation of 2-(Morpholinyl)-6-nitro-4H-1-benzopyran-4-one, Compound #17

The ethyl ester of 5-nitro salicylic acid (634 mg, 3.0 mmol) is dissolved in TEA (2.0 mL) and the morpholine ynamine added. The mixture is then stirred for 48 h. The reaction is diluted with EtOAc (200 mL) and washed with water (5×25 mL), brine (30 mL) and dried (MgSO$_4$). Evaporation of the solvent yields product which is chromatographed (silica gel [50 g]; 4% EtOH/CH$_2$Cl$_2$) to afford 182 mg (22%) of the desired product. MP=258°–9° C.; 1H NMR (CDCl$_3$, 300 MHz) 9.05 (d, J=2.9 Hz, 1H), 8.44 (dd, J=8.7, 2.9 Hz, 1H), 7.46 (d, J=9.3 Hz, 1H), 5.69 (s, 1 H), 3.91-3.86 (m, 4 H), 3.61-3.56 (m, 4 H); UV (EtOH) 226 (23,700), 234sh (19,000), 282 (17,600), 316 (15,000); LRMS m/e (rel. intensity) 277 (28), 276 (100), 261 (38), 219 (80), 218 (53), 191 (38), 172 (19), 55 (30), 53 (35), 41 (31); IR (mull) 2954, 2924, 2856, 1637, 1627, 1604, 1565, 1447, 1422, 1347, 1253, 1126, 740, 638; HRMS calc'd. for C13H12N2O5: 276.0746; found: 276.0742; anal calc'd. for C13H12N2O5: C, 56.52, H, 4.38, N, 10.14; found: C, 56.32, H, 4.52, N, 10.16.

EXAMPLE 18

Preparation of 2-(4-Morpholinyl)-4H-pyrano[2,3b] pyridin-4-one, Compound 18

The methyl ester of 2-hydroxy-3-carboxypyridine (300 mg, 1.9 mmol) is dissolved in toluene (2.0 mL) and a solution of the morpholine ynamine (250 mg, 2.2 mmol) in toluene (2.0 mL) added dropwise at 23° C. The reaction is then warmed to 100° C. for 24 h. The mixture is cooled and purified by flash chromatography (CH$_2$Cl$_2$/EtOH, 95:5) to give the chromone as pale yellow crystals (270 mg, 63 %). Mp 190°–1° C.; IR (mull) 2924, 2868, 2855, 1652, 1639, 1611, 1590, 1557, 1463, 1405, 1250, 1120, 788, 602 cm$^{-1}$, $^1$H NMR (CDCl$_3$, 200 MHz δ) 8.60 (s, 1H), 8.57 (dd, J=3.2, 2.4 Hz, 1H), 7.45 (m, 1 H), 5.56 (s, 1 H), 3.92-3.87 (m, 4 H), 3.68-3.63 (m, 4 H); UV (EtOH) λ max (ε) 215 (16,740), 243 (10,250), 281 sh (8,330), 289 (10,500), 320 (15,320); Mass spectrum: ions at m/e (relative intensity) 233 (14), 232 (100), 217 (17), 175 (37), 174 (39), 146 (15), 122 (17), 79 (34), 53 (15), 42 (14); Anal. calc'd. for C$_{12}$H$_{12}$N$_2$O$_3$: C, 62.06; H, 5.21; N, 12.06. Found: C, 61.85; H, 5.15; N, 11.88.

EXAMPLE 19

Preparation of 6-([[phenylmethoxy]carbonyl]amino) -2-(4-morpholinyl)-4H-1-benzopyran-4-one, Compound 19

2-Hydroxy-5-([[phenylmethoxy]carbonyl]amino)benzoic acid methyl ester (1.0 g, 3.3 mmol) is added to CH$_2$Cl$_2$ (1 ml) and cooled to 0° C. To that solution is added the ynamine (366 mg) neat and dropwise followed by several drops of TEA. The reaction solution turns yellow and after stirring at room temperature for 18 hr is heated at 80° C. (oil bath) for 6 hr. A solid fills the flask. The reaction is diluted with CH$_2$Cl$_2$ and the solid collected on a filter to yield 350 mg (19.4%) of the desired product. An analytical sample was prepared by recrystallization from CH$_3$CN. Mp 245°–50° C.; IR (mull) 3263, 2947, 2925, 2921, 2867, 2854, 1716, 1638, 1623, 1577, 1564, 1558, 1464, 1456, 1453, 1404, 1246, 1231, 1121, 731 cm$^{-1}$; $^1$H-NMR (CDCl$_3$, δ) 8.15 (d, 1H, J=2 Hz), 7.95 (s, 1 H), 7.87 (s, 1H), 7.3 (m, 7H), 5.42 (s, 1H, vinyl), 5.2 (s, 2H), 3.7 (m, 4H), 3.4 (m, 4H); UV (EtOH λ max (ε)231 (27,520), 246 (34,960), 300 sh (16, 300), 307 (17,830), 320 sl sh (12,800); Mass spectrum: ions at m/e (relative intensity) 380 (17), 335 (12), 272 (100), 215 (69), 187 (44), 161 (32), 108 (79), 91 (87), 79 (99), 53 (32), 44 (50);

Anal. Calc'd. for: C$_{21}$H$_{20}$N$_2$O$_5$: C, 66.31; H, 5.26; N, 7.36.

Found: C, 66.40; H, 5.28; N, 7.30.

EXAMPLE 20

Preparation of 8-Methoxy-2-(4-morpholinyl)-4H-1-benzopyran-4-one, Compound 20

Method A: 3-Methoxy salicyl chloride (750 mg, 4 mmol) is dissolved in THF (4 mL) and cooled to 0° C. The morpholine ynamine (445 mg, 4.0 mmol) is dissolved in THF (4 mL) and then added dropwise to the cooled solution of the acid chloride. A white precipitate forms immediately and after stirring for 20 minutes, TEA (0.60 mL), 4.5 mmol) is added and the reaction temperature raised to 23° C. After refluxing for 20 minutes the reaction is cooled to room temperature and the THF removed in vacuo. The crude reaction mixture is filtered and the filtrate chromatographed over silica gel (5% EtOH/CH$_2$Cl$_2$) to afford, after recrystallization, 115 mg (12%) of the desired product. Mp 184°–6° C.; IR 2952, 2925, 2870, 2855, 1642, 1625, 1618, 1581, 1575, 1463, 1455, 1410, 1350, 1250, 1244, 1116, 773 cm$^{-1}$; UV (EtOH) λ max (ε) 212 sh (20,710), 236 (25,000), 250 sh (12,000), 301 (17,800); 1H-NMR (CDCl$_3$) 7.74 (dd, 1H, J=2 and 8 Hz), 7.27 (t, 1H, J=8 Hz), 7.10 (dd, 1H, J=2 and 8 Hz), 5.52 (s, 1H), 3.96 (s, 3H), 3.88 (m, 4H), 3.55 (m, 4H); Mass spectrum: ions at m/e (relative intensity) 261 (100), 204 (63), 203 (19), 176 (27), 122 (33), 77 (26), 55 (26), 57 (32), 43 (37); Anal. calc'd. for C$_{14}$H$_{15}$NO$_4$: C, 64.35; H, 5.76; N, 5.36.

Found: C, 64.39; H, 5.83; N, 5.74.

Method B: 3-Methoxy methyl salicylate (547 mg, 3.0 mmol) is dissolved in TEA (4.0 mL) and the morpholine ynamine (400 mg, 3.7 mmol) is added. The mixture is stirred for 48 h, then diluted with EtOAc (200 mL) and washed with water (5×20 mL), brine (30 mL) and dried (MgSO$_4$). Evaporation in vacuo affords 690 mg of crude product. Chromatography (silica gel [50 g]; 4% EtOH/CH$_2$Cl$_2$) affords the desired product (160 mg; 20%).

EXAMPLE 21

Preparation of 3-Amino-2-(4-morpholinyl)-4H-1-benzopyran-4-one, Compound 21

Part A: 2-(4-morpholinyl)-4H-benzopyran-4-one (2.00 g, 8.00 mmol) is dissolved in CH$_2$Cl$_2$ (12 mL) and nitric acid (5.00 mL, 24 mmol) added dropwise with stirring at 23° C. After 2 H, the mixture is warmed to 60° C. and three drops of sulfuric acid added. The reaction gradually turns red and a brown gas is evolved. After about 4 hrs the starting material is consumed as evidenced by TLC (EtOAc/ CH$_3$OH, 9/1). The reaction mixture is poured onto ice (30 mL) and yellow crystals precipitated almost immediately. The crystals are filtered and washed with cold water. The crude product is dissolved in ethyl acetate (200 mL) and the remaining precipitate is removed by filtration. The EtOAc layer is washed with saturated NaHCO$_3$ (2×30 mL) and brine (50 mL) then dried (MgSO$_4$). Rotary evaporation yields 1.44 g (60%) of 2-(4-morpholinyl)-3-nitro-4-H-1benzopryan-4-one. The 2-(4-morpholinyl)-3-nitro-4H-1-benzopyran-4-one is further purified by column chromatography over silica gel (EtOAc) to give analytical material. Mp 206°–8° C.; IR (mull) 2954, 2925, 2869, 2856, 1646, 1620, 1599, 1575, 1487, 1467, 1445, 1435, 1422, 1379, 1341, 1325, 1116 cm$^{-1}$; $^1$H-NMR (CDCl$_3$, δ) 8.23 (dd, J=1.9, 8.9 Hz, 1H), 7.65 (ddd, J=2.1, 7.3, 10.2, 1H), 7.39 (m, 2H), 3.90 (m, 4H), 3.62 (m, 4H); MS m/e (rel intensity) 276 (78), 201 (36), 187 (38), 121 (100), 120 (56), 92 (30), 79 (23), 77 (21), 73 (22), 42 (25); UV (EtOH) λ max (ε) 230 (15,730), 286 (17,000), 295 sh (14,760), 360 sh (1,840); Anal. calc'd. for C$_{13}$H$_{12}$N$_2$O$_5$: C, 56.52; H 4.38; N, 10.14. Found: C, 56.53; H, 4.56; N, 9.79.

Part B: 2-(4-Morpholinyl)-3-nitro-4H-1-benzopyran-4-one(500 mg) is dissolved in EtOAc (30 mL). Palladium on carbon (10%, 100 mg) is added under a nitrogen atmosphere. The mixture is fixed to a Parr hydrogenator at 30 psi for 4 hr, then filtered (Celite, 1 cm) and solvent removed in vacuo. The product is purified by flash chromatography (EtOAc) to give 3-Amino-2-(morpholinyl)-4H-1-benzopyran-4-one (419 mg, 94%). Mp 140°–1° C.; IR (mull) 2954, 2925, 2856, 1621, 1607, 1551, 1466, 1423, 1382, 1277, 1271, 1240, 1115, 952, 762 cm$^{-1}$; $^1$H NMR (CDCl$_3$, δ) 8.24 (dd, J=7.8, 2.0 Hz, 1H), 7.60 (ddd, J=6.8, 6.7, 1.8 Hz, 1 H), 7.38 (br.d, J=7.8 Hz, 2 H), 3.91-3.76 (m, 4 H), 3.52-3.47 (m, 4 H), 3.43 (br.s, 2 H); UV (EtOH) λ max (ε) 212 (19,150), 233 (15,180), 255sh (9,900), 300 (3,000), 356 (12,100); Mass spectrum:ions at m/e (relative intensity) 262 (21), 246 (100), 201 (21), 188 (18), 187 (40), 148 (88), 121 (52), 114 (21), 70 (36), 42 (17); Anal. calc'd. for C$_{13}$H$_{14}$N$_2$O$_3$: C, 63.40, H, 5.73, N, 11.38; found: C, 63.48; H, 5.84; N, 11.46.

EXAMPLE 22

Preparation of 3-Chloro-2-(4-morpholinyl)-4H-1-benzopyran-4-one, Compound 22

2-(4-Morpholinyl)-4H-benzopyran-4-one (2.0 g, 8.0 mmol) is dissolved in CH$_2$Cl$_2$ (20 mL). t-Butyl hypochlorite (1.0 mL, 8.5 mmol) is added dropwise at 23° C. The reaction mixture is warmed slightly and is finished almost instantaneously. The solvent is removed in vacuo and the residue is taken up in EtOAc (200 mL). The organic layer is washed with water (2×50 mL) and brine (80 mL), then dried (MgSO$_4$). The solution is concentrated in vacuo giving colorless crystals which are recrystallized from EtOAc to give the desired product (1.86 g, 91%) Mp 127°–8° C.; IR (mull) 2962, 2923, 2856, 1635, 1612, 1597, 1562, 1555, 1466, 1457, 1325, 1233, 1119, 872, 762 cm$^{-1}$; $^1$H NMR (200 Mhz, CDCl$_3$, δ) 8.20 (br d, J=7.5 Hz, 1H), 7.60 (ddd, J=9.1, 6.7, 1.7 Hz, 1H), 7.36 (m, 2 H), 3.88 (m, 4H), 3.74 (m, 4H); MS m/e (rel intensity) 267 (33), 266 (15), 265 (100), 231 (15), 230 (98), 209 (16), 207 (45), 120 (27), 110 (19), 41 (16); UV (EtOH) λ max (ε) 214 (18,900), 238 (18,160), 300 sh (11,530); Anal. calc'd. for C$_{13}$H$_{12}$NO$_3$Cl: C, 58.76; H, 4.55; N, 5.27. Found: C, 58.82; H, 4.58; N, 5.37.

EXAMPLE 23

Preparation of 3-Bromo-2-(4-morpholinyl)-4H-1-benzopyran-4-one, Compound 23

2-(4-morpholinyl)-4H-benzopyran-4-one (2.0 g, 8.0 mmol) is dissolved in CH$_2$Cl$_2$ (20 mL). N-Bromosuccinimide (1.6 g, 8.2 mmol) is added and the reaction mixture waned slightly and the starting material disappears immediately as evidenced by TLC. The solvent is removed in vacuo and the colorless residue is taken up in EtOAc (200 mL) and washed with water (4×30 mL), brine (50 mL) and dried (MgSO$_4$). Rotary evaporation gives the desired product (2.27 g, 92%) as colorless crystals. mp: 145°–6° °; IR (mull) 3337, 3016, 2922, 2871, 2855, 1698, 1609, 1585, 1502, 1462, 1378, 1367, 1341, 1303, 1295, 1260, 1234, 996, 812 cm$^{-1}$; $^1$H NMR (CDCl$_3$, δ) 8.22 (dd, J=7.9, 1.8 Hz, 1H), 7.63 (ddd, J=8.2, 7.4, 1.4 Hz, 1H), 7.44-7.28 (m, 2H), 3.90-3.84 (m, 4H), 3.76-3.69 (m, 4H); LRMS m/e (rel intensity) 311 (55), 309 (55), 253 (14), 231 (17), 230 (100), 172 (21), 121 (20), 120 (15), 110 (61), 41 (16); UV (EtOH) λ max (ε) 216 (18,400), 238 (18,600), 317 (17,040); High resolution MS calc'd. for C$_{13}$H$_{12}$NO$_3$Br: 309.0001. Found: 308.9990. Anal. calc'd. for C$_{13}$H$_{12}$NO$_3$Br: C, 50.34; H, 3.90; N,4.52. Found: C, 50.40; H,4.05; N, 4.46.

Relating to Chart B:

EXAMPLE 24

Preparation of 8-methyl-2-(4-morpholinyl)-7-(phenylmethoxy)-4H-1-benzopyran-4-one (Cpd 24)

Part A: 3-(Dimethylamino)-1-(2-hydroxy-3-methyl-4-benzyloxyphenyl)-Propen-1-one.

2-Hydroxy-3-methyl-4-(phenylmethoxy)-acetophenone (25 g, 98 mmol) and DMF-DMA (17.9 g, 150 mmol) is heated at 95°–100° C. for 2.75 h. The reaction is cooled to room temperature and excess reagent and CH$_3$OH removed in vacuo to leave a dark solid. That solid is triturated with ether at 0° C. and filtered to yield 19.64 g (64.4%) of the product as a yellow solid. The mother liquors (9.91 g) also contained product but is not isolated. An analytical sample is prepared by recrystallization from EtOAc/Skelly-B.

Part B: 3-Bromo-8-methyl-7-(phenylmethoxy)-[4H]-1-benzopyran-4-one.

The vinylogous amide of Part A (19.0 g, 61 mmol) is dissolved in CHCl$_3$ and cooled to 0° C. Br$_2$ (9.75 g, 61 mmol), in CHCl$_3$ (50 mL), is added dropwise over a 5 minute period. After complete addition, the reaction is diluted with H$_2$O (200 mL) and vigorously stirred for 5 minutes. The CHCl$_3$ layer is separated, dried (MgSO$_4$) and solvent evaporated in vacuo to yield 23.1 g of crude product. Recrystallization from EtOAc afforded 15.2 g (66%) of analytically pure product.

Part C: 8-Methyl-2-(4-morpholinyl)-7-(phenylmethoxy)-4H-1-benzopyran-4-one.

The 3-bromochromone of Part B (1.0 g, 2.9 mmol) is dissolved in acetonitrile (35 mL). Anhydrous potassium carbonate is added (371 mg, 2.9 mmol). Then morpholine (0.252 mg, 2.9 mmol) is added dropwise. Stirring is begun and the reaction warmed to reflux for 36 h. The acetonitrile is removed in vacuo and the organic material is taken up in ethyl acetate. The organic phase is washed with water and brine then dried (MgSO$_4$). The solvent is removed in vacuo and the residue is chromatographed over silica gel (CH$_2$Cl$_2$/Et$_2$O; 2/1) to give two main fractions. The first contained a 3-amino substituted product.

The second fraction is a mixture of a ring contracted product and the desired 2-morpholinyl chromone. That mixture is rechromatographed (EtOAc/CH$_3$OH; 95/5) giving two fractions, the faster moving containing the ring-contracted product (211 mg, 21%), Mp 171°–2° C.; IR (mull) 2954, 2924, 2867, 2855, 1693, 1632, 1613 1597, 1260, 1166, 1140, 1108, 1099, 749 cm$^{-1}$; $^1$H-NMR (200 MHz, CDCl$_3$, δ) 7.64 (dd, J=8.57 Hz, 1.27, 1H), 7.49-7.41 (m, 5 H), 6.89 (s, vinyl, 1H), 8.84 (d, J=8.57 Hz, 1H), 5.22 (s, 2 H), 3.89-3.84 (m, 4 H), 3.79-3.76 (m, 4 H), 2.30 (s, 3 H); UV (EtOH) λ max (ε) 204 (25,300), 205 sh (24,500), 252 (8,550), 258 (8,670), 321 (18,900), 377 (33,100), 391 (29,300); High resolution MS calc'd. for C$_{21}$H$_{21}$NO$_4$: 351.1470. Found: 351.1470. Anal. calc'd. for C$_{21}$H$_{21}$NO$_4$: C, 71.78; H, 6.02; N, 3.99. Found: C, 71.60; H, 6.15; N, 3.96.

On further elution, the desired 2-morpholinyl chromone (Cpd #24) is isolated (127 mg, 12%). 181.5°–182.5° C.; IR (mull) 2953, 2925, 2864, 2857, 1637, 1612, 1592, 1575, 1413, 1274, 1272, 1251, 1240, 1119, 782 cm$^{-1}$; $^1$H-NMR (200 MHz, CDCl$_3$, δ) 8.00 (d, J=9.1 Hz, 1 H), 7.47-7.38 (m, 5 H) 6.98 (d, J=9.1 Hz, 1 H), 5.44 (s, 1H), 5.19 (s, 2 H), 3.89-3.84 (m, 4 H), 3.54-3.49 (m, 4 H), 2.33 (s, 3 H); UV (EtOH) λ max (ε) 217 (33,610) 239 (23,660), 291 sh (13,980), 312 (26,160), 376 (509); High resolution MS calc'd. for $C_{21}H_{21}NO_4$: 351.1470. Found: 351.1464. Anal. calc'd. for $C_{21}H_{21}NO_4$: C, 71.78; H, 6.02; N, 3.99. Found: C, 71.79; H, 5.99; N, 3.98.

EXAMPLE 25

Preparation of 2-(4-morpholinyl)-5-(phenylmethoxy)-4H-1-benzopyran-4-one Compound 25

Part A: 6-Benzyloxy-2-hydroxyacetophenone 2,6-Dihydroxyacetophenone (84.48 g, 0.55 M), benzyl bromide (95 g, 0.55 M), and $K_2CO_3$ (120 g) is added to acetone (750 mL). That mixture is heated at reflux under nitrogen with vigorous stirring (overhead stirrer) for 18 h. The reaction is then cooled to room temperature and filtered. The filtrate is evaporated in vacuo to yield an oily semi-solid. That material is dissolved in $CH_2Cl_2$ and washed with 1 N HCL. The $CH_2Cl_2$ solution is dried ($MgSO_4$) and solvent removed in vacuo to yield a pale oil. That material is chromatographed over silica gel (400 g) eluting with $CH_2Cl_2$ to afford 72.8 g (54.5%) of the product. An analytical sample is prepared by recrystallization from EtOAc/Skelly-B.

Part B: 3-(Dimethylamino)-1-(2-hydroxy-6-benzyloxyphenyl)-Propen-1-one

A mixture of 6-benzyloxy-2-hydroxyacetophenone (15.0 g, 62 mmol) and N,N-dimethylformamide dimethylacetal (DMF-DMA; 10.71 g, 90 mmol) is heated under nitrogen at 100°–10° C. for 2 h. Within several minutes of placing the reaction vessel in the oil bath (already at 100° C.) the initial heterogeneous mixture became homogeneous and very dark in color. After several additional minutes a solid began to separate from this solution and at the end of the reaction time the flask is filled with a yellow solid. The reaction is cooled to room temperature and excess DMF-DMA and methanol is removed in vacuo. The resulting solid is filtered with the aid of ether and air dried to yield 15.41 g (83.7%) of pure product. An analytical sample is prepared by recrystallization from EtOAc.

Part C: 5-Benzyloxy-3-bromo-[4H]-1-benzopyran-4-one

The vinylogous amide of Part B (10.0 g, 33.6 mmol) is dissolved in $CHCl_3$ (150 mL) and cooled to 0° C. $Br_2$ (5.38 g, 33.6 mmol) is added to the aforementioned solution in $CHCl_3$ (50 mL) dropwise over 10 minutes. After complete addition the reaction is diluted with $H_2O$ and vigorously stirred for 5 minutes. The organic layer is separated and washed with brine, dried ($MgSO_4$), and evaporated to give a dark red oil. Chromatography over silica gel (400 g)eluting with 1% $CH_3OH/CH_2Cl_2$ afforded, after recrystallization from EtOAc/Skelly-B, 4.76 g (42.8%) of the product.

The 5-benzyloxy-3-bromochromone of Part B (3.31 g, 10.0 mmol) is dissolved in acetonitrile (50 mL). Anhydrous potassium carbonate (1.38g, 10.0 mmol) is added, then morpholine (1.02 mL, 11.0 mmol) is added. The mixture is heated to reflux for 72 h. The solvent is removed under vacuo and the residue is taken up in EtOAc (400 mL) and washed with water (3×50 mL) and brine (100 mL), then dried (MgSO*4). The solvent is removed in vacuo and the residue purified by flash chromatography ($CHCl_3/CH_3OH$, 99/1) giving three main fractions. The first fraction contained a 3-morpholinyl chromone (0.92 g, 51%). Mp 122.5°–124° C.; IR (mull) 2956, 2924, 2856, 1641, 1604, 1464, 1459, 1269, 1235, 1180, 1115, 1070, 1064, 772, 699 cm$^{-1}$; $^1$H-NMR (200 MHz, $CDCl_3$, δ) 7.61 (dd, J=6.7, 1.5 Hz, 1 H), 7.59-7.29 (m, 5 H), 6.98 (dd, J=8.2, 1.5 Hz, 1 H), 6.77 (dd, J=8.2, 1.5 Hz, 1 H), 5.31 (s, 2 H), 3.94-3.90 (m, 4 H), 3.08-3.04 (m, 4 H); UV (EtOH) λ max (ε) 244 (22,700), 249 (21,500), 336 (6,270); Anal. calc'd. for $C_{20}H_{19}NO_4$: C, 71.20, H, 5.68, N, 4.15; found: C, 70.84, H, 5.75, N, 4.05.

The second fraction contained a ring contracted product (0.60 g, 33%). Mp 179°–181° C.

The last fraction contains the desired 2-morpholinyl chromone (Cpd #25) (0.29 g, 16%). Mp 139°–40° C.; IR (mull) 2954, 2926, 2870, 2855, 1640, 1623, 1615, 1600, 1470, 1449, 1407, 1239, 1122, 745, 740 cm$^{-1}$; $^1$H-NMR (CDCl$_3$, 200 MHz, δ) 7.65 (broad doublet, J=7.2 Hz, 2 H), 7.47-7.30 (m, 4 H), 6.92 (dd, J=8.1, 0.9 Hz, 1 H), 6.85 (br.d, J=8.1 Hz, 1H) 5.45 (s, 1 H), 5.32 (s, 2 H), 3.89-3.85 (m, 4 H), 3.52-3.47 (m, 4 H); UV (EtOH) λ max (ε) 210 (32,900), 238 (23,500), 252 sh (8,040), 260 sh (5,650), 313 (18,460); Mass Spectrum: ions at m/e (rel intensity) 91 (100), 337 (66), 231 (36), 174 (33), 173 (16), 338 (16) 336 (15), 218 (15), 65 (14), 146 (12); High resolution MS calc'd. for $C_{20}H_{19}NO_4$: 337.1314. Found: 337.1312. Anal. calc'd. for $C_{20}H_{19}NO_4$: C, 71.20, H, 5.58, N, 4.16. Found: C, 71.05, H, 5.56, N, 4.17.

EXAMPLE 26

Preparation of 7,8-dimethoxy-2(4-morpholinyl)-4H-1-benzopyran-4-one, Compound 26

Part A: The 7,8-dimethoxy-3-bromochromone, R. B. Gammill, *Synthesis* (1979), p. 901, (3.42 g, 12.0 mmol) is dissolved in acetonitrile (100 mL) and anhydrous potassium carbonate (1.66 g, 12.0 mmol) is added. Morpholine (1.10 mL, 12.5 mL) is added dropwise and the reaction is warmed to reflux (82° C. bath temperature) for 24 h. The acetonitrile is removed in vacuo, and the mixture is taken up in ethyl acetate (400 mL). The solution is washed with water (2×50 mL) and brine (100 mL), then dried ($MgSO_4$) and concentrated in vacuo to give a yellow solid. Flash chromatography over silica gel (EtOAc/MeOH, 95/5) gave the 3-morpholinyl adduct (2.77 g, 79%), the ring contracted product (0.24 g, 6.9 %) and 0.23 g of a mixture of the ring contracted and the 2-substituted product (79%) Mp 168°–9° C.; IR (mull) 2952, 2924, 2866, 2854, 1639, 1619, 1509, 1456, 1441, 1433, 1322, 1291, 1200, 1171 cm$^{-1}$; $^1$H-NMR (200 MHz, CDCl$_3$, δ) 8.0 (d,1H, 7.56 (s,1H,=C(H)OAr), 7.02 (d,1H,J=8.9 Hz), 4.0 (s,3 H, OCH$_3$), 3.98 (s, 3 H, OCH$_3$), 3.91 (m, 4 H) , 3.08 (m, 4 H), UV (EtOH) λ max (ε) 247 (30,060), 303 (7,490), 326 (3,990); High resolution MS calc'd. for $C_{15}H_{17}NO_5$: 291.1107. Found: 291.1110. Anal. calc'd. for $C_{15}H_{17}NO_5$: C, 61.85; H, 5.88; N, 4.81. Found: C, 61.79; H, 5.86; N, 4.74.

Part B: The mixture of ring contracted and 2-morpholinyl chromone are rechromatographed (SiO$_2$, CH$_2$Cl$_2$/CH$_3$OH, 98/2). The ring-contracted product is recrystallized from EtOH to give pale yellow crystals, Mp 180°–181° C.

The 2-morpholinyl chromone is recrystallized from EtOH to give the desired product (Cpd #26) (colorless crystals); Mp 194.5°–5.5° C.; $^1$H-NMR (CDCl$_3$, δ) 7.88 (d, J=8.8 Hz, 1H), 6.97 (d, J=8.8 Hz, 1H), 5.43 (s, 1 H), 3.98 (s, 3 H), 3.94 (s, 3 H), 3.86 (m, 4 H), 3.55 (m, 4 H). UV (EtOH) λ max (ε) 217 (27,140), 239 (23,530), 270 (6,700), 311 (23,530); High resolution MS calc'd. for $C_{15}H_{17}NO_5$: 291.1107. Found: 291.1093. Anal. calc'd. for $C_{15}H_{17}NO_5$: C, 61.85; H, 5.88; N, 4.81. Found: C, 61.85; H, 5.83; N, 4.78.

EXAMPLE 27

Preparation of 2-(4-methyl-1-piperazinyl)-4H-1-benzopyran-4-one, Compound 27

Following the general procedure outlined in Chart B, the title compound is prepared.

Relating to Chart C:

EXAMPLE 28

Preparation of 8-methyl-7-(phenylmethoxy) -2-[4-(2-pyridinyl)-1-piperazinyl]-4H-benzopyran-4-one, Compound 28

Part A: Preparation of 8-Methyl-7-(Phenylmethoxy)-2-mercapto-4H-1-benzopyran-4-one.

Potassium t-butoxide (65.5 g) is covered with 500 mL of benzene under nitrogen and that solution is placed in a water bath. 4'-Benzyloxy-2'hydroxy-3'-methylacetophenone (50.0 g) and carbon disulfide (14.82 g) are dissolved in 500 mL of benzene and added dropwise to the potassium t-butoxide solution over a one hour period. After complete addition the dark red paste is stirred at room temperature over night and then diluted with one liter of water. That mixture is poured into a separatory funnel and the organic layer discarded. The aqueous is diluted with 300 mL of 20% H2SO4 and the solid that separated is collected on a filter and air dried to yield 31.0 g of a yellow powder. MP 245° C. [D]; 2954, 2916, 2869, 2855, 1619, 1602, 1542, 1499, 1462, 1455, 1377, 1305, 1280, 1113, 1076, 822 cm$^{-1}$; UV (EtOH) λ max (ε) 208 (34260), 231 (24940), 252 (15070), 263 sl sh (9470), 285 sl sh (5030), 299 (4930), 353 (18200), 392 (6840); $^1$H-NMR (DMSO-d$_6$) δ7.73 (d, 1H, J=8.9 Hz), 7.45 (m, 5H, aromatic), 7.24 (d, 1H, J=8.9 Hz), 6.58 (s, 1H, vinyl at C-3), 5.29 (s, 2H), 2.29 (s, 3H, -CH$_3$); Mass spectrum: ions at m/e (relative intensity) 298 (12), 207 (1), 179 (1), 149 (1), 121 (1), 91 (100), 65 (6), 43 (1). See Bantick, J. R. and Suschitzky, J. L., J. Heterocyclic Chem. 18, 679 (1981).

Part B: 8-Methyl-7-(phenylmethoxy)-2-mercapto-4H-1-benzopyran-4-one (2.0 g, 6.7 mmol), 1-(2-pyridyl) piperazine (1.19 g, 7.3 mmol) and TsOH (25 mg) is added to toluene and heated at reflux for 20 hours. The reaction temperature is lowered to room temperature and the toluene removed in vacuo. The resulting dark oil is diluted with EtOAc and the resulting crystals collected on a filter to afford 2.42 g of product. MP 148°–9° C.

Following the general procedure of Example 28, but employing the appropriate amine in place of 1-(2-pyridyl) piperazine there are prepared the following products:

Cpd 29 8-Methyl-7-(phenylmethoxy)-2-(1-piperazinyl)-4H-benzopyran-4-one, Mp 165°–70° C.;

Cpd 30 8-Methyl-7-(phenylmethoxy)-2-(1-pyrrolidinyl)-4H-benzopyran-4-one, Mp 190°–3° C.;

Cpd 31 8-Methyl-7-(phenylmethoxy)-2-(1-piperidinyl)-4H-benzopyran-4-one, Mp 172°–4° C.;

Cpd 32 8-Methyl-2-(4-methyl-1-piperazinyl)-7-(phenylmethoxy)-4H-benzopyran-4-one, Mp 180°–1° C.;

Cpd 33 8-Methyl-7-(phenylmethoxy)-2-(2,6-dimethyl-4-morpholinyl)-4H-benzopyran-4-one, Mp 166°–8° C.;

Cpd 34 2-[4-(Hydroxyethyl)-1-piperazinyl]-8-methyl-7-(phenylmethoxy)-4H-benzopyran-4-one monohydrochloride, Mp 253°–5° C.;

Cpd 35 2-[4-(Diphenylmethyl)-1-piperazinyl]-8-methyl-7-(phenylmethoxy)-4H-benzopyran-4-one, Mp 90°–5° C.;

Cpd 36 8-Methyl-7-(phenylmethoxy)-2-(4-phenyl-1-piperidinyl)-4H-benzopyran-4-one, Mp 193°–4° C.;

Cpd 37 8-Methyl-7-(phenylmethoxy)-2-(4-phenyl-1-piperazinyl)-4H-benzopyran-4-one, Mp 153°–4° C.; and Cpd 38 2-(4-Hydroxy-1-piperdinyl)-8-methyl-7-(phenylmethoxy)-4H-benzopyran-4-one, Mp 104°–5° C.

Relating to Chart D and E:

EXAMPLE 39

Preparation of 7-hydroxy-2-(4-morpholinyl)-8-methyl-4H-1-benzopyran-4-one, Compound 39 (according to Chart D).

Part A: 8-Methyl-2-(4-morpholinyl)-7-(phenylmethoxy)-4H-1-benzopyran-4-one (8.59 g, 24.4 mmol.) is suspended in 250 ml of ethyl acetate. 9.9 ml of cyclohexene is added followed by 0.85 g of 10% Palladium on carbon. The mixture is heated at reflux for 18 hours. The reaction is allowed to cool and filtered, the solid is taken up in methanol, decanted and filtered. The methanol is evaporated to give 4.71 g (74%) of the phenol (mp>250° C.).

Alternate Part A: 2',4',-Dihydroxy-3'-methylacetophenone (90% purity, 1.108 g, 6 mmole) is suspended in 25 ml 1,2-dichloroethane and the mixture is treated with boron trifluoride etherate (1.48 ml, 12 mmole) while stirring in a 50 ml one neck round bottom flask under nitrogen. The mixture is stirred for 30 min at room temperature and is subsequently treated with morpholine-4-phosgene iminium chloride (2.70 g, 13.2 mmole). The reaction mixture is warmed to 70° C. for 3 h. The reaction is cooled to room temperature and the insoluble orange solid is collected by filtration and the filter cake is washed well with diethylether. The solid is taken up in 25 ml acetonitrile in a 50 ml one neck round bottom flask under nitrogen and the solution is cooled to 0° C. The mixture is treated with 2.5 ml water and the reaction is stirred for 48 h as the cooling bath expired. The acetonitrile is removed in vacuo and the residue is carefully diluted with 75 ml 2:1 saturated sodium bicarbonate/sodium chloride. The mixture is extracted with 4×35 ml dichloromethane. The combined organics are dried over magnesium sulfate and are concentrated in vacuo to an amber solid. The solid is washed successively with ethylacetate and diethylether to afford 980 mg (44%) of [8-methyl-2-(4-morpholinyl) -4-oxo-4H-1-benzopyran-7-yl]4-morpholinyl carboxylic acid ester (Cpd 100) M.P. 232°–234° C. The carbamate (945 mg, 2.51 mole) is suspended in 9 ml 2/1 methanol/water in a 25 ml on neck round bottom flask under nitrogen. The suspension is treated with lithium hydroxide (236 mg, 5.62 mmole) and the reaction mixture is stirred for 48 h at room temperature. The methanol is removed in vacuo and the pH of the aqueous residue is adjusted to pH=4.9 by the addition of 5% hydrochloric acid. The precipitated material is collected by filtration and is dried in vacuo at 25° C. to afford 569 mg (87%) of phenol 39 (M.P.>250° C.) as a chalky grayish solid.

Second Alternate Part A: 2',4'-Dihydroxy-3'-methylacetophenone (90% purity, 18.46 g, 100 mmole) is suspended in 50 ml diethylether in a 100 ml one neck round bottom flask under nitrogen. The mixture is treated with boron trifluoride etherate (18.45 ml, 150 mmole) and the reaction is stirred overnight at room temperature. The precipitated material is collected by filtration and the filter cake is washed well with fresh diethylether. The filtered material is air dried to afford 10.45 g (47%) of difluoroboronate salt as a yellow solid.

The difluoroboronate salt (10.45 g, 47 mmole) is combined with morpholine-4-phosgene iminium chloride (21.2 g, 104 mmole) in 125 ml 1,2-dichloroethane in a 250 ml one neck round bottom flask under argon. The reaction mixture is warmed to 70° C. for 3 h and is cooled to room temperature. The orange-yellow precipitate is collected by filtration and is washed successively with 1,2-dichloroethane and diethylether to provide 25.3 g of an orange solid. The solid is suspended in 200 ml acetonitrile in a 500 ml one neck round bottom flask and the mixture is cooled to 0° C. The cooled mixture is treated with 20 ml water and after stirring 20 min at 0° C., the reaction mixture is stirred overnight at room temperature. The mixture is subsequently cooled to −33° C. for 2 h and the precipitated hydrochloride salt is collected by filtration and is washed with 125 ml ice cold acetonitrile. The filter cake is dried to provide 13.25 g (69%) of the carbamate-chromone hydrochloride as a white solid. The filtrate is concentrated in vacuo to an amber syrup. The syrup is diluted with 100 ml saturated sodium bicarbonate and the mixture is extracted with 4×50 ml dichloromethane. The combined organics are dried over magnesium sulfate and are concentrated in vacuo to a reddish oil which upon crystallization with ethylacetate yielded 875 mg (5%) of carbamate-chromone as a yellow solid. Hydrolysis of the carbamate-chromone as described in method B affords the desired phenol.

Part B: 7-Hydroxy-8-methyl-2-(4-morpholinyl)-4H-1-benzopyran-4-one (0.50 g, 1.91 mmol) is suspended in 15 ml of acetonitrile. 1.3 g of potassium carbonate is added followed by 0.39 g (2.1 mmol) of alphabromo-p-xylene. The mixture is refluxed for 5 hours. 0.04 g of additional alkylating agent is added and the mixture is refluxed for 2 hours. The cooled mixture is diluted with 5 ml of water and filtered. The white solid is washed with water and dried. The solid is recrystallized from ethyl acetate to afford 0.59 g (84%) of the product 48 (mp 167.5°–168° C.).

Following the general procedure of Example 39 but employing the appropriate 2'-hydroxyacetophenone (Alternate Part A) or phenylmethoxy aminochromone (Part A) as well as the appropriate alkylating agen and suitable base, e.g. potassium carbonate or sodium hydride, (Part B, if required) there are prepared the following products:

Cpd 40 6-Hydroxy-2-(4-morpholinyl)-4H-1-benzopyran-4-one, Mp 290°–2° C.;

Cpd 41 7-Hydroxy-2-(4-morpholinyl)-4H-1-benzopyran-4-one;

Cpd 42 5-Hydroxy-2-(4-morpholinyl)-4H-1-benzopyran-4-one, Mp 295°–7° C.;

Cpd 43 8-Hydroxy-2-(4-morpholinyl)-4H-1-benzopyran-4-one, Mp 300° C.;

Cpd 44 7-Methoxy-8-methyl-2-(4-morpholinyl)-4H-1-benzopyran-4-one, Mp 224.5°–225.5° C.;

Cpd 45 [(8-methyl-2-(4-morpholinyl)-4H-1-benzopyran-7-yl)oxy)acetic acid, Mp 299.5°–301° C.;

Cpd 46 [[8-Methyl-2-(4-morpholinyl)-4-oxy-4H-1-benzopyran-7-yl]oxy]acetic acid methyl ester, Mp 181°–2° C.;

Cpd 47 7-[(4-Methoxyphenyl)methoxy]-8-methyl-2-(4-morpholinyl)-4H-1-benzopyran-4-one, Mp171°–2° C.;

Cpd 48 8-Methyl-7-[(4-methylphenyl)methoxy]-2-(4-morpholinyl)-4H-1-benzopyran-4-one, Mp 167.5°–8° C.;

Cpd 49 7-[(4-Chlorophenyl)methoxy]-8-methyl-2-(4-morpholinyl)-4H-1-benzopyran-4-one, Mp 226°–7° C.;

Cpd 50 7-[(4,5-Dichlorophenyl)methoxy]-8-methyl-2-(4-morpholinyl)-4H-1-benzopyran-4-one, Mp243°–4° C.;

Cpd 51 8-Methyl-2-(4-morpholinyl)-7-(2-pyridinylmethoxy)-4H-1-benzopyran-4-one; Mp 174–175.5;

Cpd 52 8-Methyl-7-[[(phenyl)carbonyl]oxy]-2-(4-morpholinyl)-4H-1-benzopyran-4-one, Mp 223.5°–25° C.;

Cpd 53 8-Methyl-7-(2-(4-methyl-(1-piperizinyl))ethyl) oxy-2-(4-morpholinyl) -4H-1-benzopyran-4-one, Mp 159.0°–159.5° C.

Cpd 54 7-[[4-(1,1-Dimethylethyl)phenyl]methoxy]-8-methyl-2-(4-morpholinyl)-4H-1-benzopyran-4-one, Mp 218.5°–220° C.;

Cpd 55 8-Methyl-2-(4-morpholinyl)-7-[[4-phenylmethoxy)phenyl]methoxy]-4H-1-benzopyran-4-one, Mp 110°–111° C.;

Cpd 56 7-[(3-Methoxyphenyl)methoxy]-8-methyl-2-(4-morpholinyl)-4H-1-benzopyran-4-one, Mp 153.5°–155.5° C.;

Cpd 57 7-[(4-Nitrophenyl)methoxy]-8-methyl-2-(4-morpholinyl)-4H-1-benzopyran-4-one, Mp 285° C. dec.;

Cpd 58 7-[(2-Phenylethyl)methoxy]-8-methyl-2-(4-morpholinyl)-4H-1-benzopyran-4-one, Mp 200.5°–201.5° C. dec.;

Cpd 59 7-[(2-Methoxyphenyl)methoxy]-8-methyl-2-(4-morpholinyl)-4H-1-benzopyran-4-one, Mp 202°–203° C.;

Cpd 60 7-[(4-Ethoxyphenyl)methoxy]-8-methyl-2-(4-morpholinyl)-4H-1-benzopyran-4-one, Mp 186°–188° C.;

Cpd 61 8-(4-Ethoxy-benzyloxy)-2-(4-morpholinyl)-4H-1-benzopyran-4-one, Mp 149.5°–151.5° C.;

Cpd 62 2-(4-Morpholinyl)-8-(4-nitro-benzyloxy)-4H-1-benzopyran-4-one, Mp 240°–241° C.;

Cpd 63 8-(2-Methoxy-benzyloxy)-2-(4-morpholinyl)-4H-1-benzopyran-4-one, Mp 149°–150° C.;

Cpd 64 2-(4-Morpholinyl)-8-(2-phenyl-ethoxy)-4H-1-benzopyran-4-one, Mp 131°–132° C.;

Cpd 65 2-(4-Morpholinyl)-(2-oxo-2-phenyl-ethoxy)-4H-1-benzopyran-4-one, Mp 200°–201.5° C.;

Cpd 66 8-(4-Benzyloxy-benzyloxy)-2-(4-morpholinyl)-4H-1-benzopyran-4-one, Mp 143.5°–145° C.;

Cpd 67 8-(4-Chloro-benzyloxy)-2-(4-morpholinyl)-4H-1-benzopyran-4-one, Mp 208°–209° C.;

Cpg 68 8-(4-t-Butyl-benzyloxy)-2-(4-morpholinyl)-4H-1-benzopyran-4-one, Mp 165.5°–166.5° C.;

Cpd 69 8-(3-Methoxy-benzyloxy)-2-(4-morpholinyl)-4H-1-benzopyran-4-one, Mp 177°–178° C.;

Cpd 70 8-(3,4-Dichloro-benzyloxy)-2-(4-morpholinyl)-4H-1-benzopyran-4-one, Mp 207°–208° C.;

Cpd 71 8-(4-Methyl-benzyloxy)-2-(4-morpholinyl)-4H-1-benzopyran-4-one, Mp 177°–178° C.;

Cpd 72 8-(4-Methoxy-benzyloxy)-2-(4-morpholinyl)-4H-1-benzopyran-4-one, Mp 173.5°–174.5° C.;

Cpd 73 2-(4-Morpholinyl)-8-(naphthyl-2-methyloxy)-4H-1-benzopyran-4-one, Mp 200.5°–201.5° C.;

Cpd 74 2-(4-Morpholinyl)-8-(naphthyl-1-methyloxy)-4H-1-benzopyran-4-one, Mp 192.5°–193.5° C.;

Cpd 75 8-Methyl-2-(4-morpholinyl)-7-(naphthyl-2-methyloxy)-4H-1-benzopyran-4-one, Mp 158.5°–159.5° C.;

Cpd 76 8-Methyl-2-(4-morpholinyl)-7-(naphthyl-1-methyloxy)-4H-1-benzopyran-4-one, Mp 205.5°–207° C.;

Cpd 77 2-(Dimethylamino)-8-methyl-4-oxo-4H-1-benzopyran-7-yl carbamic acid dimethyl ester, Mp 191°–2° C.;

Cpd 78 2-(Dimethylamino)-4-oxo-4H-1-benzopyran-6-yl carbamic acid dimethyl ester, Mp 179.5°–80° C.;

Cpd 79 2-(Dimethylamino)-4-oxo-4H-1-benzopyran-7-yl carbamic acid dimethyl ester, Mp 158°–9° C.;

Cpd 80 2-(Dimethylamino)-4H-1-benzopyran-4-one, Mp 122°–23.5° C.;

Cpd 81 2-(Dimethylamino)-8-methyl-7-(phenylmethoxy)-4H-1-benzopyran-4-one, Mp 165°–6° C.;

Cpd 100 8-Methyl-2-(4-morpholinyl)-7-(2-oxo-2-phenylethoxy)-4H-1-benzopyran-4-one, Mp. 226.5–227.5;

Cpd 103 6-Chloro-8-methyl-2-(4-morpholinyl)-7-(phenylmethoxy)-4H-1-benzopyran-4-one, Mp. 207–209;

Cpd 104 [[2-(4-Morpholinyl)-4-oxo-4H-1-benzopyran-8-yl]oxy]-acetic acid, methyl ester, Mp. 192.5–193;

Cpd 105 4-[[[8-Methyl-2-(4-morpholinyl)-4-oxo-4H-1-benzopyran-7-yl]oxy]methyl]-benzoic acid, methyl ester, Mp. 226–228;

Cpd 106 4-[[[2-(4-Morpholinyl)-4-oxo-4H-1-benzopyran-8-yl]oxy]methyl]-benzoic acid, methyl ester, Mp. 207–209;

Cpd 107 8-Methyl-2-(4-morpholinyl)-7-[[3-(trifluoromethyl)phenyl]methoxy]-4H-1-benzopyran-4-one, Mp. 194.5–195.5;

Cpd 108 2-(4-Morpholinyl)-8-[[3-(trifluoromethyl)phenyl]methoxy]-4H-1-benzopyran-4-one, Mp. 204–204.5;

Cpd 109 7-(Cyclohexylmethoxy)-8-methyl-2-(4-morpholinyl)-4H-1-benzopyran-4-one, Mp. 184.5–185.5;

Cpd 110 8-Methyl-2-(4-morpholinyl)-7-(2-propenyloxy)-4H-1-benzopyran-4-one, Mp. 191–192;

Cpd 111 2-(4-Morpholinyl)-7-(1-naphthalenylmethoxy)-4H-1-benzopyran-4-one, Mp. 195.2–195.8;

Cpd 112 8-Methyl-2-(4-morpholinyl)-7-(3-pyrindinylmethoxy)-4H-1-benzopyran-4-one, Mp. 182.5–184;

Cpd 113 8-Methyl-2-(4-morpholinyl)-7-(4-pyrindinylmethoxy)-4H-1-benzopyran-4-one, Mp. 253.5–255.5;

Cpd 115 8-methyl-2-(4-morpholinyl)-7-(2-quinoxalinylmethoxy)-4H-1-Benzopyran-4-one, Mp. 250.5–252.5;

Cpd 116 8-methyl-2-(4-morpholinyl)-7-(pyrazinlymethoxy)-4H-1-Benzopyran-4-one, Mp. 236–237;

Cpd 117 8-methyl-2-(4-morpholinyl)-7-(2-pyridinylmethoxy)-4H-1-Benzopyran-4-one, N-oxide, Mp. 248–249.5;

Cpd 118 8-methyl-2-(4-morpholinyl)-7-(3-pyridinylmethoxy)-4H-1-Benzopyran-4-one, N-oxide, Mp. 233.5–234;

Cpd 119 8-Iodo-2-(4-morpholinyl)-7-(3-pyrindinylmethoxy)-4H-1-benzopyran-4-one, Mp. 214–215;

Cpd 120 3,3-Dimethyl-1-[[8-methyl-2-(4-morpholinyl)-4-oxo-4H-1-benzopyran-7-yl]oxy]-butan-2-one, Mp. 197–198;

Cpd 121 1-[[8-Methyl-2-(4-morpholinyl)-4-oxo-4H-1-benzopyran-7-yl]oxy]-propan-2-one, mp. 206.5;

Cpd 122 1-[[8-Methyl-2-(4-morpholinyl)-4-oxo-4H-1-benzopyran-7-yl]oxy]-butan-2-one, mp. 183–184;

Cpd 123 8-Methyl-2-(4-morpholinyl)-7-(2-oxo-2-(2-naphthyl)ethoxy)-4H-1-benzopyran-4-one, mp. 214.5–215.5;

Cpd 125 2-(4-Morpholinyl)-7-(2-pyrindinylmethoxy)-4H-1-benzopyran-4-one, mp. 274–276;

Cpd 126 2-(4-Morpholinyl)-7-(3-pyrindinylmethoxy)-4H-1-benzopyran-4-one, mp. 193–194;

Cpd 127 2-(4-Morpholinyl)-8-(2-pyrindinylmethoxy)-4H-1-benzopyran-4-one, mp. 199–200;

Cpd 128 2-(4-Morpholinyl)-8-(3-pyrindinylmethoxy)-4H-1-benzopyran-4-one, mp. 160–161;

Cpd 129 8-methyl-2-(4-morpholinyl)-7-(2-quinolinylmethoxy)-4H-1-Benzopyran-4-one, mp. 223.5–224.5;

Cpd 130 7,8-(Bis)-phenylmethoxy-2-(4-morpholinyl)-4H-1-benzopyran-4-one, mp. 165.5–167;

Cpd 131 7,8-(Bis)-acetyloxy-2-(4-morpholinyl)-4H-1-benzopyran-4-one, mp. 231.5–233;

Cpd 132 7,8-(Bis)-hydroxy-2-(4-morpholinyl)-4H-1-benzopyran-4-one, mp.>300;

Cpd 133 7-Hydroxy-2-(4-morpholinyl)-8-phenylmethoxy-4H-1-benzopyran-4-one, mp. 198–199;

Cpd 134 7,8-(Bis)-(3-trifluoromethyl)phenylmethoxy-2-(4-morpholinyl)-4H-1-benzopyran-4-one, mp. 178.5–179.5;

Cpd 135 8-Hydroxy-2-(4-morpholinyl)-7-(3-trifluoromethyl) phenylmethoxy-4 H-1-benzopyran-4-one, mp. 262–262.5;

Cpd 136 7-Hydroxy-2-(4-morpholinyl)-8-(3-trifluoromethyl) phenylmethoxy-4H-1-benzopyran-4-one, mp. 236–237;

Cpd 137 7-[3-(1-cyclohexyl-1H-tetrazol-5-yl)propoxy]-8-methyl-2-(4-morpholinyl)-4H-1-Benzopyran-4-one, mp. 228–230;

Cpd 138 8-[3-(1-cyclohexyl-1H-tetrazol-5-yl)propoxy]-2-(4-morpholinyl)-4H-1-Benzopyran-4-one, mp. 185–186;

Cpd 139 7-[(1-cyclohexyl-1H-tetrazol-5-yl)methoxy]-8-methyl-2-(4-morpholinyl)-4H-1-Benzopyran-4-one, mp. 228;

Cpd 140 8-[(1-cyclohexyl-1H-tetrazol-5-yl)methoxy]-2-(4-morpholinyl)-4H-1-Benzopyran-4-one, mp. 218;

Cpd 141 2-(4-morpholinyl)-8-[(1-phenyl-1H-tetrazol-5-yl)oxy]-4H-1-Benzopyran-4-one, mp. 214–215;

Cpd 142 N-cyclohexyl-2-[[2-(4-morpholinyl)-4-oxo-4H-1-benzopyran-8-yl]oxy]-acetamide, mp. 238–241;

Cpd 143 N-(1,1-dimethylethyl)-2-[[2-(4-morpholinyl)-4-oxo-4H-1-benzopyran-8-yl]oxy]-acetamide, mp. 219–220;

Cpd 144 2-[[2-(4-morpholinyl)-4-oxo-4H-1-benzopyran-8-yl]-N-phenyl-acetamide, mp. 225–228;

Cpd 145 2-[[2-(4-morpholinyl)-4-oxo-4H-1-benzopyran-8-yl]oxy]-N-(1-phenylethyl)-acetamide, mp. 178–180;

Cpd 146 N-cyclohexyl-2-[[8-methyl-2-(4-morpholinyl)-4-oxo-4H-1-benzopyran-7-yl]oxy]-acetamide, mp. 255–256;

Cpd 147 N-[[[8-methyl-2-(4-morpholinyl)-4-oxo-4H-1-benzopyran-7-yl]oxy]acetyl]-Phenylalanine, ethyl ester, mp. 173–175;

Cpd 148 2-[[8-methyl-2-(4-morpholinyl)-4-oxo-4H-1-benzopyran-7-yl]oxy]-N-phenyl-acetamide, mp. 242–244;

Cpd 149 8-methyl-2-(4-morpholinyl)-7-[(1-phenyl-1H-tetrazol-5-yl)oxy]-4H-1-Benzopyran-4-one, mp. 209–211;

Cpd 150 6-[(1-cyclohexyl-1H-tetrazol-5-yl)methoxy]-2-(4-morpholinyl)-4H-1-Benzopyran-4-one, mp. 215–217;

Cpd 151 2-[[8-methyl-2-(4-morpholinyl)-4-oxo-4H-1-benzopyran-7-yl]oxy]-N-(1-phenylethyl)-acetamide, mp. 203–205;

Cpd 152 2-[[8-methyl-2-(4-morpholinyl)-4-oxo-4H-1-benzopyran-7-yl]oxy]-N-3-pyridinyl-acetamide, mp. 243–245;

Cpd 153 N-[[[8-methyl-2-(4-morpholinyl)-4-oxo-4H-1-benzopyran-7-yl]oxy]acetyl]-Phenylalanine, mp. 259–262;

Cpd 154 7-(2,2-dimethoxyethoxy)-8-methyl-2-(4-morpholinyl)-4H-1-Benzopyran-4-one, mp. 168–169;

Cpd 155 2-(4-Morpholinyl)-8-(2-propenyl)-4H-1-benzopyran-4-one mp. 145.5–146.5;

Cpd 156 2-(4-Morpholinyl)-8-(1-propenyl)-4H-1-benzopyran-4-one mp. 163–164;

Cpd 157 8-Formyl-2-(4-Morpholinyl)-4H-1-benzopyran-4-one mp. 209–209.5;

Cpd 158 2-(4-morpholinyl)-8-(phenylamino)methyl-4H-1-benzopyran-4-one, mp. 226–227;

Cpd 159 2-(4-morpholinyl)-8-(2E-phenyl)ethenyl-4H-1-benzopyran-4-one, mp. 209–209.5;

Cpd 160 8-Hydroxymethyl-2-(4-Morpholinyl)-4H-1-benzopyran-4-one, mp. 243–243.5;

Cpd 162 8-methyl-7-[(1-methyl-3-piperidinyl)methoxy]-2-(4-morpholinyl)-4H-1-Benzopyran-4-one, mp. 159–161;

Cpd 163 8-Methyl-2-(4-morpholinyl)-7-(2-(1-piperidinyl)ethyl)oxy-4H-1-benzopyran-4-one, mp. 154–156;

Cpd 164 8-Methyl-2-(4-morpholinyl)-7-(2-(1-pyrrolidinyl)ethyl)oxy-4H-1-benzopyran-4-one, mp. 136–138;

Cpd 165 8-Methyl-2-(4-morpholinyl)-7-(2-(4-morpholinyl)ethyl)oxy-4H-1-benzopyran-4-one, mp. 170.5–172.5;

Cpd 166 8-Methyl-2-(4-morpholinyl)-7-(3-(1-piperidino)propyl)oxy-4H-1-benzopyran-4-one, mp. 144–145;

Cpd 167 7-(2-Diethylaminoethyl)oxy-8-methyl-2-(4-morpholinyl)-4H-1-benzopyran-4-one, mp. 162–162.5;

Cpd 168 7-[2-(ethylphenylamino)ethoxy]-8-methyl-2-(4-morpholinyl)-4H-1-benzopyran-4-one, mp. 146–147;

Cpd 169 7-(2-Diisopropylaminoethyl)oxy-8-methyl-2-(4-morpholinyl)-4H-1-benzopyran-4-one, mp. 136.5–138.5;

Cpd 170 7-Hydroxy-8-methyl-2-(1-piperidinyl)-4H-1-benzopyran-4-one, mp. 278–284;

Cpd 171 8-Methyl-2-(1-piperidinyl)-7-(3-pyrindinylmethoxy)-4H-1-benzopyran-4-one, mp. 144–158;

Cpd 172 7-(2-(4-Benzyl-(1-piperizinyl))ethyl)oxy-8-methyl-2-(4-morpholinyl)-4H-1-benzopyran-4-one, mp. 138–139;

Cpd 216 8-Methyl-7-[(2-methoxy)ethyl]oxy-2-(4-morpholinyl)-4H-1-benzopyran-4-one, mp. 165–166;

Cpd 219 8-Methyl-7-[(2-thiomethyl)ethyl]oxy-2-(4-Morpholinyl)-4H-1-benzopyran-4-one, mp. 182.5–184;

Cpd 221 8-Methyl-7-[2-(phenylmethoxy)ethyl]oxy-2-(4-morpholinyl)-4H-1-benzopyran-4-one, mp. 155–156;

Cpd 222 7-[2-(Hydroxy)ethyl]oxy-8-methyl-2-(4-morpholinyl)-4H-1-benzopyran-4-one, mp. 267–268;

Cpd 333 7-[2-(2-methoxyethoxy)ethoxy]-8-methyl-2-(4-morpholinyl)-4H-1-Benzopyran-4-one, mp. 127–128;

Cpd 334 8-methyl-2-(4-morpholinyl)-7-(2-phenoxyethoxy)-4H-1-Benzopyran-4-one, mp. 178–179;

Cpd 251 N-cyclohexyl-N-methyl-2-[[2-(4-morpholinyl)-4-oxo-4H-1-benzopyran-6-yl]oxy]-Acetamide, mp. 168–169;

Cpd 252 2-(4-morpholinyl)-6-(1-naphthalenylmethoxy)-4H-1-Benzopyran-4-one, mp. 205–207;

Cpd 262 8-methyl-2-(4-morpholinyl)-7-[(1-phenyl-1H-tetrazol-5-yl)methoxy]-4H-1-Benzopyran-4-one, mp. 238–241;

Cpd 263 5-[[[8-methyl-2-(4-morpholinyl)-4-oxo-4H-1-benzopyran-7-yl]oxy]methyl]-α-(phenylmethyl)-1H-Tetrazole-1-acetic acid ethyl ester, mp. 61–68;

Cpd 266 7-[[1-(1,1-dimethylethyl)-1H-tetrazol-5-yl]methoxy]-8-methyl-2-(4-morpholinyl)-4H-1-Benzopyran-4-one, mp. 261–263;

Cpd 271 8-methyl-1-(4-morpholinyl)-7-[[1-(1-phenylethyl)-1H-tetrazol-5-yl]methoxy]-4H-1-Benzopyran-4-one, mp. 181–183;

Cpd 298 7-(acetyloxy)-6-bromo-8-methyl-2-(4-morpholinyl)-4H-1-Benzopyran-4-one, mp. 249.5–250.5;

Cpd 299 7-(acetyloxy)-6,8-dimethyl-2-(4-morpholinyl)-4H-1-Benzopyran-4-one, mp. 245–246;

Cpd 300 7-hydroxy-6,8-dimethyl-2-(4-morpholinyl)-4H-1-Benzopyran-4-one, mp.>300;

Cpd 301 7-(acetyloxy)-6-iodo-8-methyl-2-(4-morpholinyl)-4H-1-Benzopyran-4-one, mp. 214–216, dec;

Cpd 302 7-hydroxy-6-iodo-8-methyl-2-(4-morpholinyl)-4H-1-Benzopyran-4-one, mp. 243–244, dec;

Cpd 303 6-bromo-7-hydroxy-8-methyl-2-(4-morpholinyl)-4H-1-Benzopyran-4-one, mp. 284–285, dec;

Cpd 305 2-(4-morpholinyl)-8-(2-quinolinylmethoxy)-4H-1-Benzopyran-4-one, mp. 247–248;

Cpd 312 2-(4-morpholinyl)-8-(2-propenyloxy)-4H-1-Benzopyran-4-one, mp. 158–159;

Cpd 286 7-(acetyloxy)-2-(4-morpholinyl)-8-(2-propenyl)-4H-1-Benzopyran-4-one, mp. 183–184.5;

Cpd 287 7-(acetyloxy)-2-(4-morpholinyl)-8-propyl-4H-1-Benzopyran-4-one, mp. 183.5–184.5;

Cpd 288 7-hydroxy-2-(4-morpholinyl)-8-propyl-4H-1-Benzopyran-4-one, mp. 294–297;

Cpd 289 7-[2-(4-methyl-1-piperazinyl)ethoxy]-2-(4-morpholinyl)-8-propyl-4H-1-Benzopyran-4-one, mp. 158–159;

Cpd 290 2-(4-morpholinyl)-8-propyl-7-[2-(1-pyrrolindinyl)ethoxy]-4H-1-Benzopyran-4-one, mp. 162–163.5;

Cpd 291 2-(4-morpholinyl)-7-[2-(1-piperidinyl)ethoxy]-8-propyl-4H-1-Benzopyran-4-one, mp. 174–174.75;

Cpd 292 2-(4-morpholinyl)-7-[2-(4-phenyl-1-piperidinyl)ethoxy]-8-propyl-4H-1-Benzopyran-4-one, mp. 142.5–143.5;

Cpd 293 2-(4-morpholinyl)-8-propyl-7-[2-(4-thiomorpholinyl)ethoxy]-4H-1-Benzopyran-4-one, mp. 161.5–162;

Cpd 294 (R)-7-[2-[2-(hydroxymethyl)-1-pyrrolidinyl]ethoxy]-2-(4-morpholinyl)-8-propyl-4H-1-Benzopyran-4-one, mp. 127.5–129;

Cpd 320 7-[2-(4-methyl-1-piperazinyl)ethoxy]-2-2(4-morpholinyl)-8-(2-propenyl)-4H-1-Benzopyran-4-one, mp. 165–165.5;

Cpd 321 2-(4-morpholinyl)-8-(2-propenyl)-7-[2-(1-pyrrolidinyl)ethoxy]-4H-1-Benzopyran-4-one, mp. 169.5–171;

Cpd 322 2-(4-morpholinyl)-7-[2-(1-piperidinyl)ethoxy]-8-(2-propenyl)-4H-1-Benzopyran-4-one, mp. 184.5–186;

Cpd 323 2-(4-morpholinyl)-7-[2-(4-phenyl-1-piperidinyl)ethoxy]-8-(2-propenyl)-4H-1-Benzopyran-4-one, mp. 148.5–149;

Cpd 324 2-(4-morpholinyl)-8-(2-propenyl)-7-[2-(4-thiomorpholinyl)ethoxy]-4H-1-Benzopyran-4-one, mp. 165–166.5;

Cpd 325 (R)-7-[2-[2-(hydroxymethyl)-1-pyrrolidinyl]ethoxy]-2-(4-morpholinyl)-8-(2-propenyl)-4H-1-Benzopyran-4-one, mp. 136.5–138;

Cpd 348 7-[(1-cyclopropyl-1H-tetrazol-5-yl)methoxy]-8-methyl-2-(4-morpholinyl)-4H-1-Benzopyran-4-one, mp. 241–242; and Cpd 349 7-[(1-cyclobutyl-1H-tetrazol-5-yl) methoxy]-8-methyl-2-(4-morpholinyl)-4H-1-Benzopyran-4-one, mp. 179–181.

EXAMPLE 82

Preparation of 2-(4-Morpholinyl)-4H-1-benzopyran-4-one. Compound 2

Part A: Potassium t-butoxide (134 g, 1.2 mole) is covered with benzene (1 L) in a flame dried round bottom flask equipped with an overhead stirrer, addition funnel, thermometer, and a nitrogen inlet. This suspension is maintained at 15° C. A solution of o-hydroxyacetophenone (54.4 g, 48.1 ml, 0.4 mole) and carbon disulfide (30.4, 24 ml, 0.4 mole) in benzene (700 ml) is slowly added over 1.3 hours, applying an ice bath periodically in order to maintain the temperature 18° C. The slurry which forms is stirred at ambient temperature for one day. The reaction mixture is transferred to a separatory funnel containing water (4 L) and extracted with ether (4×250 ml) and EtOAc (3×250 ml). The aqueous layer is acidified with 10% $H_2SO_4$ (1 L) and stirred at ambient temperature overnight. The resulting solid is filtered off and dried in vacuo at 50° C. overnight to yield 22.07 g of 2-mercapto-4H-1-benzopyran-4-one. Mp 207°–8° C.

Part B: Tosic acid (0.4 g, 2 mmol) is added to a solution of 2-mercapto-4H-1-benzopyran-4-one (3.56 g, 20 mmol) and morpholine (2.44 g, 2.44ml, 28 mmol) in benzene (400ml). After refluxing for 4 hours, the reaction mixture is transferred to a separatory funnel containing EtOAc and water. Extracting with EtOAc (2×), washing with combined organic layers with water and brine, and filtering through sodium sulfate yields 4.56 of crude material after evaporation of the solvent. Flash chromatography over silica gel (300 g, 2.5% MeOH/CHCl$_3$, 50 ml fractions) yields 2.07 g of 2-(4-Morpholinyl)-4H-1-benzopyran-4-one (44.8%, fractions 22–32). Mp 160°–1° C.

EXAMPLE 83

Preparation of 6-Methyl-2-(4-morpholinyl)-4H-1,3-benzoxazin-4-one, Compound 83

The methyl ester of 5-methylsalicylic acid (2.73 g; 16.4 mmol) is dissolved in acetone (50 ml), cyanogen bromide (1.81 g; 17.2 mmol) is added and the solution is cooled to 0° C. Triethylamine (1.73 g; 18.2 mmol) is dissolved in acetone (5 ml) and added dropwise. Precipitation occurred rapidly and the solid is removed by filtration. The filtrate is concentrated in vacuo to afford 3.41 g of the intermediate cyanoether. The cyanoether is dissolved in acetonitrile (50 ,1), morpholine (1.43 g; 16.4 mmol) is added in 5 ml of acetonitrile and the reaction is stirred for two hours at room temperature. Crystals form and the reaction mixture is cooled to 0° C., and washed with cold acetonitrile to afford 1.65 g (40.8%). Mother liquors are recrystallized from acetonitrile to afford 0.54 g (13.4%); mp 197°–197.9° C.; IR (mull) 2955, 2923, 2858, 1674, 1619, 1576, 1466, 1453, 1433, 1424, 1333, 1325, 1315, 1112, 817 cm$^{-1}$; $^1$H-NMR (CDCl$_3$, δ) 7.91 (d, J=1.4 Hz, 1 H, aromatic), 7.40 (d of d's, J=8.3 Hz, 1.9 Hz, 1 H, aromatic), 7.09 (d, J=8.4 Hz, 1 H, aromatic), 3.81 (broad s, 8H, morpholine methylenes), 2.40 (s, 3 H, methyl); UV λ max (ε) 217sh (26,550), 223sh (26,350), 259 (15,100), 296(4,250), 304sh (3,550); Mass spectrum, ions at m/e (relative intensity) 246(parent, 29), 218(10), 189 (20), 134 (base, 100), 10e(18), 105(10), 78(12), 77(8), 28(19);

Anal. Calc'd. for: $C_{13}H_{14}N_2O_3$: C, 63.40; H, 5.73; N, 11.38.

Found: C, 63.29; H, 5.92; N, 11.31.

Following the general procedure of Example 83, but employing the appropriate o-hydroxy salicylic methyl ester in place of the methyl ester of 5-methylsalicylic acid there are prepared the following products:

Cpd 84 8-Methyl-2-(4-morpholinyl)-4H-1,3-benzoxazin-4-one, Mp 229°–231° C.;

Cpd 85 6-Bromo-2-(4-morpholinyl)-4H-1,3-benzoxazin-4-one, Mp 207°–214° C.;

Cpd 86 7-Chloro-2-(4-morpholinyl)-4H-1,3-benzoxazin-4-one, Mp 207°–214° C.;

Cpd 87 6,8-Bis(1-methylethyl)-2-(4-morpholinyl)-4H-1,3-benzoxazin-4-one, Mp 120°–120.5° C.;

Cpd 88 6-Fluoro-2-(4-morpholinyl)-4H-1,3-benzoxazin-4-one, Mp 220°–231° C.;

Cpd 89 6-Dimethoxymethyl-2-(4-morpholinyl)-4H-1,3-benzoxazin-4-one; Mp 101°–108° C.;

Cpd 90 7-Methoxy-2-(4-morpholinyl)-4H-1,3-benzoxazin-4-one, Mp 197°–200° C.; and Cpd 91 6-(Morpholin-1-yl)-pyrido(2,3-e)-1,3-oxazine-8-one, Mp 181°–184° C.

Following the general procedure of Example 83, but employing the appropriate o-hydroxy salicylic methyl ester in place of the methyl ester of 5-methylsalicylic acid and the appropriate heterocylic compound in place of morpholine there are prepared the following products:

Cpd 92 8-Methyl-2-(1-piperidinyl)-4H-1,3-benzoxazin-4-one, Mp 214.5°–217.5° C.;

Cpd 93 8-Methyl-2-(1-pyrrolidinyl)-4H-1,3-benzoxazin-4-one, Mp 199.5°–200.5° C.;

Cpd 94 2-(1-pyrrolidinyl)-4H-1,3-benzoxazin-4-one, Mp 163°–164° C.;

Cpd 95 2-(1-(4-Thiomorpholinyl))-4H-1,3-benzoxazin-4-one, Mp 179°–180° C.;

Cpd 96 2-(4-Methyl-1-piperazinyl)-4H-1,3-benzoxazin-4-one.

EXAMPLE 98

Preparation of 2-(4-Morpholinyl)-4H-1,3-benzoxazin-4-one, Compound 98 (Method A)

Methyl salicylate (25 g, 0.164 M) and BrCN (18.08 g, 0.172 M) is added to dry acetone (500 mL) and cooled to 0°

C. That mixture is then treated with TEA (17.37 g, 0.172M) in acetone (50 mL) dropwise over 20 minutes. A white precipitate separates from the solution. After stirring 1 hr the acetone is decanted and the precipitate washed with acetone. The filtrate is concentrated in vacuo and used without further purification. The above cyanoether (29.0 g, 0.164 M) is added to acetonitrile (300 mL) under an atmosphere of nitrogen. An acetonitrile solution of morpholine (14.26 g, 0.164 M) is then added dropwise over 30 minutes. The reaction becomes warm during addition. After stirring a total of 3 hrs the solvent is removed in vacuo to yield a tan solid which is washed with ether to yield 22 g (58%) of pure product. An analytical sample is prepared by recrystallization from EtOAc. MP 184.5°–86.0° C. (lit MP 187°–9° C.);[6] IR (CHCl$_3$) 2950, 2825, 2750, 1670, 1620, 1600, 1560, 1460, 1440, 1420, 1340, 1260, 1110, 980, 850 cm$^{-1}$; 1H-NMR (CDCl$_3$) 8.25 (dd, 1H, J=1.5 and 6.0 Hz), 7.8–7.2 (m, 3H, aromatic), 3.80 (s, 8H); Mass spectrum: ions at m/e (relative intensity) 232 (47), 215 (13), 204 (20), 189 (11), 176 (14), 175 (56), 121 (35), 120 (100), 92 (46), 64 (14); UV (EtOH) λ max (ε) 210 (24,000), 218 (24,200), 240 sh (11,200), 258 (14,750), 286 (4,850), 295 (3,900); Anal. calc'd. for C$_{12}$H$_{12}$N$_2$O$_3$: C, 62.06; H, 5.17; N, 12.06. Found: C, 61.70; H, 5.22; N, 11.99.

EXAMPLE 99

Preparation of 2-(4-Morpholinyl)-4H-1,3-benzoxazin-4-one, Compound 98 (Method B)

Tosic acid (0.4g, 2 mmol) is added to a solution of 2-mercapto-4H-1-benzopyran-4-one (3.56 g, 20 mmol) and piperidine (2.38 g, 2.77 ml, 28 mmol) in benzene (400ml). After refluxing for 5 hours, the reaction solution is evaporated in vacuo. The residue is transferred to a separatory funnel with methylene chloride and water. Extracting with methylene chloride, washing the organic layer twice with water, and filtering through sodium sulfate affords 2.80 g of crude material after evaporation of the solvent. Flash chromatography over silica gel (300 g, 7% MeOH/CH$_2$Cl$_2$) affords 0.39 g of 2-(4-Morpholinyl)-4H-1,3-benzoxazin-4-one.

EXAMPLE 101

2-(4-Morpholinyl)-7-(phenylmethoxy)-4H-1-benzopyran-4-one, Compound 101

Prepared by the method outlined in Chart C.

EXAMPLE 173

Preparation of 4'-Acetoxy-3'-methyl-2'-hydroxypropiophenone (Relating to Chart E)

Part A: 2',4'-Dihydroxy-3'methyl-propiophenone (7.21 g, 40 mmole) is suspended in 200ml dichloromethane in a 500 ml one neck round bottom flask under nitrogen. The suspension is treated with diisopropylethylamine (6.97 ml, 40 mmole) and the solution is cooled to 0° C. Acetyl chloride (3.26 ml, 46 mmole), in 80 ml dichloromethane, is added slowly dropwise to the reaction mixture (1 h) at 0 C. The mixture is warmed to room temperature and is stirred 20 min. The reaction is washed with 1×150 ml 5% hydrochloric acid and the organics are dried over magnesium sulfate. The mixture is concentrated in vacuo to a yellow oil which is crystallized and then recrystallized from ethanol to afford 7.2 g (81%) of the acetate as a white solid. Melting Point: 59°–61° C.

Part B: Preparation of 7-Acetoxy-3,8-dimethyl-2-(4-morpholinyl)-4H-1-benzopyran-4-one (Cpd 173)

4'-Acetoxy-2'-hydroxy-3'-methyl-propiophenone (6.2 g, 27.9 mmole) is dissolved in 60 ml diethyl ether in a 100 ml one neck round bottom flask under nitrogen. The solution is treated with boron trifluoride etherate and the reaction mixture is stirred overnight at room temperature. The precipitate is collected by filtration and is washed with 150 ml diethyl ether to afford 6.8 g (90%) of the boron difluoride complex as a yellow solid. The boron difluoride complex (1.05 g, 5.13 mmole) and 4-morpholine phosgene iminium chloride (1.25 g, 4.63 mmole) are combined in 12 ml 1,2-dichloroethanein a 25 ml one neck round bottom flask under nitrogen. The reaction mixture is warmed to 60 C for 3 h. The reaction is cooled to room temperature and the dichloroethane is removed in vacuo. The residual oil is taken up in 12ml acetonitrile in a 25 ml one neck round bottom flask. The mixture is warmed to 60° C., is diluted with 10 ml water, and is stirred for 5 min. The reaction mixture is immediately neutralized with 25 ml saturated sodium bicarbonate and the acetonitrile is removed in vacuo. The aqueous residue is extracted with 4×25 ml dichloromethane. The combined organics are dried over magnesium sulfate and are concentrated in vacuo to afford 750mg (51%) of Cpd 173 as an orange solid.

Melting Point: 142.5°–144.5° C.

Part C: Preparation of 3,8-dimethyl-7-hydroxy-2-(4-morpholinyl)-4H-1-benzopyran-4-one (Cpd 174)

The boron difluoride complex (prepared as in Part A above, 3.0 g, 11.1 mmole) is combined with 4-morpholine phosgene iminium chloride (2.5 g, 12.2 mmole) in 29 ml 1,2-dichloroethane in a 50 ml one neck round bottom flask under nitrogen. The reaction mixture is warmed to 60° C. for 3.5 h and is cooled to room temperature. The dichloroethane is removed in vacuo and the oily residue is dissolved in 30 ml acetonitrile in a 100 ml one neck round bottom flask under nitrogen. The solution is warmed to 60° C., is diluted with 25 ml water, and is stirred for 5 min. The reaction mixture is immediately quenched with 30 ml saturated sodium bicarbonate and the acetonitrile is removed in vacuo. The aqueous residue is extracted with 4×25 ml dichloromethane and the combined organics are dried over magnesium sulfate. The dried organics are concentrated in vacuo to a yellow solid (2.82 g) which is dissolved in 30 ml methanol in 100 ml one neck round bottom flask under nitrogen. The solution is diluted with 15 ml water and the mixture is treated with lithium hydroxide (800 mg, 19.1 mmole). The reaction mixture is stirred 1 h at room temperature. The methanol is removed in vacuo and the pH of the aqueous residue is adjusted to 5 with 5% hydrochloric acid (pH meter). The precipitated phenol is collected by filtration and is dried to afford 1.2g (40%) of Cpd 174. Melting Point: >300 C Part D: Preparation of 7-benzyloxy-3,8-dimethyl -2-(4-morpholinyl)-4H-1-benzopyran-4-one (Cpd 175).

3,8-Dimethyl-7-hydroxy-2-(4-morpholinyl)-4H-1-benzopyran-4one (355 mg, 1.29 mmole) is suspended in 9 ml dry acetonitrile in a 25 ml one neck round bottom flask under nitrogen. The suspension is treated successively with potassium carbonate (1.1 g, 8.0 mmole) and benzyl bromide (213 mg, 1.79 mmole). The reaction mixture is warmed to 60° C. for 16 h and is cooled to room temperature. The volatiles are removed in vacuo and the residue is washed with 25 ml dichloromethane. The insoluable material is removed by filtration and the filtrate is concentrated to a pale oil. The oil is crystallized from diethyl ether to afford 323 mg (69%) of Cpd 175 as a white solid. Melting Point: 136°–137.5° C.

Following the general procedure of Example 173, but starting with the appropriate 2'-hydroxypropiophenone, there are prepared the following products:

Cpd 176 3,8-Dimethyl-2-(4-morpholinyl)-7-(naphthyl-1-methyloxy)-4H-1-benzopyran-4-one, mp. 204–206;

Cpd 177 3,8-Dimethyl-7-(4-methoxy-benzyloxy)-2-(4-morpholinyl)-4H-1-benzopyran-4-one, mp. 141–142;

Cpd 178 3,8-Dimethyl-2-(4-morpholinyl)-7-(2-phenylethyloxy)-4H-1-benzopyran-4-one, mp. 160–161.5;

Cpd 179 3,8-Dimethyl-7-(4-chlorobenzyloxy)-2-(4-morpholinyl)-4H-1-benzopyran-4-one, mp. 166–167.5;

Cpd 180 3,8-Dimethyl-2-(4-morpholinyl)-7-(3-trifluoromethyl-benzyloxy)-4H-1-benzopyran-4-one, mp. 158.5–160;

Cpd 181 7-(Carbomethoxy-methoxyl)-3,8-dimethyl-2-(4-morpholinyl)-4H-1-benzopyran-4-one, mp. 174–175;

Cpd 182 8-Hydroxy-3-methyl-2-(4-morpholinyl)-4H-1-benzopyran-4-one, mp. 239–240;

Cpd 183 8-Benzyloxy-3-methyl-2-(4-morpholinyl)-4H-1-benzopyran-4-one, mp. 134–135;

Cpd 184 3-methyl-2-(4-morpholinyl)-8-(m-trifluoromethyl-benzyloxy)-4H-1-benzopyran-4-one, mp. 160.5–161.

EXAMPLE 185

Preparation of C-7 alkyl, alkenyl and alkynylaryl substituents. (relating to Chart F)

Part A: Preparation of 2'-Hydroxy-3'-methyl-4'-trifluormethanesulfonyloxy-acetophenone.

2',4'-Dihydroxy-3'methyl-acetophenone (11 g, 60.2 mmole) is suspended in 300 ml dichloromethane in a 1000 ml one neck round bottom flask under nitrogen. The suspension is treated successively with pyridine (4.4 ml, 54 mmole) and N,N, dimethylamino-pyridine (730 mg, 6 mmole) and the solution is cooled to 0° C. Triflic anhydride (11 ml, 66.2 mmole), in 1×100 ml dichloromethane, is added slowly dropwise to the reaction mixture (30 min). The reaction is stirred for 1 h at room temperature for 1 h and the mixture is washed with 2×200 ml 5% hydrochloric acid. The organics are dried over magnesium sulfate and are concentrated in vacuo to a yellow oil. The oil is distilled via kugelrhor under high vacuum (165 C) to provide 16.4 (91%) of triflate as a white solid. Melting Point: 60°–64° C.

Part B: Preparation of 8-methyl-2-(4-morpholinyl)-7-trifluormethanesulfonyloxy-4H-1-benzopyran-4-one.

2'-Hydroxy-3'-methyl-4'-triflouromethanesulfonyloxy-acetophenone (1.5 g, 5.03 mmole) is dissolved in 10 ml diethyl ether in a 25 ml one neck round bottom flask under nitrogen. The solution is treated with boron trifluoride etherate (0.9 ml, 7.5 mmole) and the reaction mixture is stirred for 6 h at room temperature. Approximately ½ the ether is removed in vacuo and the precipitate is collected by filtration. The pale solid is washed with cold diethyl ether to afford 1.1 g (63%) of difluoroboronate. Boron difluoride complex (1.1 g, 3.2 mmole) is combined with 4-morpholinophosgeniminium chloride (0.72 g, 3.5 mmole) in 12 ml 1,2-dichloroethane in a 50 ml one neck round bottom flask under nitrogen. The reaction mixture is warmed to 65° C. for 3 h and is cooled to room temperature. The precipitate is removed by filtration and is washed with diethyl ether to provide 1.35 g. The solid is suspended in 12 ml acetonitrile in a 25 ml one neck round bottom flask under nitrogen. The suspension is stirred with 1.2 ml water for 48 h. The colorless solution is diluted with 10 ml saturated sodium bicarbonate and the acetonitrile is removed in vacuo. The aqueous residue is extracted with 4×25 ml dichloromethane. The combined organics are dried over magnesium sulfate and are concentrated in vacuo to a red solid. The solid is recrystallized from ethyl acetate to afford 566 mg (45%) of chromone-triflate as an off white solid. Melting Point: 151°–155° C.

Part C: Preparation of 8-methyl-7-(2-phenyl)ethynyl-2-(4-morpholinyl)-4H-1-benzopyran-4-one (Cpd 185).

8-Methyl-7-(trifluoromethanesulfonyloxy)-2-(4-morpholinyl)-4H-1-benzopyran-4-one (190 mg, 0.48 mmole) is suspended in 6 ml 1:1 benzene/triethylamine in a 15 ml screw cap pressure tube. The suspension is treated successively with phenyl acetylene (100 ul, 0.91 mmole), his (triphenylphosphine) palladium dichloride (14 mg, 0.02 mmole), and cuprous iodide (2 mg, 0.01 mmole). The reaction mixture is warmed to 100°–110° C. overnight. The reaction mixture is cooled to room temperature and is again treated successively with phenyl acetylene (100 ul, 0.91 mmole), bis (triphenylphosphine) palladium dichloride (14 mg, 0.02 mole), and cuprous iodide (2 mg, 0.01 mmole). The reaction is heated to 110° C. for 4 h and is cooled to room temperature. The volatiles are removed in vacuo to a black residue. The residue is chromatographed over 12 g silica gel (230–400 mesh)eluting with 1% methanol/dichloromethane and collecting 3 ml fraction s for 48 fractions. Thereafter elution is carried out with 2% methanol/dichloromethane and 5 ml fractions are collected. Fractions 55–72 are combined and concentrated to provide 153 mg of a dark brown solid. The solid is recrystallized from ethyl acetate to afford 94 mg (56%) of Cpd 185 as a pale grey solid. Melting Point: 228.5°–229.5° C.

EXAMPLE 186

Preparation of 8-methyl-2-(4-morpholinyl)-7-(2-phenyl)ethyl-4H-1-benzopyran-4-one (Cpd 186).

8-Methyl-2-(4-morpholinyl)-7-(2-phenyl-ethynyl)-4H-1-benzopyran-4-one (90 mg, 0.261 mmole) is dissolved in 90 ml 8:1 methanol/acetone in a Parr shaker bottle. The solution is treated with 18 mg 10% palladium on carbon and the reaction mixture is hydrogenated at 40 PSI for 2 h. The catalyst is removed by filtration through a 1" bed of celite and the filter cake is washed well with methanol. The filtrate is concentrated in vacuo to a yellow oil which crystallized from hexane to give 70 mg (77%) of Cpd 186 as a tan solid. Melting Point: 162°–163° C.

Following the general procedures of Example 185, but starting with the appropriate 2'-hydroxyacetophenone, there are prepared the following products:

Cpd 187 2-(4-Morpholinyl)-8-(2-phenyl)ethynyl-4H-1-benzopyran-4-one, mp. 196–197;

Cpd 188 2-(4-Morpholinyl)-8-(2-phenyl)ethyl-4H-1-benzopyran-4-one, mp. 110–112;

Cpd 189 2-(4-Morpholinyl)-8-(2-(3-trifluoromethyl) phenyl)ethynyl-4H-1-benzopyran-4-one, mp. 157.5–158.5;

Cpd 190 2-(4-Morpholinyl)-8-(2-(3-trifluoromethyl-) phenyl)ethyl-4H-1-benzopyran-4-one, mp. 130–131;

Cpd 192 8-Methyl-2-(4-morpholinyl)-7-(2-(1-naphthyl)) ethyl-4H-1-benzopyran-4-one, mp. 188.5–189.5;

Cpd 193 8-Methyl-2-(4-morpholinyl)-7-phenyl-4H-1-benzopyran-4-one, mp. 194.5–195.

EXAMPLE 194

Relating to Chart G

Part A: Preparation of 4'-acetoxy-3'-iodo-2'-hydroxypropiophenone

2',4'-dihydroxy-3'-iodoacetophenone (55.6 g, 0.2 mol) is suspended in 600 ml of methylene chloride. Triethylamine (27.8 ml, 0.2 mol) is added and the cooled mixture (0° C.) is treated dropwise with acetyl chloride (16.35 ml, 0.23 mol). The mixture is stirred at 0° C. for 1 h and at ambient temperature for 2 h. The mixture is washed with 5% hydrochloric acid, dried owver magnesium sulfate and evaporated. The solid is recrystallized from ethanol to provide 48.39 g of the product.

Part B: Preparation of 7-acetyloxy-8-iodo-2-(4-morpholinyl)-4H-1-benzopyran-4-one (Cpd 194)

4'-Acetoxy-3'-iodo-2'-hydroxy-propiophenone (48.4 g, 0.15 mol) is suspended in 750 ml of ether and treated with boron trifluoride etherate (27.9 ml, 0.22 mol). The mixture is stirred overnight at ambient temperature, filtered and the solid is washed well with ether to afford 47.0 g of the boron difluoride complex. The complex is combined with 4-morpholine dichloromethyleniminium chloride in 400 ml of ethylene dichloride and heated at 70° C. for 5 h and at 50° C. for 16 h. The reaction is cooled to 0° C. and the solid is filtered and washed well with ether (45 g). The solid is suspended in 400 ml of acetonitrile, 40 ml of water is added and the mixture is stirred overnight at room temperature, heated at 50° C. for 2 h and finally heated at 60° C. for 30 min. The solvent is evaporated and the material is taken up in methylene chloride/saturated sodium bicarbonate. The aqueous layer is extracted twice with methylene chloride and the combined organics are dried over magnesium sulfate. Evaporation of the solvent and recrystallization from methanol gave 20.8 g (39%) of the chromone. The mother liquors contained 5.8 g of crude product from which a second recrystallization yielded 0.7 g. mp. 201.5–202.5

Part C: Preparation of 8-ethyl-7-hydroxy-2-(4-morpholinyl)-4H-1-benzopyran-4-one 7-Acetyloxy-8-iodo-2-(4-morpholinyl)-4H-1-benzopyran-4-one (2.07 g, 5.0 mmol) is combined with lithium chloride (0.64 g, 15 mmol) tetraethyltin (1.04 ml, 5.25 mmol) and (bis)triphenylphosphine palladium dichloride (70 mg, 0.10 mmol) in 20 ml of dimethylformamide. The mixture is heated a 100° C. for 40 min., poured into half saturated sodium chloride and extracted twice with methylene chloride. The organics are washed twice with half saturated sodium chloride, dried over magnesium sulfate and evaporated. The material is taken up in 20 ml of methanol and 10 ml of water and treated with 0.63 g (15 mmol) of lithium hydroxide. The mixture is stirred at room temperature for 30 min. The solvent is evaporated, the mixture is diluted with water and extracted twice with ethyl acetate. The aqueous layer is acidified to pH 6.1 with 5% hydrochloric acid and the solid is filtered, washed with ether and dried to afford 0.98 g (71%) of the product.

Part D: Preparation of 8-ethyl-2-(4-morpholinyl) -7-(3-pyrindinylmethoxy)-4H-1-benzopyran-4-one (Cpd 195)

8-Ethyl-7-hydroxy-2-(4-morpholinyl)-4H-1-benzopyran-4-one (0.176 g, 0.64 mmol) and sodium hydride (0.105 g, 60%, 2.6 mmol) are combine in 4 ml of dimethylformamide and heated to 60° C. for 20 min. 3-Picoyl chloride hydrochloride (0.321 g, 1.76 mmol) is added and the mixture is heated at 60° C. for 1 h. The cooled mixture is poured into 2N sodium hydroxide and ice. The solid is filtered, washed well with water and ether and recrystallized form ethyl acetate to provide 0.156 g of the product. mp. 178–179.

Following the general procedure of Example 194, but starting with the appropriate 2'-hydroxyacetophonone, there are prepared the following products:

Cpd 196 8-Ethyl-2-(4-morpholinyl)-7-phenylmethoxy-4H-1-benzopyran-4-one, mp. 153–154.5;

Cpd 197 8-Iodo-2-(4-morpholinyl)-7-phenylmethoxy-4H-1-benzopyran-4-one, mp. 155–157;

Cpd 198 8-Ethyl-2-(4-morpholinyl)-7-(2-(1-piperidinyl) ethyl) oxy-4H-1-benzopyran-4-one, mp. 151–152;

Cpd 199 8-Iodo-2-(4-morpholinyl)-7-(3-pyrindinylmethoxy)-4H-1-benzopyran-4-one, mp. 214–215;

Cpd 200 8-Iodo-7-hydroxy-2-(4-morpholinyl)-4H-1-benzopyran-4-one, mp. 224–225;

Cpd 217 2-(4-Morpholinyl)-7-phenylmethoxy-8-vinyl-4H-1-benzopyran-4-one, mp. 181–182.5;

Cpd 218 2-(4-Morpholinyl)-8-phenyl-7-phenylmethoxy-4H-1-benzopyran-4-one, mp. 178.5–180.5.

Cpd 280 8-ethyl-2-(4-morpholinyl)-7-[2-(4-phenyl-1-piperidinyl)ethoxy]-4H-1-Benzopyran-4-one, mp. 178–179;

Cpd 281 (R)-8-ethyl-7-[2-[2-(hydroxymethyl)-1-pyrrolidinyl]ethoxy]-2-(4-morpholinyl)-4H-1-Benzopyran-4-one, mp. 127–128.5;

Cpd 282 8-ethyl-2-(4-morpholinyl)-7-[2-(4-thiomorpholinyl)ethoxy]-4H-1-Benzopyran-4-one, mp. 151.5–153.5;

Cpd 283 8-ethyl-7-[2-(4-methyl-1-piperazinyl)ethoxy]-2-(4-morpholinyl)-4H-1-Benzopyran-4-one, mp. 124–124.5;

Cpd 326 8-ethenyl-7-[2-(4-methyl-1-piperazinyl)ethoxy]-2-(4-morpholinyl)-4H-1-Benzopyran-4-one, mp. 151–152;

Cpd 327 8-ethenyl-2-(4-morpholinyl)-7-[2-(1-piperidinyl)ethoxy]-4H-1-Benzopyran-4-one, mp. 161–162;

Cpd 328 8-ethenyl-1-(4-morpholinyl)-7-[2-(4-phenyl-1-piperidinyl)ethoxy]-4H-1-Benzopyran-4-one, mp. 169–169.5;

Cpd 329 8-ethenyl-2-(4-morpholinyl)-7-[2-(1-pyrrolidinyl)ethoxy]-4H-1-Benzopyran-4-one, mp. 155–156;

Cpd 330 8-ethenyl-2-(4-morpholinyl)-7-[2-(4-thiomorpholinyl)ethoxy]-4H-1-Benzopyran-4-one, mp. 210.5–211.5; and Cpd 331 (R)-8-ethenyl-7-[2-[2-(hydroxymethyl)-1-pyrrolidinyl]ethoxy]-2-(4-morpholinyl) -4H-1-Benzopyran-4-one, mp. 115–117.

EXAMPLE 201

Relating to Chart H

Part A: Preparation of 7-hydroxy-8-methyl-2-(1-piperidinyl)-4H-1-benzopyran-4-one (Cpd 201).

Palladium black (225 mg) is added to a solution of the benzyl ether Cpd 31 (1.00 g, 2.86 mmol) in EtOAc (80 ml). After shaking in a Parr hydrogenation apparatus under 50 lbs pressure of hydrogen for 2 days, the catalyst is filtered off through a cintered glass funnel rinsing with EtOAc and MeOH. Evaporation of the solvent afforded 0.99 g of crude material. Flash chromatography (60 g silica gel, 10% MeOH/CH$_2$Cl$_2$) afforded 0.83 g of the phenol. Recrystallization from MeOH/EtOAc at 4° C. afforded 0.65 g (88%) of white crystalline title product. mp 278°–284° C.

Part B: Preparation of 7-(3-pyridinylmethoxy)-2-(1-piperidinyl)-8-methyl-4H-1-benzopyran-4-one, Cpd 202.

A suspension of phenol Cpd 170 (130 mg, 0.5 mmol), 3-picolinyl chloride-HCl (161 mg, 1.0 mmol), and potassium carbonate (277 mg, 2.0 mmol) in dimethylformamide (5 ml) is stirred at 90° C. After 7 days, the reaction mixture is evaporated down and then CHCl$_3$ added. The solids are filtered off and the filtrate evaporated. Flash chromatography of the residue (15 g silica gel, 2% MeOH/CH$_2$Cl$_2$, 6 ml fractions) afforded 18 mg (10%, fractions 37–52) of Cpd202. mp 144°–58° C.

EXAMPLE 203

Preparation of 7-phenylmethoxy-2-methylthiomethyl -8-methyl-4H-1-benzopyran-4-one, Cpd 203 (Relating to Chart I)

Part A: Sodium hydride (50% oil dispersion washed 3× in hexane, 23.2 g, 0.48 mol) is stirred in THF (195 ml) under nitrogen in a flame dried 2 1 three-necked round bottom flask equipped with an addition funnel and a condensor. A solution of the 2-hydroxyacetophenone (25 g, 97.6 mmol) and ethyl α-thiomethyl-acetate (130.4 g, 123 ml, 0.9 mol) in THF (164 ml) is slowly dropped into the sodium hydride slurry. After about half of the reagent solution had been added the reaction is heated with a heating gun until the reaction had begun to reflux on its own. The remainder of the reagent solution is slowly added with stirring. After 10 min at ambient temperature and 1 h 40 min at reflux, the solution is evaporated in vacuo. The solution is transferred to a separatory funnel with methylene chloride/2N HCl and shaken for about 10 min. Extraction with methylene chloride (2×) and drying over magnesium sulfate affords the crude β-diketone which is not further purified.

A biphasic solution of the β-dikeone and 6N HCl (250 ml) is stirred at ambient temperature overnight. Extraction with methylene chloride and drying over magnesium sulfate afforded 127.13 g of crude material after evaporation of the solvent. Flash chromatography (700 g silica gel, 30–50% EtOAc/hexane) afforded 122 g of a mixture of the starting acetophenone, the thiomethylacetate, and some β-diketone and 4.94 g Cpd 203 (15%). An analytical sample is recrystallized from ether/hexane to afford white crystalline title product. mp 110°–114° C.

Part B: Preparation of 7-phenylmethoxy-2-iodomethyl-8-methyl-4H-1-benzopyran-4-one A solution of Cpd 203 (4.0 g, 12.3 mmol) in methyl iodide (12.5 ml) and CH$_2$Cl$_2$ (8 ml) is stirred under reflux. After 3 days, the solution is cooled to 0° C. and the yellow precipitate filtered off. The filtrate is evaporated down and the residue flash chromatographed (100 g silica gel, 40% EtOAc/hexane) to afford 1.48 g of 7-phenylmethoxy-2-iodomethyl-8-methyl-4H-1-benzopyran-4-one (30%). An analytical sample is prepared by recrystallization from CH$_2$Cl$_2$/EtOAc/hexane to afford white crystalline title product. mp 144°≧7° C.;

Part C: Preparation of 8-Methyl-2-(4-morpholinylmethyl)-7-(phenylmethoxy)-4H-1-benzopyran-4-one (Cpd 204)

Morpholine (0.21 g, 2.5 mmol) is added to a stirring solution of 7-phenylmethoxy-2-iodomethyl-8-methyl-4H-1-benzopyran-4-one (1.0 g, 2.5 mmol) and triethylamine (0.25 ml, 2.5 mmol) in CHCl$_3$ (12 ml). After stirring at ambient temperature for 2.5 h, the solvent is evaporated in vacuo. The residue is flash chromatographed (100 g silica gel, 50–100% EtOAc/CH$_2$Cl$_2$, 45 ml fractions) to afford 0.72 g (79%) of the product. Recrystallization from ether afforded a white solid title product. MP 130°–3° C.

Part D: Preparation of 7-hydroxy-2-(4-morpholinylmethyl)-8-methyl -4H-1-benzopyran-4-one, Cpd 205

Palladium black (140 mg) is added to a solution of the benzyl ether Cpd 204 (0.65 g, 1.78 mmol) in EtOAc (50 ml). After shaking in a Parr hydrogenation apparatus under 50 lbs pressure of hydrogen for 23 h, the catalyst is filtered off through a cintered glass funnel rinsing with EtOAc and MeOH. Evaporation of the solvent afforded 0.49 g of crude material. Flash chromatography (100 g silica gel, 4% MeOH/CH$_2$Cl$_2$, 50 ml fractions) afforded 35 mg (5%, fractions 6–7) of the starting material and 0.33 g (68%, fractions 11–16) of the phenol. An analytical sample is prepared by recrystallization from EtOAc/ether/hexane at 4° C. to afford white crystalline title product. MP 144°–6° C.

Part E: Preparation of 7-[(1-cyclohexyl-1H-tetrazol-5-yl)methyoxy]-8-methyl-2-(4-morpholinylmethy)-4H-1-benzopyran-4-one, Cpd 206

A suspension of Cpd 205 (100 mg, 0.36 mmol), 5-(4-chloromethyl)-1-cyclohexyltetrazole [see e.g. Chem. Pharm. Bull. 31, 1151 (1983)] (146 mg, 0.73 mmol), and potassium carbonate (201 mg, 1.45 mmol) in acetonitrile (3 ml) is stirred at 60° C. After 17 h, the reaction mixture is evaporated down and then CHCl$_3$ added. The solids are filtered off and the filtrate evaporated. Flash chromatography of the residue (25 g silica gel, 3% MeOH/CH$_2$Cl$_2$, 15 ml fractions) afforded 134 mg (85%, fractions 5–6) of white crystalline title product. MP 193°–5° C.

Part F: Preparation of 8-Methyl-2-(4-morpholinylmethyl)-7-(3-pyridinylmethoxy)-4H-1-benzopyran-4-one, Cpd 207

A suspension of Cpd 205 (50 mg, 0.18 mmol), 3-picolinyl chloride-HCl (58 mg, 0.36 mmol), and potassium carbonate (100 mg, 0.72 mmol) in acetonitrile (2 ml) is stirred at 60° C. After 2 days, the reaction mixture is evaporated down and then CHCl$_3$ added. The solids are filtered off and the filtrate evaporated. Flash chromatography of the residue (20 g silica gel, 3% MeOH/CH$_2$Cl$_2$, 10 ml fractions) afforded 45 mg (68%, fractions 17–25) of white crystalline title product which is recrystallized from ether. mp 105°–8° C.

EXAMPLE 208

Preparation of 7-(2-Bromoethyl)oxy-8-methyl -2-(4-morpholinyl)-4H-1-benzopyran-4-one(Relating to Chart J)

Part A: Cpd 39 (13.1 g) is suspended in 150 ml of 50% sodium hydroxide in a 500 ml flask. The mixture is treated successively with 2.8 g (8.2 mmol) tetrabutylammonium hydrogen sulfate and 50 ml (0.58 mol) of 1,2-dibromoethane. The reaction mixture is warmed to 60° C. for 2h and cooled to 0° C. The solid is collected and washed well with 2N NaOH, water and ether. The material is dissolved in chloroform, adsorbed onto 30 g of silica gel (230–400 mesh) and chromatographed over 400 g silica gel, eluting with 4% methanol/methylene chloride to afford 8.1 g (40%) of 7-(2-Bromoethyl)oxy-8-methyl-2-(4-morpholinyl) -4H-1-benzopyran-4-one, mp 210°–211.5° C.

Part B: Preparation of 7-[2-(4-Methyl-1-piperazinyl) ethyl]oxy-8-methyl -2-(4-morpholinyl)-4H-1-benzopyran-4-one (Cpd 208)

7-(2-Bromoethyl)oxy-8-methyl-2-(4-morpholinyl)-4H-1-benzopyran-4-one (4.0 g, 10.9 mmol) is suspended in 10 ml chloroform and 7 ml of N-methyl piperazine is added. The reaction is warmed to reflux for 5h and cooled to room temperature. The mixture is partitioned between 50 ml of 1:1 2N NaOH/saturated NaCl and 25 ml of methylene chloride. The combined organics were dried over magnesium sulfate, concentrated in vacuo, and chromatographed over 80 g silica gel, eluting with 15% methanol/dichlormethane to afford 3.5 g (83%) of cpd 208, mp. 159–159.5, after recrystallization from ethyl acetate.

Following the general procedure of Example 208 (Part B), using 7-(2-bromoethyl)oxy-8-methyl-2-(4-morpholinyl)-4H-1-benzopyran-4-one but employing the appropriate amine or sulfide nucleophile, there are prepared the following products:

Cpd 209 7-(2-(2-Hydroxymethylpiperidin-1-yl) ethyl) oxy-8-methyl-2-(4-morpholinyl)-4H-1-benzopyran-4-one, mp. 142–144;

Cpd 210 7-(2-(3-Hydroxymethylpiperidin-1-yl)ethyl) oxy-8-methyl-2-(4-morpholinyl)-4H-1-benzopyran-4-one, mp. 143–145;

Cpd 211 7-(2-(2-Carboethoxypiperidin-1-yl) ethyl)oxy-8-methyl-2-(4-morpholinyl)-4H-1-benzopyran-4-one, mp. 91.5–92.5;

Cpd 212 7-(2-(3-Carboethoxypiperidin-1-yl)ethyl) oxy-8-methyl-2-(4-morpholinyl)-4H-1-benzopyran-4-one, mp. 113–115;

Cpd 213 8-Methyl-7-(2-(2-methylpiperidin -1-yl)ethyl) oxy -2-(4-morpholinyl)-4H-1-benzopyran-4-one, mp. 108–110;

Cpd 214 7-(2-(3-Carboxypiperidin-1-yl)ethyl)oxy-8-methyl-2-(4-morpholinyl)-4 H-1-benzopyran-4-one, mp. 226.5–228.5;

Cpd 215 8-Methyl-2-(4-morpholinyl)-7-[2-(1-piperazinyl)ethyl]oxy-4H-1-benzopyran-4-one, mp. 112–114;

Cpd 220 8-Methyl-2-(4-morpholinyl)-7-[2-(4-(2-hydroxy)ethyl-1-piperazinyl)ethyl]oxy-4H-1-benzopyran-4-one, mp. 192.5–193.5;

Cpd 223 8-Methyl-2-(4-morpholinyl)-7-[2-(2-thiopyrindinyl)ethyl]oxy-4H-1-benzopyran-4-one, mp. 146–147;

Cpd 224 8-Methyl-2-(4-morpholinyl)-7-[2-(4-thiopyrindinyl)ethyl]oxy-4H-1-benzopyran-4-one, mp. 211.5–212;

Cpd225 7-[2-(4-(2-Ethoxyphenyl)-1-piperazinyl)ethyl] oxy-8-methyl-2-(4-morpholinyl)-4H-1-benzopyran-4-one, mp. 158–159;

Cpd 226 8-Methyl-7-[2-((1-Methyl-1,3-imidazol-2-yl)thio)ethyl]oxy-2-(4-morpholinyl)-4H-1-benzopyran-4-one, mp. 170–170.5;

Cpd 227 7-[2-((Bis-N,N'-(2-methoxy)ethoxy)amino) ethyl]oxy-8-methyl-2-(4-morpholinyl)-4H-1-benzopyran-4-one, mp. 88–89;

Cpd 228 8-Methyl-7-[2-((4-Methyl-1,2,4-triazol-3-yl)thio)ethyl]oxy-2-(4-morpholinyl)-4H-1-benzopyran-4-one, mp. 221–221.5;

Cpd 229 7-[2-(N-Ethyl-N'-((2-hydroxy)ethyl)amino) ethyl]oxy-8-methyl-2-(4-morpholinyl) -4H-1-benzopyran-4-one, mp. 144–145;

Cpd 230 8-Methyl-7-[2-((1-Methyl-5-tetrazoyl)thio) ethyl]oxy-2-(4-morpholinyl)-4H-1-benzopyran-4-one, mp. 188.5–189.5;

Cpd 231 8-Methyl-2-(4-morpholinyl)-7-[2-((2-pyrimidinyl)thio)ethyl]oxy-4H-1-benzopyran-4-one, mp. 202.5–203.5;

Cpd 232 8-Methyl-2-(4-morpholinyl)-7-[2-(4-(2-pyridinyl)-1-piperazinyl)ethyl]oxy-4H-1-benzopyran-4-one, mp. 207–208;

Cpd 233 8-Methyl-2-(4-morpholinyl)-7-[2-(4-thiomorpholinyl)ethyl]oxy-4H-1-benzopyran-4-one, mp. 207.5;

Cpd 234 7-[2-((2-(Bis-N,N'-diethylamino)ethyl)thio) ethyl]oxy-8-Methyl-2-(4-morpholinyl)-4H-1-benzopyran-4-one, mp. 101–103;

Cpd 235 8-Methyl-7-[2-((2-benzoxazolyl)thio)ethyl]oxy-2-(4-morpholinyl) -4H-1-benzopyran-4-one, mp. 221–222;

Cpd 236 8-Methyl-7-[2-((2-benzothiazolyl)thio) ethyl] oxy-2-(4-morpholinyl)-4H-1-benzopyran-4-one, mp. 185.5–187;

Cpd 237 7-[2-(4-(3-Ethylamino-pyridin-2-yl)-1-piperazinyl)ethyl]oxy-8-methyl-2-(4-morpholinyl)-4H-1-benzopyran-4-one, mp. 168–169;

Cpd 238 8-Methyl-2-(4-morpholinyl)-7-[2-(pyrrolidinone-1-yl)ethyl]oxy-4H-1-benzopyran-4-one, mp. 144.5–145.5;

Cpd 163 8-Methyl-2-(4-morpholinyl)-7-(2-(1-piperidinyl) ethyl)oxy-4H-1-benzopyran-4-one, mp. 154–156;

Cpd 335 8-methyl-2-(4-morpholinyl)-7-[2-(phenylthio) ethoxy]-4H-1-Benzopyran-4-one, mp. 158–159;

Cpd 242 2-(4-morpholinyl)-8-[2-(2-pyridinylthio) ethoxy]-4H-1-Benzopyran-4-one, mp. 148–149;

Cpd 243 8-[2-[4-(2-ethoxyphenyl)-1-piperazinyl]ethoxy]-2-(4-morpholinyl)-4H-1-Benzopyran-4-one, mp. 133–134;

Cpd 244 8-[2-[4-[3-(ethylamino)-2-pyridinyl]-1-piperazinyl]ethoxy]-2-(4-morpholinyl)-4H-1-Benzopyran-4-one, mp. 122–123;

Cpd 245 2-(4-morpholinyl)-8-[2-(1-piperidinyl)ethoxy]-4H-1-Benzopyran-4-one, mp. 127.5–128.5;

Cpd 246 8-methyl-2-(4-morpholinyl)-7-[2-(phenylsulfinyl)ethoxy]-4H-1-Benzopyran-4-one, mp. 202–203;

Cpd 247 7-[2-[bis(2-pyridinylmethyl)amino]ethoxy]-8-methyl-2-(4-morpholinyl)-4H-1-Benzopyran-4-one, mp. 106–108;

Cpd 248 (S)-7-[2-[2-(hydroxymethyl)-1-pyrrolidinyl] ethoxy]-8-methyl -2-(4-morpholinyl)-4H-1-Benzopyran-4-one, mp. 138–139;

Cpd 249 7-[2-[b is [(4-methoxyphenyl)methyl]amino] ethoxy]-8-methyl-2-(4-morpholinyl)-4H-1-Benzopyran-4-one, mp. 117–119;

Cpd 250 8-methyl-2-(4-morpholinyl)-7-[2-(3-thiazolindinyl)ethoxy]-4H-1-Benzopyran-4-one, mp. 158–160.5;

Cpd 253 7-[2-[(2-methoxyphenyl)thio]ethoxy]-8-methyl-2-(4-morpholinyl)-4H-1-Benzopyran-4-one, mp. 155–156;

Cpd 255 7-[2-(hexahydro-1H-azepin-1-yl)ethoxy]-8-methyl-2-(4-morpholinyl)-4H-1-Benzopyran-4-one, mp. 153–154;

Cpd 256 8-methyl -2-(4-morpholinyl)-7-[2-(4-phenyl-1-piperazinyl)ethoxy]-4H-1-Benzopyran-4-one, mp. 242.5–243.5;

Cpd 257 8-methyl-2-(4-morpholinyl)-7-[2-(4-phenyl-1-piperidinyl)ethoxy]-4H-1-Benzopyran-4-one, mp. 177–178;

Cpd 258 (R)-7-[2-[2-(hydroxymethyl)-1-pyrrolidinyl]ethoxy]-8-methyl-3-(4-morpholinyl)-4H-1-Benzopyran-4-one, mp. 132–134;

Cpd 259 7-[2-(3-hydroxy-1-pyrrolidinyl)ethoxy]-8-methy]-2-(4-morpholinyl)-4H-1-Benzopyran-4-one, mp. 160–161;

Cpd 260 7-[2-[4-(2-chlorophenyl)-1-piperazinyl]ethoxy]-8-methyl-2-(4-morpholinyl) -4H-1-Benzopyran-4-one, mp. 171–172;

Cpd 261 2-(4-morpholinyl)-8-[2-(4-phenyl-1-piperidinyl)ethoxy]-4H-1-Benzopyran-4-one, mp. 138–139;

Cpd 268 8-methyl-7-[2-[methyl [2-(2-pyridinyl)ethyl]amino]ethoxy]-2-(4-morpholinyl)-4H-1-Benzopyran-4-one, mp. 83–84;

Cpd 269 8-methyl-2-(4-morpholinyl)-7-[2-(2-pyridinyloxy)ethoxy]-4H-1-Benzopyran-4-one, mp. 175–175.5;

Cpd 272 6-chloro-8-methyl-7-[2-(4-methyl-1-piperazinyl)ethoxy]-2-(4-morpholinyl)-4H-1-Benzopyran-4-one, mp. 155–156;

Cpd 279 8-ethyl-2-(4-morpholinyl)-7-[2-(1-pyrrolidinyl)ethoxy]-4H-1-Benzopyran-4-one, mp. 144–145;

Cpd 285 7-[2-(3,4-dihydro-2 (1H)-isoquinolinyl)ethoxy]-8-methyl-2-(4-morpholinyl)-4H-1-Benzopyran-4-one, mp. 143–144;

Cpd 295 8-[2-(3,4-dihydro-2 (1H)-isoquinolinyl)ethoxy]-2-(4-morpholinyl)-4H-1-Benzopyran-4-one, mp. 157–158;

Cpd 296 2-(4-morpholinyl)-8-[2-[4-(phenylmethyl)-1-piperazinyl]ethoxy]-4H-1-Benzopyran-4-one, mp. 151.5–152.5;

Cpd 297 8-[2-[4-[(4-chlorophenyl)phenylmethyl]-1-piperazinyl]ethoxy]-2-(4-morpholinyl)-4H-1-Benzopyran-4-one, mp. 167–168;

Cpd 304 8-[2-(ethylphenylamino)ethoxyl]-2-(4-morpholinyl)-4H-1-Benzopyran-4-one, mp. 127–128;

Cpd 306 1-[2-[[2-(4-morpholinyl)-4-oxo-4H-1-benzopyran-8-yl]oxy]ethyl]-3-Piperidinecarboxylic acid ethyl ester, mp. 83–85;

Cpd 307 1-[2-[[2-(4-morpholinyl)-4-oxo-4H-1-benzopyran-8-yl]oxy]ethyl]-2-Piperidinecarboxylic acid ethyl ester, mp. 119–120;

Cpd 309 6,8-dimethyl-7-[2-(4-methyl-1-piperazinyl)ethoxy]-2-(4-morpholinyl)-4H-1-Benzopyran-4-one, mp. 135–136.5;

Cpd 310 6,8-dimethyl-2-(4-morpholinyl)-7-[2-(1-piperidinyl)ethoxy]-4H-1-Benzopyran-4-one, mp. 139.5–140.5;

Cpd 311 6,8-dimethyl -2-(4-morpholinyl)-7-[2-(1-pyrrolindinyl)ethoxy]-4H-1-Benzopyran-4-one, mp. 144–145;

Cpd 314 6-iodo-8-methyl-2-(4-morpholinyl)-7-[2-(1-pyrrolidinyl)ethoxy]-4H-1-Benzopyran-4-one, mp. 171–172;

Cpd 315 6-iodo-8-methyl-2-(4-morpholinyl)-7-[2-(1-piperidinyl)ethoxy]-4H-1-Benzopyran-4-one, mp. 170–171;

Cpd 316 6-iodo-8-methyl-7-[2-(4-methyl-1-piperazinyl)ethoxy]-2-(4-morpholinyl)-4H-1-Benzopyran-4-one, mp. 174–175;

Cpd 317 6-bromo-8-methyl-2-(4-morpholinyl)-7-[2-(1-pyrrolidinyl)ethoxy]-4H-1-Benzopyran-4-one, mp. 171–172;

Cpd 318 6-bormo-8-methyl-2-(4-morpholinyl)-7-[2-(1-piperidinyl)ethoxy]-4H-1-Benzopyran-4-one, mp. 175–176;

Cpd 319 6-bromo-8-methyl-7-[2-(4-methyl-1-piperazinyl)ethoxy]-2-(4-morpholinyl)-4H-1-Benzopyran-4-one, mp. 162–163;

Cpd 332 2-(4-morpholinyl)-8-[2-(4-thiomorophlinyl)-ethoxy]-4H-1-Benzopyran-4-one, mp. 160.5–161.5;

Cpd 347 7-[2-(4-Ethyl-1-piperazinyl)ethyl]oxy-8-methyl-2-(4-morpholinyl)-4H-1-benzopyran-4-one, mp. 144.5–145.5.

EXAMPLE 239

Preparation of 7-[2-(4-Methyl-1-piperazinyl)ethyl] oxy-8-methyl-2-(4-morpholinyl)-4H-1-benzopyran-4-one, mesylate salt Compound 239.

7-[2-(4-Methyl-1-piperazinyl)ethyl]oxy-8-methyl-2-(4-morpholinyl) -4H-1-benzopyran-4-one, Cpd 208 (2.0 g, 5.16 mmol) is dissolved in 25 ml of methylene chloride under nitrogen. The solution is diluted with 5 ml of methanol and treated with 0.335 ml (5.16 mmol) of methanesulfonic acid. The mixture is concentrated in vacuo to a residual foam. The foam is crystallized from 25 ml of ethyl acetate and allowed to digest overnight. The off-white solid is collected, washed with ether and dried in vacuo for 6h at room temperature and for 24h at 50 C to afford 2.48 g (99%) of the title salt (mp. 207.5–208.5)

Following the general procedure of example 239, the following salts were prepared:

Cpd 240 8-Methyl-2-(4-morpholinyl)-7-(2-(1-piperidinyl)ethyl)oxy-4H-1-benzopyran-4-one, mesylate salt, Mp. 151–153;

Cpd 241 8-Methyl-2-(4-morpholinyl)-7-(3-pyridinyl) methyl)oxy-4H-1-benzopyran-4-one, mesylate salt, Mp. 222–223.

Cpd 336 8-Methyl-2-(4-morpholinyl)-7-(2-pyridinylmethoxy )-4H-1-benzopyran-4-one, mesylate salt, mp. 175–176;

Cpd 337 8-Methyl-2-(4-morpholinyl)-7-(2-pyridinylmethoxy)-4 H-1-benzopyran-4-one, bismesylate salt, mp. 211–212;

Cpd 338 8-Methyl-2-(4-morpholinyl)-7-(3-pyrindinylmethoxy)-4H-1-benzopyran-4-one, bismesylate salt, mp. 218–220;

Cpd 339 7-[(1-cyclohexyl-1H-tetrazol-5-yl)methoxy]-8-methyl-2-(4-morpholinyl)-4H-1-Benzopyran-4-one, mesylate salt, mp.>250;

Cpd 340 8-Methyl-2-(4-morpholinyl)-7-(2-(1-pyrrolidinyl)ethyl)oxy-4H-1-benzopyran-4-one, mesylate salt, mp. 215–217;

Cpd 341 8-Methyl-2-(4-morpholinyl)-7-[2-(1-piperazinyl)ethyl]oxy-4H-1-benzopyran-4-one, mesylate salt, mp. 192–194, dec;

Cpd 342 8-Methyl-2-(4-morpholinyl)-7-[2-(4-thiomorpholinyl)ethyl]oxy -4H-1-benzopyran-4-one, mesylate salt, mp. 191–193;

Cpd 343 8-Methyl-2-(4-morpholinyl)-7-[2-(4-thiomorpholinyl)ethyl]oxy-4H-1-benzopyran-4-one, bismesylate salt, mp. 200–202;

Cpd 344 8-methyl-2-(4-morpholinyl)-7-[2-(3-pyridinyloxy)ethoxy]-4H-1-Benzopyran-4-one, bismesylate salt, mp. 175–177; and Cpd 345 (R)-7-[2-[2-(hydroxymethyl)-1-pyrrolidinyl]ethoxy]-8-methyl-2-(4-morpholinyl)-4H-1-Benzopyran-4-one, mesylate salt, mp. 161–162.5.

EXAMPLE 274

(Relating to chart K) Preparation of 8-Hydroxy-2-(4-morpholinylmethylene)-4H-1-benzopyran-4-one 2',3'-Dihydroxy-acetophenone (7.5 g, 49 mmole) is dissolved in 303 ml dry tetrahydrofuran in a flame dried 1,000 ml three neck round bottom flask under nitrogen. The solution is treated rapidly dropwise with potassium t-butoxide (1.0 M/THF) (197 ml, 197 mmole) and is mechanically stirred vigorously as methyl-2-(4-morpholinyl)-acetate (10.2 g, 64 mmole) is added neat. The reaction mixture is heated at reflux for 48 h, is treated with a second lot of methyl-2-(4-morpholinyl)-acetate (7 g, 44 mmole), and is stirred an additional 24h at reflux. The reaction is cooled to room temperature, is diluted with 200 ml water, and the tetrahydrofuran is removed in vacuo. The pH of the aqueous residue is adjusted to 6.8 with 10% hydrochloric acid and the mixture is extracted with 5×100 ml dichloromethane. The combined organics are dried over magnesium sulfate and are concentrated in vacuo to a brown solid. The solid is washed with 200 ml diethyl ether and is dried to afford 8.8 g of a tan solid. The solid is recrystallized twice from ethyl acetate to provide 7.5 g (60%) of the title compound as an off-white solid, mp. 202.5° C.

EXAMPLE 275

Preparation of 8-Benzyloxy-2-(4-morpholinylmethylene)-4H-1-benzopyran-4-one
Cpd 275

8-Hydroxy-2-(4-morpholinylmethylene)-4H-1-benzopyran-4-one (261 mg, 1 mmole) is suspended in 7 ml acetonitrile in a 25 ml one neck round bottom flask under nitrogen. The suspension is treated successively with potassium carbonate (829 mg, 6 mmole) and benzyl bromide (150ul, 1.3 mmole) and the reaction mixture is warmed to 70° C. for 1 h. The mixture is cooled to room temperature and the acetonitrile is removed in vacuo. The residue is washed with 1×25 ml dichloromethane and the insoluble material is removed by filtration. The filtrate is concentrated in vacuo to a yellow oil. The oil is chromatographed over 15 g silica gel (230–400 mesh)eluting with 3% methanol/dichloromethane and collecting 6 ml fractions. Fractions 12–27 are combined and concentrated to afford a colorless oil which is crystallized from diethyl ether to provide 246 mg (70%) of the title compound as a white solid, mp. 107°–107.5° C.

Following the general procedures of examples 203 and 274 there are prepared the following products:

Cpd 264 8-methyl-2-(4-morpholinylmethyl)-7-[[1-(1-phenylethyl)-1H-tetrazol-5-yl]methoxy]-4H-1-Benzopyran-4-one, mp. 145–147;

Cpd 265 8-methyl-2-(4-morpholinylmethyl)-7-[(1-phenyl-1H-tetrazol-5-yl) methoxy]-4H-1-Benzopyran-4-one, mp. 162–163;

Cpd 267 7-[[1-(1,1-dimethylethyl)-1H-tetrazol-5-yl]methoxy]-8-methyl-1-(4-morpholinylmethyl)-4H-1-Benzopyran-4-one, mp. 125–130;

Cpd 270 5-[[[8-methyl-2-(4-morpholinylmethyl)-4-oxo-4H-1-benzopyran-7-yl]oxy]methyl]-α-(phenylmethyl)-1H-Tetrazole-1-acetic acid ethyl ester, mp. 190–194;

Cpd 276 2-(4-morpholinylmethyl)-8-[[3-(trifluoromethyl)pehnyl]methoxy]-4H-1-Benzopyran-4-one, mp. 124.5–125.5;

Cpd 277 8-[2-(4-methyl-1-piperazinyl)ethoxy]-2-(4-morpholinylmethyl)-4H-1-Benzopyran-4-one, mp. 88.5–89.5;

Cpd 278 8-[2-[4-(2-ethoxyphenyl)-1-piperazinyl]ethoxy]-2-(4-morpholinylmethyl)-4H-1-Benzopyran-4-one, mp. 134.5–135.5;

Cpd 308 2-(4-morpholinylmethyl)-8-[[1-(1-phenylethyl)-1H-tetrazol-5-yl]methoxy]-4H-1-Benzopyran-4-one, mp. 105–110;

Cpd 350 8-[(1-cyclopropyl-1H-tetrazol-5-yl)methoxy]-2-(4-morpholinylmethyl)-4H-1-Benzopyran-4-one, mp. 84–87;

Cpd 351 7-[(1-cyclobutyl-1H-tetrazol-5-yl) methoxy]-8-methyl-2-(4-morpholinylmethyl)-4H-1-Benzopyran-4-one, mp. 178–179; and Cpd 352 7-[(1-cyclopropyl-1H-tetrazol-5-yl)methoxy]-8-methyl-2-(4-morpholinylmethyl)-4H-1-Benzopyran-4-one, mp. 146–147.

CHART A

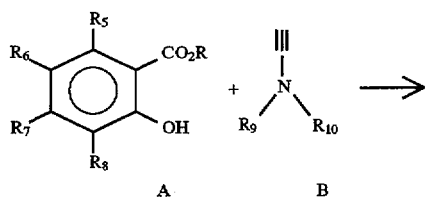

-continued
CHART A
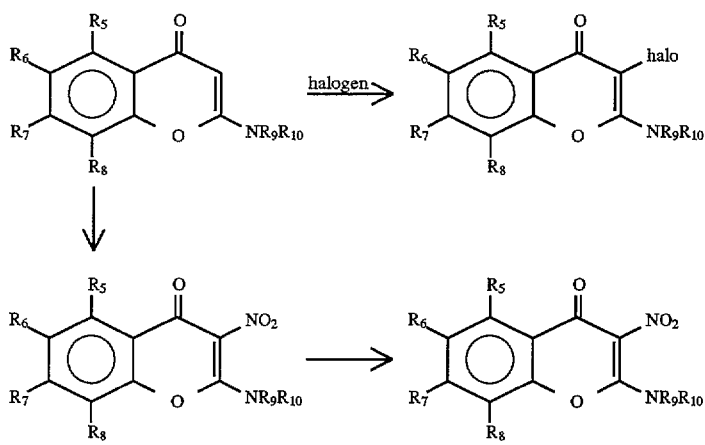
CHART B
CHART C
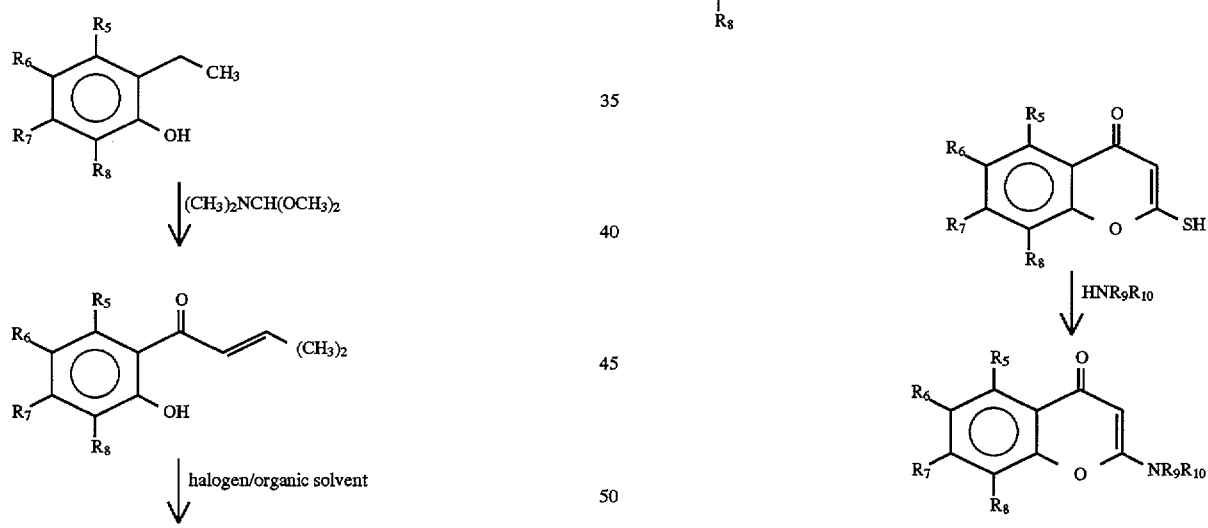
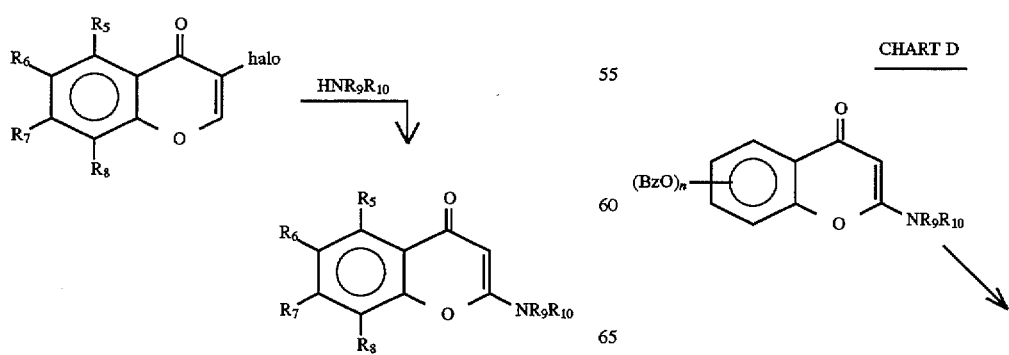
CHART D

-continued
CHART D
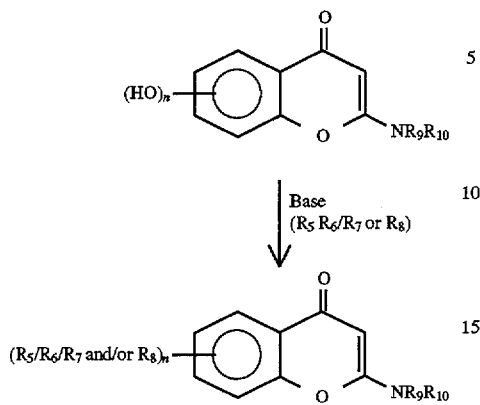
CHART E
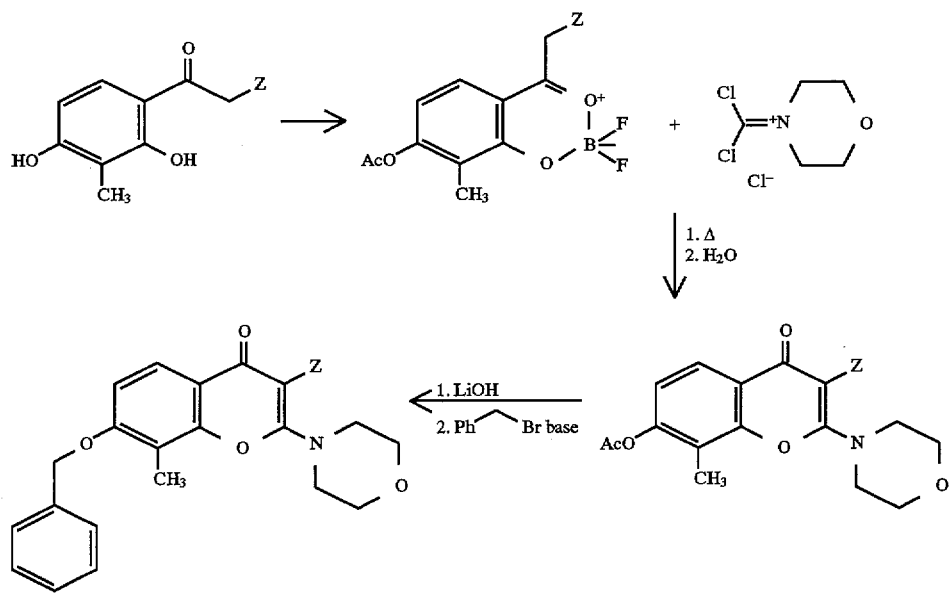
CHART F
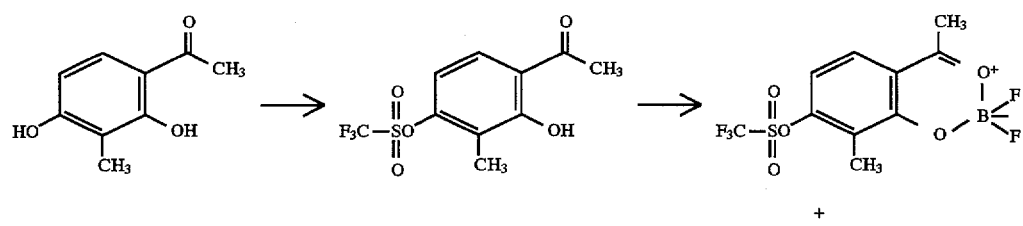

-continued
CHART F
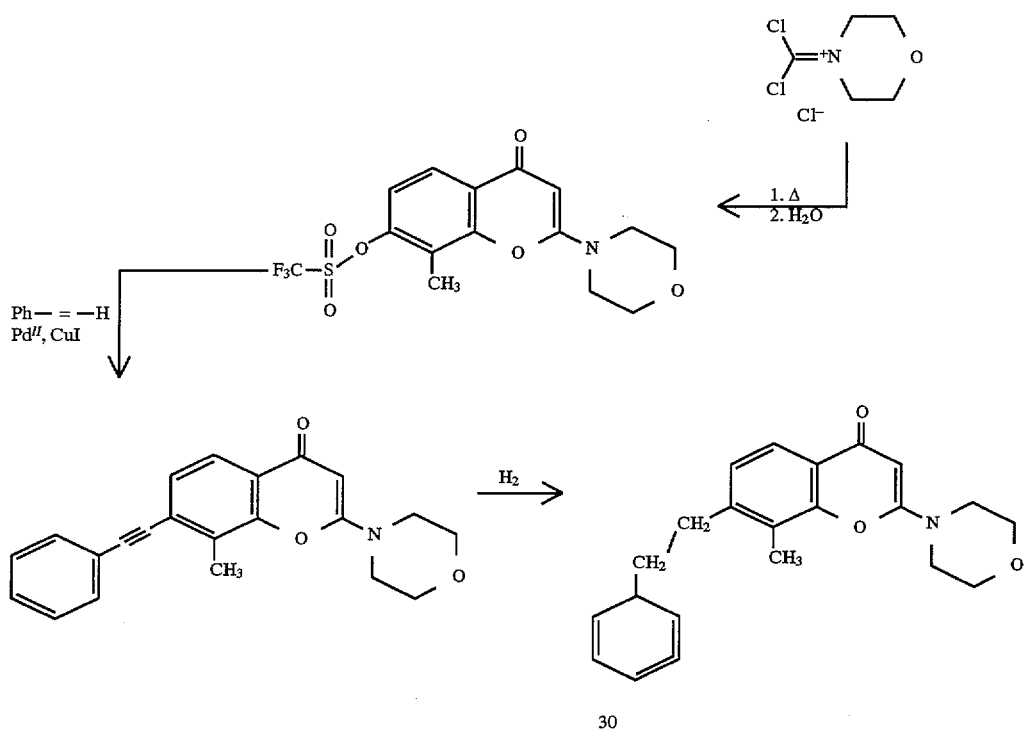
CHART G
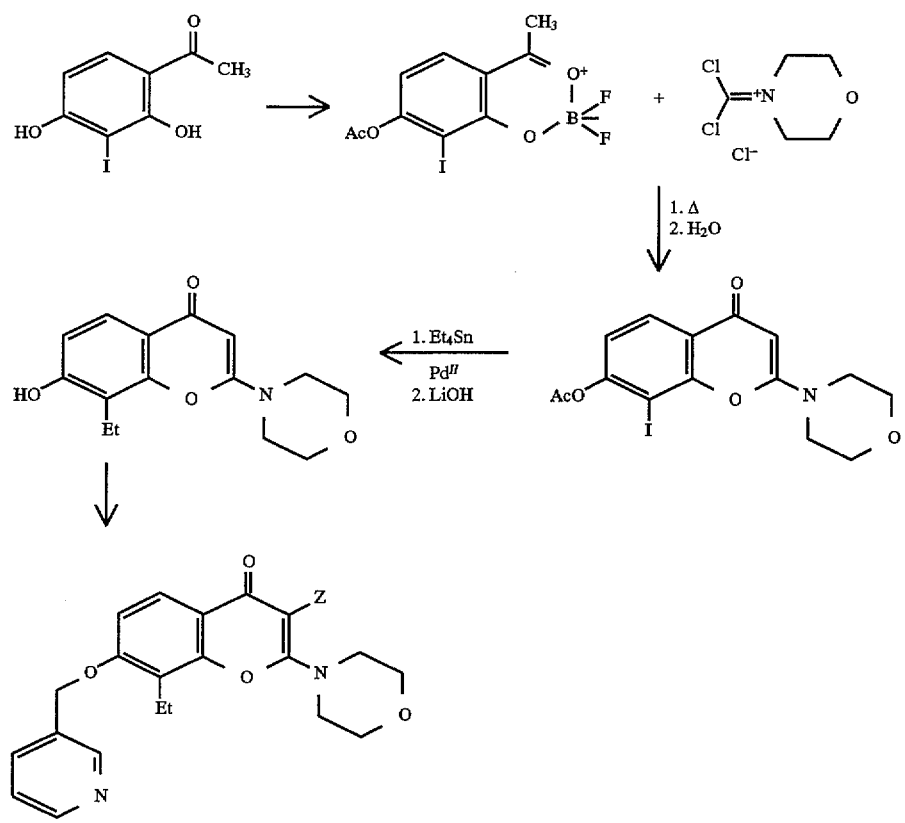

CHART H
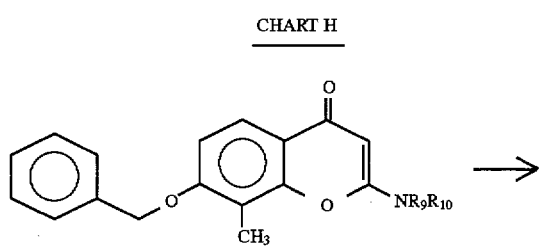
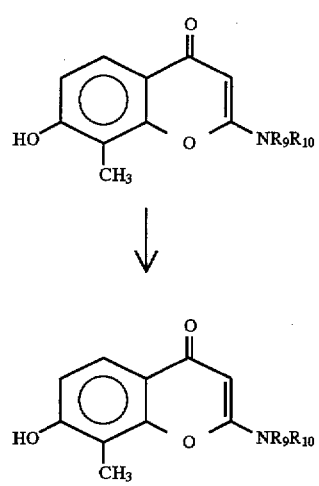
CHART I
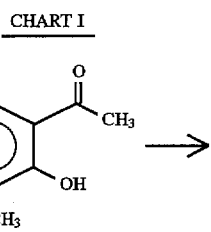
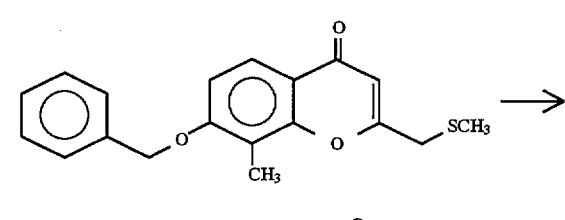
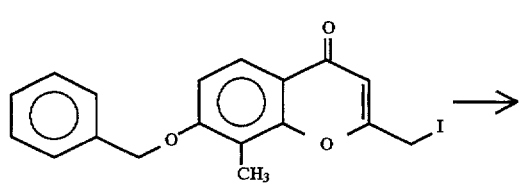
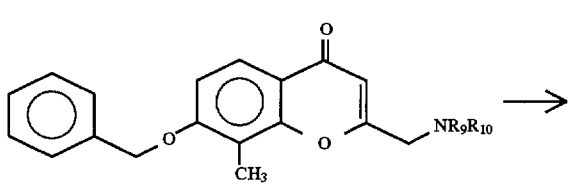
-continued
CHART I
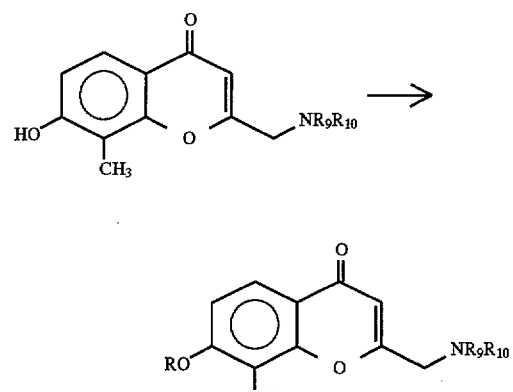
CHART J
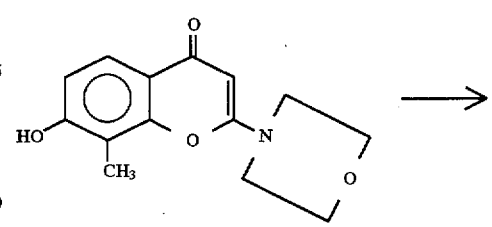
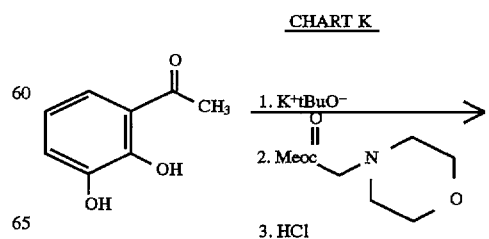
CHART K

CHART K -continued

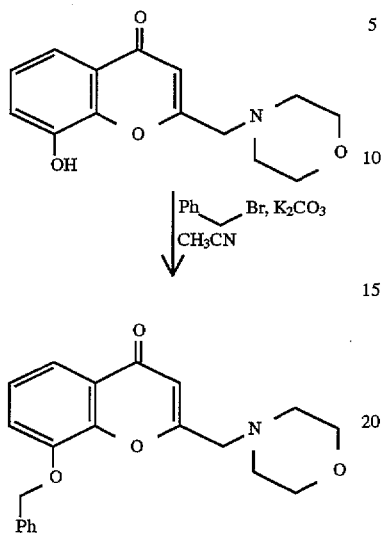

CHART L

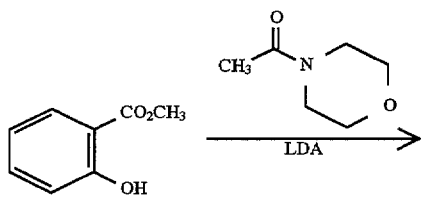

FORMULA

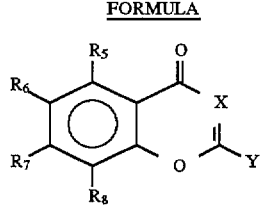

I

FORMULA -continued

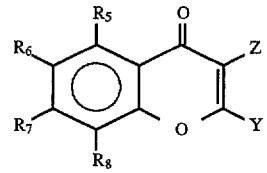

IA

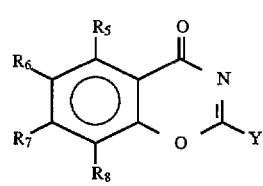

IB

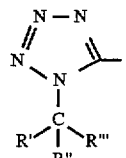

II

We claim:
1. A compound of Formula I

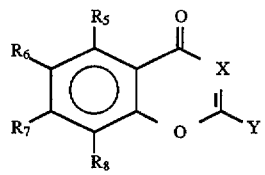

wherein X is CZ where Z is H, $C_1$–$C_5$ alkyl, amino (-$NH_2$) or a halogen atom;

Y is -($CH_2$)$_n$-(4-morpholine) optionally substituted with one or two members selected from the group consisting of $C_1$–$C_4$ alkyl, $C_1$–$C_4$ alkoxy, halo or trifluoromethyl;

$R_5$, $R_6$, $R_7$ and $R_8$, being the same or different, are selected from the group consisting of hydrogen, $C_1$–$C_8$ alkyl, -($CH_2$)$_n$phenyl, -($CH_2$)$_n$naphthyl, -($CH_2$)$_n$pyridinyl, -($CH_2$)$_q$$NR_9R_{10}$, -CH=CH-phenyl, -$CH_2$-CH=$CH_2$, -CH=CH-$CH_3$, -CH=$CH_2$, -O-$CH_2$-CH=$CH_2$, -C≡C-phenyl, -O($CH_2$)$_p$(N-methylpiperdin-3-yl), -O-($CH_2$)$_p$$NR_9R_{10}$, -O-($CH_2$)$_p$-4-($C_1$–$C_4$alkyl)-1-piperazine, -O-($CH_2$)$_p$(1-piperidinyl), -O-($CH_2$)$_p$(1-pyrrolidinyl), -O-($CH_2$)$_2$-4-methyl-1-piperazine, -O-$CH_2CH(OCH_3)_2$, -O-($CH_2$)$_p$$OR_{15}$, -O-($CH_2$)$_p$-O-($CH_2$)$_p$-$OR_{15}$, -O-($CH_2$)$_p$-S-$R_{15}$, -O-($CH_2$)$_p$-O-($CH_2$)$_p$$NR_9R_{10}$, -O-($CH_2$)$_p$-S-($CH_2$)$_p$$NR_9R_{10}$, -O-($CH_2$)$_p$-S-($CH_2$)$_p$-$OR_{15}$, -O-($CH_2$)$_p$-S(O)-$R_{15}$, -O-($CH_2$)$_p$-S($O_2$)-$R_{15}$, -O-($CH_2$)$_p$-S(O)-($CH_2$)$_p$$NR_9R_{10}$, -O-($CH_2$)$_p$-S(O)-($CH_2$)$_p$-$OR_{15}$, -O-($CH_2$)$_p$-S($O_2$)-($CH_2$)$_p$$NR_9R_{10}$, -O-($CH_2$)$_p$-S($O_2$)-($CH_2$)$_p$-$OR_{15}$, -O-($CH_2$)$_p$-[4-[($CH_2$)$_p$$OR_{15}$]-1-piperazine], -O-($CH_2$)$_p$-[4-(CH)(phenyl)$_2$-1-piperazine], -O-($CH_2$)$_p$-[4-($CH_2$)$_q$phenyl-1-piperazine], -O-($CH_2$)$_p$-[4-($CH_2$)$_q$pyridinyl-1-piperazine], -O-($CH_2$)$_p$-[4-($NR_9R_{10}$ substituted pyridinyl)-1-piperazine], -O-($CH_2$)$_p$-(OH substituted 1-piperidine, -O-($CH_2$)$_p$-1-pyrrolidin-2-one, -($CH_2$)$_n$C(O)-($CH_2$)$_n$$R_9$, -($CH_2$)$_n$C(O)O-($CH_2$)$_p$$R_9$, -($CH_2$)$_n$C(O)O-($CH_2$)$_p$$NR_9R_{10}$, -($CH_2$)$_n$C(O)($CH_2$)$_n$$NR_9R_{10}$, $NO_2$, -O-($CH_2$)$_n$C(O)-($CH_2$)$_p$$R_9$, -O-($CH_2$)$_n$C(O)O-($CH_2$)$_p$$R_9$, -O-($CH_2$)$_n$C(O)-($CH_2$)$_n$$NR_9R_{10}$, -$NR_9R_{10}$, -N($R_9$)($CH_2$)$_n$C(O)-($CH_2$)$_n$$R_{10}$, -N($R_9$)-($CH_2$)$_n$C(O)O-($CH_2$)$_n$$R_{10}$, N($R_9$)($CH_2$)$_n$C(O)-($CH_2$)$_n$$NR_9R_{10}$, -O-($CH_2$)$_n$ phenyl, -O-$(CH_2)_n$pyridine, -O$(CH_2)_n$C(O)-$(CH_2)_n$ pyridine, -O-$(CH_2)_n$C(O)O-$(CH_2)_n$pyridine, -O$(CH_2)_n$C(O)-N($R_9$)$(CH_2)_n$pyridine, -O-$(CH_2)_n$quinoxalinyl, -O-$(CH_2)_n$quinolinyl, -O-$(CH_2)_n$pyrazinyl, -O-$(CH_2)_n$naphthyl, -O-$(CH_2)_n$C(O)-$(CH_2)_n$naphthyl, -O-$(CH_2)_n$C(O)O-$(CH_2)_n$naphthyl, -O-$(CH_2)_n$C(O)N$R_9$-$(CH_2)_n$naphthyl, halo (fluoro, chloro, bromo, iodo), OH, -$(CH_2)_q$-OH, -$(CH_2)_q$OC(O)$R_9$, -$(CH_2)_q$OC(O)-N$R_9R_{10}$,-(1-cyclohexyl-1H-tetrazol-5-yl)$C_1$-$C_4$ alkoxy, [1-($C_1$-$C_5$alkyl)-1H-tetrazol-5-yl]-$C_1$-$C_4$ alkoxy, [1-(phenyl)-1H-tetrazol-5-yl]$C_1$-$C_4$ alkoxy, -[1-(pyridinyl)-1H-tetrazol-5-yl]$C_1$-$C_4$ alkoxy, -[1-(1-phenylethyl)-1H-tetrazol-5-yl]$C_1$-$C_4$ alkoxyl, -$C_1$-$C_4$ alkoxyl, a group of Formula II $$\begin{array}{c} N-N \\ \parallel \quad \diagdown \\ N \quad \quad \\ \diagdown \; N \\ \quad | \\ \quad C \\ R'\diagup | \diagdown R''' \\ \quad R'' \end{array}$$

wherein R' is methyl or carboxy, R" is hydrogen and R'" is selected from benzyl, $C_1$-$C_5$ alkyl, -$(CH_2)_n CO_2H$, -$CH_2SH$, -$CH_2SCH_3$, imidazolinylmethylene, indolinylmethylene, $CH_3CH(OH)$, $CH_2OH$, $H_2N(CH_2)_4$-(optionally in protected form) or $H_2NC(NH)NH(CH_2)_3$ (optionally in protected form); with the proviso that when Y is 4-morpholinyl, the compound is other than:

6,7-dimethoxy-2-(4-morpholinyl)-4H-1-benzopyran-4-one, 7,8-(Bis)-(3-trifluoromethyl)phenylmethoxy-2-(4-morpholinyl)-4H-1-benzopyran-4-one, N-cyclohexyl -2-[[8-methyl -2-(4-morpholinyl)-4-oxo-4H-1-benzopyran-7-yl]oxy]-acetamide, 2-[[8-methyl-2-(4-morpholinyl)-4-oxo-4H-1-benzopyran-7-yl]oxy]-N-phenyl-acetamide, 6-[(1-cyclohexyl -1H-tetrazol -5-yl)methoxy]-2-(4-morpholinyl)-4H-1-Benzopyran-4-one, 2-[[8-methyl -2-(4-morpholinyl)-4-oxo-4H-1-benzopyran-7-yl]oxy]-N-(1-phenylethyl)-acetamide;

$R_9$ and $R_{10}$, being the same or different, are selected from the group consisting of (a) hydrogen, with the proviso that $R_9$ and $R_{10}$ are not both hydrogen; (b) $C_1$-$C_{12}$ alkyl; (c) phenyl optionally substituted with one, 2 or 3 $C_1$-$C_4$ alkyl, $C_1$-$C_4$ alkoxy, halo, OH, trifluoromethyl or -$CO_2$($C_1$-$C_4$alkyl); (d)-$(CH_2)_n$phenyl, (e)-$(CH_2)_n$pyridinyl or (f) wherein $R_9$ and $R_{10}$, taken together with N, form a saturated or unsaturated heterocyclic amine ring selected from the group consisting of (aa) 4-morpholine optionally substituted with one or two members selected from the group consisting of $C_1$-$C_4$ alkyl, $C_1$-$C_4$ alkoxy, halo or trifluoromethyl, (bb) 4-thiomorpholine optionally substituted with one or two members selected from the group consisting of $C_1$-$C_4$ alkyl, $C_1$-$C_4$ alkoxy, halo or trifluoromethyl, (cc) 3-amino-1-pyrrolidine, (dd) 1-pyrrolidine optionally substituted with one or two members selected from the group consisting of $C_1$-$C_4$ alkyl, $C_1$-$C_4$ alkoxy, halo, OH, -$CH_2OH$, or trifluoromethyl, (ee) 1-piperidine optionally substituted with one or two members selected from the group consisting of $C_1$-$C_4$ alkyl, $C_1$-$C_4$ alkoxy, halo, trifluoromethyl, -$(CH_2)_q$OH, -$CO_2H$, -$CO_2CH_3$, -$CO_2CH_2CH_3$ or phenyl (wherein phenyl is optionally substituted with one, 2 or 3 $C_1$-$C_4$ alkyl, $C_1$-$C_4$ alkoxy, halo or trifluoromethyl), (ff) 1-piperazine, 4-($C_1$-$C_4$alkyl)-1-piperazine, 4-phenyl-1-piperazine (wherein phenyl is optionally substituted with one, 2 or 3 $C_1$-$C_4$ alkyl, $C_1$-$C_4$ alkoxy, halo or trifluoromethyl) or 4-pyridinyl-1-piperazine optionally substituted with one or two members selected from the group consisting of $C_1$-$C_4$ alkyl, $C_1$-$C_4$ alkoxy, halo, trifluoromethyl, -$CH_2OH$, -$CO_2H$, -$CO_2CH_3$ or -$CO_2CH_2CH_3$, and (gg) thiazolidine, thiazolidine-4-carboxylic acid, pipecolinic acid, p-piperazinacetophenone, 1-homopiperazine, 1-methylhomopiperazine, 4-phenyl-1,2-3,6-tetrahydropyridine, proline, tetrahydrofurylamine, 1-(3-hydroxy)pyrrolidine, nipecotamide, 1,2,3,4-tetrahydroisoquinoline or imidazole;

$R_{15}$ is selected from H, $C_1$-$C_5$ alkyl, -$(CH_2)_n$phenyl, -$(CH_2)_n$pyridin-1-yl, -$(CH_2)_n$pyridin-2-yl, -$(CH_2)_n$pyridin-3-yl, -$(CH_2)_n$pyridin-4-yl, -$(CH_2)_n$-1-($C_1$-$C_4$alkyl)-1H-5-tetrazole, -$(CH_2)_n$-pyrimidine, -$(CH_2)_n$-2-benzoxazole, -$(CH_2)_n$-2-benzothiazole, -$(CH_2)_n$-($C_1$-$C_4$alkyl)-triazole, -$(CH_2)_n$-($C_1$-$C_4$alkyl)-imidazole;

n is 0-5;

p is 2-5;

q is 1-5;

and pharmaceutically acceptable salts and hydrates thereof; and with the overall proviso that when $R_5$, $R_6$ and $R_8$ are selected from: H, $C_1$-$C_8$ alkyl, or halogen and Z is H or $C_1$-$C_5$ alkyl, or halogen, then $R_7$ is other than -OH, -$OCH_3$, -(($CH_2)_n$C(O)O-$(CH_2)_p R_9$ or -O-$(CH_2)_n$C(O)-N$R_9 R_{10}$ wherein n is other than 0, and $R_9$ and $R_{10}$ are selected from H or $C_1$-$C_{12}$ alkyl.

2. A compound according to claim 1 wherein Z is H or $C_1$-$C_5$ alkyl.

3. A compound according to claim 2 wherein Y is -(4-morpholine) or -$CH_2$-(4-morpholine).

4. A compound according to claim 3 wherein Z is H.

5. A compound according to claim 4 wherein Y is -(4-morpholine).

6. A compound according to claim 3 wherein $R_5$, $R_6$, $R_7$ and $R_8$ are selected from the following groups:

(i) $R_5$, $R_6$, $R_7$ and $R_8$ are each hydrogen; or (ii) $R_5$, $R_6$, and $R_8$ are each hydrogen, and $R_7$ is selected from:

-O-$(CH_2)_n$phenyl (wherein phenyl is optionally substituted with one, 2 or 3 $C_1$-$C_4$ alkyl, $C_1$-$C_4$ alkoxy, halo or trifluoromethyl), -C≡C-phenyl (wherein phenyl is optionally substituted with one, 2 or 3 $C_1$-$C_4$ alkyl, $C_1$-$C_4$ alkoxy, halo or trifluoromethyl), or -$(CH_2)_n$phenyl (wherein phenyl is optionally substituted with one, 2 or 3 $C_1$-$C_4$ alkyl, $C_1$-$C_4$ alkoxy, halo or trifluoromethyl); or (iii) $R_5$ and $R_6$ are hydrogen, $R_8$ is hydrogen, halo or $C_1$-$C_5$ alkyl, and $R_7$ is selected from: -O-$(CH_2)_n$phenyl (wherein phenyl is optionally substituted with one, 2 or 3 $C_1$-$C_4$ alkyl, $C_1$-$C_4$ alkoxy, halo or trifluoromethyl), -O-$(CH_2)_n$pyridinyl (wherein pyridinyl is optionally substituted with one, 2 or 3 $C_1$-$C_4$ alkyl, $C_1$-$C_4$ alkoxy, halo or trifluoromethyl), -O-$(CH_2)_n$naphthyl, -$(CH_2)_n$phenyl (wherein phenyl is optionally substituted with one, 2 or 3 $C_1$-$C_4$ alkyl, $C_1$-$C_4$ alkoxy, halo or trifluoromethyl), -$(CH_2)_n$pyridinyl (wherein pyridinyl is optionally substituted with one, 2 or 3 $C_1$-$C_4$ alkyl, $C_1$-$C_4$ alkoxy, halo or trifluoromethyl), -$(CH_2)_p$(1- piperidinyl), -(CH$_2$)$_p$(1-pyrrolidinyl), -O-(CH$_2$)$_p$NR$_9$R$_{10}$,-O-(CH$_2$)$_p$-O-R$_{15}$, -O-(CH$_2$)$_p$-S-R$_{15}$, or -[(1-cyclohexyl-1H-tetrazol-5-yl)C$_1$–C$_4$ alkoxy; or (iv) R$_5$, R$_7$ and R$_8$ are each hydrogen, and R$_6$ is -NH-C(O)-O-CH$_2$phenyl.

7. A compound according to claim 5 wherein R$_5$, R$_6$, R$_7$ and R$_8$ are selected from the following groups:

(i) R$_5$, R$_6$, R$_7$ and R$_8$ are each hydrogen; or (ii) R$_5$, R$_6$, and R$_8$ are each hydrogen, and R$_7$ is selected from:

-O-(CH$_2$)$_n$phenyl (wherein phenyl is optionally substituted with one, 2 or 3 C$_1$–C$_4$ alkyl, C$_1$–C$_4$ alkoxy, halo or trifluoromethyl), -C≡C-phenyl (wherein phenyl is optionally substituted with one, 2 or 3 C$_1$–C$_4$ alkyl, C$_1$–C$_4$ alkoxy, halo or trifluoromethyl), or -(CH$_2$)$_n$phenyl (wherein phenyl is optionally substituted with one, 2 or 3 C$_1$–C$_4$ alkyl, C$_1$–C$_4$ alkoxy, halo or trifluoromethyl); or (iii) R$_5$ and R$_6$ are hydrogen, R$_8$ is hydrogen, halo or C$_1$–C$_5$ alkyl, and R$_7$ is selected from: -O-(CH$_2$)$_n$phenyl (wherein phenyl is optionally substituted with one, 2 or 3 C$_1$–C$_4$ alkyl, C$_1$–C$_4$ alkoxy, halo or trifluoromethyl), -O-(CH$_2$)$_n$pyridinyl (wherein pyridinyl is optionally substituted with one, 2 or 3 C$_1$–C$_4$ alkyl, C$_1$–C$_4$ alkoxy, halo or trifluoromethyl), -O-(CH$_2$)$_n$naphthyl, -(CH$_2$)$_n$phenyl (wherein phenyl is optionally substituted with one, 2 or 3 C$_1$–C$_4$ alkyl, C$_1$–C$_4$ alkoxy, halo or trifluoromethyl), -(CH$_2$)$_p$pyridinyl (wherein pyridinyl is optionally substituted with one, 2 or 3 C$_1$–C$_4$alkyl, C$_1$–C$_4$ alkoxy, halo or trifluoromethyl), -(CH$_2$)$_p$(1-piperidinyl), -(CH$_2$)$_p$(1-pyrrolidinyl),-O-(CH$_2$)$_p$NR$_9$R$_{10}$,-O-(CH$_2$)$_p$-O-R$_{15}$, -O-(CH$_2$)$_p$-S-R$_{15}$, or -[(1-cyclohexyl-1H-tetrazol-5-yl)C$_1$–C$_4$ alkoxy; or (iv) R$_5$, R$_7$ and R$_8$ are each hydrogen, and R$_6$ is -NH-C(O)-O-CH$_2$phenyl; or (v) R$_5$ and R$_6$ are hydrogen, R$_8$ is hydrogen, -CH=CH$_2$, halo or C$_1$–C$_5$ alkyl, and R$_7$ is selected from: -O-(CH$_2$)$_n$ phenyl (wherein phenyl is optionally substituted with one, 2 or 3 C$_1$–C$_4$ alkyl, C$_1$–C$_4$ alkoxy, halo or trifluoromethyl), -O-(CH$_2$)$_n$pyridinyl (wherein pyridinyl is optionally substituted with one, 2 or 3 C$_1$–C$_4$ alkyl, C$_1$–C$_4$ alkoxy, halo or trifluoromethyl), -O-(CH$_2$)$_n$ naphthyl, -(CH$_2$)$_n$phenyl (wherein phenyl is optionally substituted with one, 2 or 3 C$_1$–C$_4$ alkyl, C$_1$–C$_4$ alkoxy, halo or trifluoromethyl), -(CH$_2$)$_p$pyridinyl (wherein pyridinyl is optionally substituted with one, 2 or 3 C$_1$–C$_4$ alkyl, C$_1$–C$_4$ alkoxy, halo or trifluoromethyl), -(CH$_2$)$_p$(1-piperidinyl), -(CH$_2$)$_p$(1-pyrrolidinyl),-O-(CH$_2$)$_p$-4-(C$_1$–C$_4$alkyl)-1-piperazine, -O-(CH$_2$)$_p$(1-piperidinyl), -O-(CH$_2$)$_p$(1-pyrrolidinyl), -O-(CH$_2$)$_p$-O-R$_{15}$, -O-(CH$_2$)$_p$-S-R$_{15}$, -[1-(C$_1$–C$_5$alkyl)-1H-tetrazol-5-yl]-C$_1$–C$_4$ alkoxy, or -[(1-cyclohexyl-1H-tetrazol-5-yl)C$_1$–C$_4$ alkoxy; or (vi) R$_5$, R$_6$ and R$_7$ are hydrogen, and R$_8$ is selected from: -C≡C-phenyl (wherein phenyl is optionally substituted with one, 2 or 3 C$_1$–C$_4$ alkyl, C$_1$–C$_4$ alkoxy, halo or trifluoromethyl), -O-(CH$_2$)$_n$phenyl (wherein phenyl is optionally substituted with one, 2 or 3 C$_1$–C$_4$ alkyl, C$_1$–C$_4$ alkoxy, halo or trifluoromethyl), -O-(CH$_2$)$_n$ pyridinyl (wherein pyridinyl is optionally substituted with one, 2 or 3 C$_1$–C$_4$ alkyl, C$_1$–C$_4$ alkoxy, halo or trifluoromethyl), -O-(CH$_2$)$_n$naphthyl, -(CH$_2$)$_n$phenyl (wherein phenyl is optionally substituted with one, 2 or 3 C$_1$–C$_4$ alkyl, C$_1$–C$_4$ alkoxy, halo or trifluoromethyl), -(CH$_2$)$_p$pyridinyl (wherein pyridinyl is optionally substituted with one, 2 or 3 C$_1$–C$_4$ alkyl, C$_1$–C$_4$ alkoxy, halo or trifluoromethyl), -(CH$_2$)$_p$(1-piperidinyl), -(CH$_2$)$_p$(1-pyrrolidinyl), -O-(CH$_2$)$_p$-4-(C$_1$–C$_4$alkyl)-1-piperazine, -O-(CH$_2$)$_p$(1-piperidinyl), -O-(CH$_2$)$_p$(1-pyrrolidinyl), -O-(CH$_2$)$_p$-O-R$_{15}$, -O-(CH$_2$)$_p$-S-R$_{15}$, -]1-C$_1$–C$_5$alkyl)-1H-tetrazol-5-yl)]-C$_1$–C$_4$ alkoxy, or -[(1-cyclohexyl-1H-tetrazol-5-yl)C$_1$–C$_4$ alkoxy.

8. A compound according to claim 1 selected from the group consisting of:

Cpd 1 6-Chloro-2-(4-morpholinyl)-4H-1-benzopyran-4-one;

Cpd 2 2-(4-morpholinyl)-4H-benzopyran-4-one;

Cpd 3 8-Methyl-2-(4-morpholinyl)-(7-phenylmethoxy)-4H-benzopyran-4-one;

Cpd 4 7-Chloro-2-(4-morpholinyl)-4H-1-benzopyran-4-one;

Cpd 5 8-Chloro-2-(4-morpholinyl)-4H-1-benzopyran-4-one;

Cpd 6 6-Bromo-2-(4-morpholinyl)-4H-1-benzopyran-4-one;

Cpd 7 6-Fluoro-2-(4-morpholinyl)-4H-1-benzopyran-4-one;

Cpd 8 6-Methyl-2-(4-morpholinyl)-4H-1-benzopyran-4-one;

Cpd 9 7-Methyl-2-(4-morpholinyl)-4H-1-benzopyran-4-one;

Cpd 10 8-Methyl-2-(4-morpholinyl)-4H-1-benzopyran-4-one;

Cpd 11 6-Methoxy-2-(4-morpholinyl)-4H-1-benzopyran-4-one;

Cpd 12 7-Methoxy-2-(4-morpholinyl)-4H-1-benzopyran-4-one;

Cpd 13 6-(Phenylmethoxy)-2-(4-morpholinyl)-4H-1-benzopyran-4-one;

Cpd 14 8-(Phenylmethoxy)-2-(4-morpholinyl)-4H-1-benzopyran-4-one;

Cpd 15 [2-(4-morpholinyl)-4-oxo-4H-1-benzopyran-6-yl]-1,1-dimethylethyl carbamic acid ester;

Cpd 16 6-(3-pyridinecarboxamide)-2-(4-morpholinyl)-4H-1-benzopyran-4-one;

Cpd 17 2-(4-Morpholinyl)-6-nitro-4H-1-benzopyran-4-one;

Cpd 19 6-([[Phenylmethoxy]carbonyl]amino)-2-(4-morpholinyl)-4H-1-benzopyran-4-one;

Cpd 20 8-Methoxy-2-(4-morpholinyl)-4H-1-benzopyran-4-one;

Cpd 21 3-Amino-2-(4-morpholinyl)-4H-1-benzopyran-4-one;

Cpd 22 3-Chloro-2-(4-morpholinyl)-4H-1-benzopyran-4-one;

Cpd 23 3-Bromo-2-(4-morpholinyl)-4H-1-benzopyran-4-one;

Cpd 24 8-Methyl-2-(4-morpholinyl)-7-(phenylmethoxy)-4H-1-benzopyran-4-one;

Cpd 25 2-(4-Morpholinyl)-5-(phenylmethoxy)-4H-1-benzopyran-4-one;

Cpd 26 7,8-Dimethoxy-2-(4-morpholinyl)-4H-1-benzopyran-4-one;

Cpd 39 7-Hydroxy-8-methyl-2-(4-morpholinyl)-4H-1-benzopyran-4-one;

Cpd 40 6-Hydroxy-2-(4-morpholinyl)-4H-1-benzopyran-4-one;

Cpd 41 7-Hydroxy-2-(4-morpholinyl)-4H-1-benzopyran-4-one;

Cpd 42 5-Hydroxy-2-(4-morpholinyl)-4H-1-benzopyran-4-one;

Cpd 43 8-Hydroxy-2-(4-morpholinyl)-4H-1-benzopyran-4-one;

Cpd 44 7-Methoxy-8-methyl-2-(4-morpholinyl)-4H-1-benzopyran-4-one;

Cpd 47 7-[(4-Methoxyphenyl)methoxy]-8-methyl-2-(4-morpholinyl)-4H-1-benzopyran-4-one;

Cpd 48 8-Methyl-7-[(4-methylphenyl)methoxy]-2-(4-morpholinyl)-4H-1-benzopyran-4-one;

Cpd 49 7-[(4-Chlorophenyl)methoxy]-8-methyl-2-(4-morpholinyl)-4H-1-benzopyran-4-one;

Cpd 50 7-[(3,4-Dichlorophenyl)methoxy]-8-methyl-2-(4-morpholinyl)-4H-1-benzopyran-4-one;

Cpd 51 8-Methyl-2-(4-morpholinyl)-7-(2-pyridinylmethoxy)-4H-1-benzopyran-4-one;

Cpd 52 8-Methyl-7-[[(phenyl)carbonyl]oxy]-2-(4-morpholinyl)-4H-1-benzopyran-4-one;

Cpd 53 7-Methoxy-8-methyl-2-(4-morpholinyl)-4H-1-benzopyran-4-one;

Cpd 54 7-[[4-(1,1-Dimethylethyl)phenyl]methoxy]-8-methyl-2-(4-morpholinyl)-4H-1-benzopyran-4-one;

Cpd 55 8-Methyl-2-(4-morpholinyl)-7-[[4-phenylmethoxy)-phenyl]methoxy]-4H-1-benzopyran-4-one;

Cpd 56 7-[(3-Methoxyphenyl)methoxy]-8-methyl-2-(4-morpholinyl)-4H-1-benzopyran-4-one;

Cpd 57 7-[(4-Nitrophenyl)methoxy]-8-methyl-2-(4-morpholinyl)-4H-1-benzopyran-4-one;

Cpd 58 7-[(2-Phenylethyl)methoxy]-8-methyl-2-(4-morpholinyl)-4H-1-benzopyran-4-one;

Cpd 59 7-[(2-Methoxyphenyl)methoxy]-8-methyl-2-(4-morpholinyl)-4H-1-benzopyran-4-one;

Cpd 60 7-[(4-Ethoxyphenyl)methoxy]-8-methyl-2-(4-morpholinyl)-4H-1-benzopyran-4-one;

Cpd 61 8-(4-Ethoxy-benzyloxy)-2-(4-morpholinyl)-4H-1-benzopyran-4-one;

Cpd 62 2-(4-Morpholinyl)-8-(4-nitro-benzyloxy)-4H-1-benzopyran-4-one;

Cpd 63 8-(2-Methoxy-benzyloxy)-2-(4-morpholinyl)-4H-1-benzopyran-4-one;

Cpd 64 2-(4-Morpholinyl)-8-(2-phenyl-ethoxy)-4H-1-benzopyran-4-one;

Cpd 66 8-(4-Benzyloxy-benzyloxy)-2-(4-morpholinyl)-4H-1-benzopyran-4-one;

Cpd 67 8-(4-Chloro-benzyloxy)-2-(4-morpholinyl)-4H-1-benzopyran-4-one;

Cpd 68 8-(4-t-Butyl-benzyloxy)-2-(4-morpholinyl)-4H-1-benzopyran-4-one;

Cpd 69 8-(3-Methoxy-benzyloxy)-2-(4-morpholinyl)-4H-1-benzopyran-4-one;

Cpd 70 8-(3,4-Dichloro-benzyloxy)-2-(4-morpholinyl)-4H-1-benzopyran-4-one;

Cpd 71 8-(4-Methyl-benzyloxy)-2-(4-morpholinyl)-4H-1-benzopyran-4-one;

Cpd 72 8-(4-Methoxy-benzyloxy)-2-(4-morpholinyl)-4H-1-benzopyran-4-one;

Cpd 73 2-(4-Morpholinyl)-8-(naphthyl-2-methyloxy)-4H-1-benzopyran-4-one;

Cpd 74 2-(4-Morpholinyl)-8-(naphthyl-1-methyloxy)-4H-1-benzopyran-4-one;

Cpd 75 8-Methyl-2-(4-morpholinyl)-7-(naphthyl-2-methyloxy)-4H-1-benzopyran-4-one;

Cpd 76 8-Methyl-2-(4-morpholinyl)-7-(naphthyl-1-methyloxy)-4H-1-benzopyran-4-one;

Cpd 101 2-(4-morpholinyl)-7-(phenylmethoxy)-4H-1-benzopyran-4-one;

Cpd 102 8-Methyl-2-(4-morpholinyl)-7-(2-oxo-2-phenylethoxy)-4H-1-benzopyran-4-one;

Cpd 103 6-Chloro-8-methyl-2-(4-morpholinyl)-7-phenylmethoxy)-4H-1-benzopyran-4-one;

Cpd 104 [[2-(4-Morpholinyl)-4-oxo-4H-1-benzopyran-8-yl]oxy]-acetic acid methyl ester;

Cpd 105 4-[[[8-Methyl-2-(4-morpholinyl)-4-oxo-4H-1-benzopyran-7-yl]oxy]methyl]-benzoic acid methyl ester;

Cpd 106 4-[[[2-(4-Morpholinyl)-4-oxo-4H-1-benzopyran-8-yl]oxy]methyl]-benzoic acid methyl ester;

Cpd 107 8-Methyl-2-(4-morpholinyl)-7-[[3-(trifluoromethyl)phenyl]methoxy]-4H-1-benzopyran-4-one;

Cpd 108 2-(4-Morpholinyl)-8-[[3-(trifluoromethyl)phenyl]methoxy]-4H-1-benzopyran-4-one;

Cpd 109 7-(Cyclohexylmethoxy)-8-methyl-2-(4-morpholinyl)-4H-1-benzopyran-4-one;

Cpd 110 8-Methyl-2-(4-morpholinyl)-7-(2-propenyloxy)-4H-1-benzopyran-4-one;

Cpd 111 2-(4-Morpholinyl)-7-(1-naphthalenylmethoxy)-4H-1-benzopyran-4-one;

Cpd 112 8-Methyl-2-(4-morpholinyl)-7-(3-pyrindinylmethoxy)-4H-1-benzopyran-4-one;

Cpd 113 8-Methyl-2-(4-morpholinyl)-7-(4-pyrindinylmethoxy)-4H-1-benzopyran-4-one;

Cpd 115 8-methyl-2-(4-morpholinyl)-7-(2-quinoxalinylmethoxy)-4H-1-benzopyran-4-one;

Cpd 116 8-methyl-2-(4-morpholinyl)-7-(pyrazinlymethoxy)-4H-1-benzopyran-4-one;

Cpd 117 8-methyl-2-(4-morpholinyl)-7-(2-pyridinylmethoxy)-4H-1-benzopyran-4-one N-oxide;

Cpd 118 8-methyl-2-(4-morpholinyl)-7-(3-pyridinylmethoxy)-4H-1-benzopyran-4-one N-oxide;

Cpd 119 8-Iodo-2-(4-morpholinyl)-7-(3-pyrindinylmethoxy)-4H-1-benzopyran-4-one;

Cpd 120 3,3-Dimethyl-1-[[8-methyl-2-(4-morpholinyl)-4-oxo-4H-1-benzopyran-7-yl]oxy]-butan-2-one;

Cpd 121 1-[[8-Methyl-2-(4-morpholinyl)-4-oxo-4H-1-benzopyran-7-yl]oxy]-propan-2-one;

Cpd 122 1-[[8-Methyl-2-(4-morpholinyl)-4-oxo-4H-1-benzopyran-7-yl]oxy]-butan-2-one;

Cpd 123 8-Methyl-2-(4-morpholinyl)-7-(2-oxo-2-(2-naphthyl)ethoxy)-4H-1-benzopyran-4-one;

Cpd 125 2-(4-Morpholinyl)-7-(2-pyrindinylmethoxy)-4H-1-benzopyran-4-one;

Cpd 126 2-(4-Morpholinyl)-7-(3-pyrindinylmethoxy)-4H-1-benzopyran-4-one;

Cpd 127 2-(4-Morpholinyl)-8-(2-pyrindinylmethoxy)-4H-1-benzopyran-4-one;

Cpd 128 2-(4-Morpholinyl)-8-(3-pyrindinylmethoxy)-4H-1-benzopyran-4-one;

Cpd 129 8-methyl-2-(4-morpholinyl)-7-(2-quinolinylmethoxy)-4H-1-benzopyran-4-one;

Cpd 130 7,8-(Bis)-phenylmethoxy-2-(4-morpholinyl)-4H-1-benzopyran-4-one;

Cpd 131 7,8-(Bis)-acetyloxy-2-(4-morpholinyl)-4H-1-benzopyran-4-one;

Cpd 132 7,8-(Bis)-hydroxy-2-(4-morpholinyl)-4H-1-benzopyran-4-one;

Cpd 133 7-Hydroxy-2-(4-morpholinyl)-8-phenylmethoxy-4H-1-benzopyran-4-one;

Cpd 135 8-Hydroxy-2-(4-morpholinyl)-7-(3-trifluoromethyl)phenylmethoxy-4H-1-benzopyran-4-one;

Cpd 136 7-Hydroxy-2-(4-morpholinyl)-8-(3-trifluoromethyl)phenylmethoxy-4H-1-benzopyran-4-one;

Cpd 137 7-[3-(1-cyclohexyl-1H-tetrazol-5-yl)propoxyl-8-methyl-2-(4-morpholinyl)-4H-1-benzopyran-4-one;

Cpd 138 8-[3-(1-cyclohexyl-1H-tetrazol-5-yl)propoxy]-2-(4-morpholinyl)-4H-1-benzopyran-4-one;

Cpd 139 7-[(1-cyclohexyl-1H-tetrazol-5-yl)methoxy]-8-methyl-2-(4-morpholinyl)-4H-1-benzopyran-4-one;

Cpd 140 8-[(1-cyclohexyl-1H-tetrazol-5-yl)methoxy]-2-(4-morpholinyl)-4H-1-benzopyran-4-one;

Cpd 141 2-(4-morpholinyl)-8-[(1-phenyl-1H-tetrazol-5-yl)oxy]-4H-1-benzopyran-4-one;

Cpd 142 N-cyclohexyl-2-[[2-(4-morpholinyl)-4-oxo-4H-1-benzopyran-8-yl]oxy]-acetamide;

Cpd 143 N-(1,1-dimethylethyl)-2-[[2-(4-morpholinyl)-4-oxo-4H-1-benzopyran-8-yl]oxy]-acetamide;

Cpd 144 2-[[2-(4-morpholinyl)-4-oxo-4H-1-benzopyran-8-yl]-N-phenyl-acetamide;

Cpd 145 2-[[2-(4-morpholinyl)-4-oxo-4H-1-benzopyran-8-yl]oxy]-N-(1-phenylethyl)-acetamide;

Cpd 147 N-[[[8-methyl-2-(4-morpholinyl)-4-oxo-4H-1-benzopyran-7-yl]oxy]acetyl]-phenyalanine, ethyl ester;

Cpd 149 8-methyl-2-(4-morpholinyl)-7-[(1-phenyl-1H-tetrazol-5-yl)oxy]-4H-1-Benzopyran-4-one;

Cpd 152 2-[[8-methyl-2-(4-morpholinyl)-4-oxo-4H-1-benzopyran-7-yl]oxy]-N-3-pyridinyl-acetamide;

Cpd 153 N-[[[8-methyl-2-(4-morpholinyl)-4-oxo-4H-1-benzopyran-7-yl]oxy]acetyl]-Phenylalanine;

Cpd 154 7-(2,2-dimethoxyethoxy)-8-methyl-2-(4-morpholinyl)-4H-1-Benzopyran-4-one;

Cpd 155 2-(4-Morpholinyl)-8-(2-propenyl)-4H-1-benzopyran-4-one;

Cpd 156 2-(4-Morpholinyl)-8-(1-propenyl)-4H-1-benzopyran-4-one;

Cpd 157 8-Formyl-2-(4-Morpholinyl)-4H-1-benzopyran-4-one;

Cpd 158 2-(4-morpholinyl)-8-(phenylamino)methyl-4H-1-benzopyran-4-one;

Cpd 159 2-(4-morpholinyl)-8-(2E-phenyl)ethenyl-4H-1-benzopyran-4-one;

Cpd 160 8-Hydroxymethyl-2-(4-Morpholinyl)-4H-1-benzopyran-4-one;

Cpd 162 8-methyl-7-[(1-methyl-3-piperidinyl)methoxy]-2-(4-morpholinyl)-4H-1-Benzopyran-4-one;

Cpd 163 8-Methyl-2-(4-morpholinyl)-7-(2-(1-piperidinyl)ethyl)oxy-4H-1-benzopyran-4-one;

Cpd 164 8-Methyl-2-(4-morpholinyl)-7-(2-(1-pyrrolidinyl)ethyl)oxy-4H-1-benzopyran-4-one;

Cpd 165 8-Methyl-2-(4-morpholinyl)-7-(2-(4-morpholinyl)ethyl)oxy-4H-1-benzopyran-4-one;

Cpd 166 8-Methyl-2-(4-morpholinyl)-7-(3-(1-piperidino)propyl)oxy-4H-1-benzopyran-4-one;

Cpd 167 7-(2-Diethylaminoethyl)oxy-8-methyl-2-(4-morpholinyl)-4H-1-benzopyran-4-one;

Cpd 168 7-[2-(ethylphenylamino)ethoxy]-8-methyl-2-(4-morpholinyl)-4H-1-Benzopyran-4-one;

Cpd 169 7-(2-Diisopropylaminoethyl)oxy-8-methyl-2-(4-morpholinyl)-4H-1-benzopyran-4-one;

Cpd 172 7-(2-(4-Benzyl-(1-piperizinyl))ethyl)oxy-8-methyl-2-(4-morpholinyl)-4H-1-benzopyran-4-one;

Cpd 173 7-Acetoxy-3,8-dimethyl-2-(4-morpholinyl)-4H-1-benzopyran-4-one;

Cpd 174 3,8-dimethyl-7-hydroxy-2-(4-morpholinyl)-4H-1-benzopyran-4-one;

Cpd 175 7-benzyloxy-3,8-dimethyl-2-(4-morpholinyl)-4H-1-benzopyran-4-one;

Cpd 176 3,8-Dimethyl-2-(4-morpholinyl)-7-(naphthyl-1-methyloxy)-4H-1-benzopyran-4-one;

Cpd 177 3,8-Dimethyl-7-(4-methoxy-benzyloxy)-2-(4-morpholinyl)-4H-1-benzopyran-4-one;

Cpd 178 3,8-Dimethyl-2-(4-morpholinyl)-7-(2-phenylethyloxy)-4H-1-benzopyran-4-one;

Cpd 179 3,8-Dimethyl-7-(4-chlorobenzyloxy)-2-(4-morpholinyl)-4H-1-benzopyran-4-one;

Cpd 180 3,8-Dimethyl-2-(4-morpholinyl)-7-(3-trifluoromethyl-benzyloxy)-4H-1-benzopyran-4-one;

Cpd 181 7-(Carbomethoxy-methoxyl)-3,8-dimethyl-2-(4-morpholinyl)-4H-1-benzopyran-4-one;

Cpd 182 8-Hydroxy-3-methyl-2-(4-morpholinyl)-4H-1-benzopyran-4-one;

Cpd 183 8-Benzyloxy-3-methyl-2-(4-morpholinyl)-4H-1-benzopyran-4-one;

Cpd 184 3-methyl-2-(4-morpholinyl)-8-(m-trifluoromethyl-benzyloxy)-4H-1-benzopyran-4-one;

Cpd 185 8-methyl-7-(2-phenyl)ethynyl-2-(4-morpholinyl)-4H-1-benzopyran-4-one;

Cpd 186 8-methyl-2-(4-morpholinyl)-7-(2-phenyl)ethyl-4H-1-benzopyran-4-one;

Cpd 187 2-(4-Morpholinyl)-8-(2-phenyl)ethynyl-4H-1-benzopyran-4-one;

Cpd 188 2-(4-Morpholinyl)-8-(2-phenyl)ethyl-4H-1-benzopyran-4-one;

Cpd 189 2-(4-Morpholinyl)-8-(2-(3-trifluoromethyl)phenyl)ethynyl-4H-1-benzopyran-4-one;

Cpd 190 2-(4-Morpholinyl)-8-(2-(3-trifluoromethyl)phenyl)ethyl-4H-1-benzopyran-4-one;

Cpd 192 8-Methyl-2-(4-morpholinyl)-7-(2-(1-naphthyl))ethyl-4H-1-benzopyran-4-one;

Cpd 193 8-Methyl-2-(4-morpholinyl)-7-phenyl-4H-1-benzopyran-4-one;

Cpd 194 7-acetyloxy-8-iodo-2-(4-morpholinyl)-4H-1-benzopyran-4-one;

Cpd 195 8-ethyl-2-(4-morpholinyl)-7-(3-pyrindinylmethoxy)-4H-1-benzopyran-4-one;

Cpd 196 8-Ethyl-2-(4-morpholinyl)-7-phenylmethoxy-4H-1-benzopyran-4-one;

Cpd 197 8-Iodo-2-(4-morpholinyl)-7-phenylmethoxy-4H-1-benzopyran-4-one;

Cpd 198 8-Ethyl-2-(4-morpholinyl)-7-(2-(1-piperidinyl)ethyl)oxy-4H-1-benzopyran-4-one;

Cpd 199 8-Iodo-2-(4-morpholinyl)-7-(3-pyrindinylmethoxy)-4H-1-benzopyran-4-one;

Cpd 200 8-Iodo-7-hydroxy-2-(4-morpholinyl)-4H-1-benzopyran-4-one;

Cpd 204 8-Methyl-2-(4-morpholinylmethyl)-7-(phenylmethoxy)-4H-1-benzopyran-4-one;

Cpd 205 7-hydroxy-2-(4-morpholinylmethyl)-8-methyl-4H-1-benzopyran-4-one;

Cpd 206 7-[(1-cyclohexyl-1H-tetrazol-5-yl)methyoxy]-8-methyl-2-(4-morpholinylmethyl)-4H-1-benzopyran-4-one;

Cpd 207 8-Methyl-2-(4-morpholinylmethyl)-7-(3-pyridinylmethoxy)-4H-1-benzopyran-4-one;

Cpd 208 7-[2-(4-Methyl-1-piperazinyl)ethyl]oxy-8-methyl-2-(4-morpholinyl)-4H-1-benzopyran-4-one;

Cpd 209 7-(2-(2-Hydroxymethylpiperidin-1-yl)ethyl)oxy-8-methyl-2-(4-morpholinyl)-4H-1-benzopyran-4-one;

Cpd 210 7-(2-(3-Hydroxymethylpiperidin-1-yl)ethyl)oxy-8-methyl-2-(4-morpholinyl)-4H-1-benzopyran-4-one;

Cpd 211 7-(2-(2-Carboethoxypiperidin-1-yl)ethyl)oxy-8-methyl-2-(4-morpholinyl)-4H-1-benzopyran-4-one;

Cpd 212 7-(2-(3-Carboethoxypiperidin-1-yl)ethyl)oxy-8-methyl-2-(4-morpholinyl)-4H-1-benzopyran-4-one;

Cpd 213 8-Methyl-7-(2-(2-methylpiperidin-1-yl)ethyl)oxy-2-(4-morpholinyl)-4H-1-benzopyran-4-one;

Cpd 214 7-(2-(3-Carboxypiperidin-1-yl)ethyl)oxy-8-methyl-2-(4-morpholinyl)-4H-1-benzopyran-4-one;

Cpd 215 8-Methyl-2-(4-morpholinyl)-7-[2-(1-piperazinyl)ethyl]oxy-4H-1-benzopyran-4-one;

Cpd 216 8-Methyl-7-[(2-methoxy)ethyl]oxy-2-(4-morpholinyl)-4H-1-benzopyran-4-one;

Cpd 217 2-(4-Morpholinyl)-7-phenylmethoxy-8-vinyl-4H-1-benzopyran-4-one;

Cpd 218 2-(4-Morpholinyl)-8-phenyl-7-phenylmethoxy-4H-1-benzopyran-4-one;

Cpd 219 8-Methyl-7-[(2-thiomethyl)ethyl]oxy-2-(4-Morpholinyl)-4H-1-benzopyran-4-one;

Cpd 220 8-Methyl-2-(4-morpholinyl)-7-[2-(4-(2-hydroxy)ethyl-1-piperazinyl)ethyl]oxy-4H-1-benzopyran-4-one;

Cpd 222 7-[2-(Hydroxy)ethyl]oxy-8-methyl-2-(4-morpholinyl)-4H-1-benzopyran-4-one;

Cpd 223 8-Methyl-2-(4-morpholinyl)-7-[2-(2-thiopyrindinyl)ethyl]oxy-4H-1-benzopyran-4-one;

Cpd 225 7-[2-(4-(2-Ethoxyphenyl)-1-piperazinyl)ethyl]oxy-8-methyl-2-(4-morpholinyl)-4H-1-benzopyran-4-one;

Cpd 226 8-Methyl-7-[2-((1-Methyl-1,3-imidazol-2-yl)thio)ethyl]oxy-2-(4-morpholinyl)-4H-1-benzopyran-4-one;

Cpd 227 7-[2-((Bis-N,N'-(2-methoxy)ethoxy)amino)ethyl]oxy-8-methyl-2-(4-morpholinyl)-4H-1-benzopyran-4-one;

Cpd 228 8-Methyl-7-[2-((4-Methyl-1,2,4-triazol-3-yl)thio)ethyl]oxy-2-(4-morpholinyl)-4H-1-benzopyran-4-one;

Cpd 229 7-[2-(N-Ethyl-N'-((2-hydroxy)ethyl)amino)ethyl]oxy-8-methyl-2-(4-morpholinyl)-4H-1-benzopyran-4-one;

Cpd 230 8-Methyl-7-[2-((1-Methyl-5-tetrazoyl)thio)ethyl]oxy-2-(4-morpholinyl)-4H-1-benzopyran-4-one;

Cpd 231 8-Methyl-2-(4-morpholinyl)-7-[2-((2-pyrimidinyl)thio)ethyl]oxy-4H-1-benzopyran-4-one;

Cpd 232 8-Methyl-2-(4-morpholinyl)-7-[2-(4-(2-pyridinyl)-1-piperazinyl)-ethyl]oxy-4H-1-benzopyran-4-one;

Cpd 233 8-Methyl-2-(4-morpholinyl)-7-[2-(4-thiomorpholinyl)ethyl]oxy-4H-1-benzopyran-4-one;

Cpd 234 7-[2-((2-(Bis-N,N'-diethylamino)ethyl)-thio)ethyl]oxy-8-Methyl-2-(4-morpholinyl)-4H-1-benzopyran-4-one;

Cpd 235 8-Methyl-7-[2-((2-benzoxazolyl)thio)ethyl]oxy-2-(4-morpholinyl)-4H-1-benzopyran-4-one;

Cpd 236 8-Methyl-7-[2-((2-benzothiazolyl)thio)ethyl]oxy-2-(4-morpholinyl)-4H-1-benzopyran-4-one;

Cpd 237 7-[2-(4-(3-Ethylamino-pyridin-2-yl)-1-piperazinyl)ethyl]oxy-8-methyl-2-(4-morpholinyl)-4H-1-benzopyran-4-one; and Cpd 238 8-Methyl-2-(4-morpholinyl)-7-[2-(pyrrolidinone-1-yl)ethyl]oxy-4H-1-benzopyran-4-one;

or a pharmaceutically acceptable salt or hydrate thereof.

9. A compound according to claim 1 selected from the group consisting of:

Cpd 2 2-(4-morpholinyl)-4H-benzopyran-4-one;

Cpd 3 8-Methyl-2-(4-morpholinyl)-(7-phenylmethoxy)-4H-benzopyran-4-one;

Cpd 19 6-([[Phenylmethoxy]carbonyl]amino)-2-(4-morpholinyl)-4H-1-benzopyran-4-one;

Cpd 51 8-Methyl-2-(4-morpholinyl)-7-(2-pyridinylmethoxy)-4H-1-benzopyran-4-one;

Cpd 72 8-(4-Methoxy-benzyloxy)-2-(4-morpholinyl)-4H-1-benzopyran-4-one;

Cpd 76 8-Methyl-2-(4-morpholinyl)-7-(naphthyl-1-methyloxy)-4H-1-benzopyran-4-one;

Cpd 112 8-Methyl-2-(4-morpholinyl)-7-(3-pyrindinylmethoxy)-4H-1-benzopyran-4-one;

Cpd 139 7-[(1-cyclohexyl-1H-tetrazol-5-yl)methoxy]-8-methyl-2-(4-morpholinyl)-4H-1-benzopyran-4-one;

Cpd 163 8-Methyl-2-(4-morpholinyl)-7-(2-(1-piperidinyl)ethyl)oxy-4H-1-benzopyran-4-one;

Cpd 164 8-Methyl-2-(4-morpholinyl)-7-(2-(1-pyrrolidinyl)ethyl)oxy-4H-1-benzopyran-4-one;

Cpd 171 8-Methyl-2-(1-piperidinyl)-7-(3-pyrindinylmethoxy)-4H-1-benzopyran-4-one;

Cpd 204 8-Methyl-2-(4-morpholinylmethyl)-7-(phenylmethoxy)-4H-1-benzopyran-4-one;

Cpd 208 7-[2-(4-Methyl-1-piperazinyl)ethyl]oxy-8-methyl-2-(4-morpholinyl)-4H-1-benzopyran-4-one;

or a pharmaceutically acceptable salt or hydrate thereof.

10. A compound according to claim 1 selected from the group consisting of:

Cpd 242 2-(4-morpholinyl)-8-[2-(2-pyridinylthio)-ethoxy]-4H-1-Benzopyran-4-one;

Cpd 244 8-[2-[4-[3-(ethylamino)-2-pyridinyl]-1-piperazinyl]ethoxy]-2-(4-morpholinyl)-4H-1-Benzopyran-4-one;

Cpd 246 8-methyl-2-(4-morpholinyl)-7-[2-(phenylsulfinyl)ethoxy]-4H-1-Benzopyran-4-one;

Cpd 253 7-[2-[(2-methoxyphenyl)thio]ethoxy]-8-methyl-2-(4-morpholinyl)-4H-1-Benzopyran-4-one;

Cpd 296 2-(4-morpholinyl)-8-[2-[4-(phenylmethyl)-1-piperazinyl]ethoxy]-4H-1-Benzopyran-4-one;

Cpd 326 8-ethenyl-7-[2-(4-methyl-1-piperazinyl)ethoxy]-2-(4-morpholinyl)-4H-1-Benzopyran-4-one;

Cpd 327 8-ethenyl-2-(4-morpholinyl)-7-[2-(1-piperidinyl)ethoxy]-4H-1-Benzopyran-4-one;

Cpd 329 8-ethenyl-2-(4-morpholinyl)-7-[2-(1-pyrrolidinyl)ethoxy]-4H-1-Benzopyran-4-one;

Cpd 330 8-ethenyl-2-(4-morpholinyl)-7-[2-(4-thiomorpholinyl)ethoxy]-4H-1-Benzopyran-4-one;

Cpd 331 (R)-8-ethenyl-7-[2-[2-(hydroxymethyl)-1-pyrrolidinyl]ethoxy]-2-(4-morpholinyl)-4H-1-Benzopyran-4-one;

Cpd 333 7-[2-(2-methoxyethoxy)ethoxy]-8-methyl-2-(4-morpholinyl)-4H-1-Benzopyran-4-one; and Cpd 335 8-methyl-2-(4-morpholinyl)-7-[2-(phenylthio)ethoxy]-4H-1-Benzopyran-4-one;

or a pharmaceutically acceptable salt or hydrate thereof.

11. A compound selected from the group consisting of:

Cpd 243 8-[2-[4-(2-ethoxyphenyl)-1-piperazinyl]ethoxy]-2-(4-morpholinyl)-4H-1-Benzopyran-4-one;

Cpd 245 2-(4-morpholinyl)-8-[2-(1-piperidinyl)ethoxy]-4H-1-Benzopyran-4-one;

Cpd 247 7-[2-[bis(2-pyridinylmethyl)amino]ethoxy]-8-methyl-2-(4-morpholinyl)-4H-1-Benzopyran-4-one;

Cpd 248 (S)-7-[2-[2-(hydroxymethyl)-1-pyrrolidinyl]ethoxy]-8-methyl-2-(4-morpholinyl)-4H-1-Benzopyran-4-one;

Cpd 249 7-[2-[bis[(4-methoxyphenyl)methyl]amino]ethoxy]-8-methyl-2-(4-morpholinyl)-4H-1-Benzopyran-4-one;

Cpd 250 8-methyl-2-(4-morpholinyl)-7-[2-(3-thiazolindinyl)ethoxy]-4H-1-Benzopyran-4-one;

Cpd 251 N-cyclohexyl-N-methyl-2-[[2-(4-morpholinyl)-4-oxo-4H-1-benzopyran-6-yl]oxy]-Acetamide;

Cpd 252 2-(4-morpholinyl)-6-(1-naphthalenylmethoxy)-4H-1-Benzopyran-4-one;

Cpd 255 7-[2-(hexahydro-1H-azepin-1-yl)ethoxy]-8-methyl-2-(4-morpholinyl)-4H-1-Benzopyran-4-one;

Cpd 256 8-methyl-2-(4-morpholinyl)-7-[2-(4-phenyl-1-piperazinyl)ethoxy]-4H-1-Benzopyran-4-one;

Cpd 257 8-methyl-2-(4-morpholinyl)-7-[2-(4-phenyl-1-piperidinyl)ethoxy]-4H-1-Benzopyran-4-one;

Cpd 258 (R)-7-[2-[2-(hydroxymethyl)-1-pyrrolidinyl]ethoxy]-8-methyl-2-(4-morpholinyl)-4H-1-Benzopyran-4-one;

Cpd 259 7-[2-(3-hydroxy-1-pyrrolidinyl)ethoxy]-8-methyl-2-(4-morpholinyl)-4H-1-Benzopyran-4-one;

Cpd 260 7-[2-[4-(2-chlorophenyl)-1-piperazinyl]ethoxy]-8-methyl-2-(4-morpholinyl)-4H-1-Benzopyran-4-one;

Cpd 261 2-(4-morpholinyl)-8-[2-(4-phenyl-1-piperidinyl)ethoxy]-4H-1-Benzopyran-4-one;

Cpd 262 8-methyl-2-(4-morpholinyl)-7-[(1-phenyl-1H-tetrazol-5-yl)methoxy]-4H-1-Benzopyran-4-one;

Cpd 263 5-[[[8-methyl-2-(4-morpholinyl)-4-oxo-4H-1-benzopyran-7-yl]oxy]methyl]-α-(phenylmethyl)-1H-Tetrazole-1-acetic acid ethyl ester;

Cpd 264 8-methyl-2-(4-morpholinylmethyl)-7-[[1-(1-phenylethyl)-1H-tetrazol-5-yl]methoxy]-4H-1-Benzopyran-4-one;

Cpd 265 8-methyl-2-(4-morpholinylmethyl)-7-[(1-phenyl-1H-tetrazol-5-yl)methoxy]-4H-1-Benzopyran-4-one;

Cpd 266 7-[[1-(1,1-dimethylethyl)-1H-tetrazol-5-yl]methoxy]-8-methyl-2-(4-morpholinyl)-4H-1-Benzopyran-4-one;

Cpd 268 8-methyl-7-[2-[methyl [2-(2-pyridinyl)ethyl]amino]ethoxy]-2-(4-morpholinyl)-4H-1-Benzopyran-4-one;

Cpd 269 8-methyl-2-(4-morpholinyl)-7-[2-(2-pyridinyloxy)ethoxy]-4H-1-Benzopyran-4-one;

Cpd 270 5-[[[8-methyl-2-(4-morpholinylmethyl)-4-oxo-4H-1-benzopyran-7-yl]oxy]methyl]-α-(phenylmethyl)-1H-Tetrazole-1-acetic acid ethyl ester;

Cpd 272 6-chloro-8-methyl-7-[2-(4-methyl-1-piperazinyl)ethoxy]-2-(4-morpholinyl)-4H-1-Benzopyran-4-one;

Cpd 273 8-butyl-2-(4-morpholinyl)-7-(phenylmethoxy)-4H-1-Benzopyran-4-one;

Cpd 274 8-Hydroxy-2-(4-morpholinylmethylene)-4H-1-benzopyran-4-one;

Cpd 275 8-Benzyloxy-2-(4-morpholinylmethylene)-4H-1-benzopyran-4-one;

Cpd 276 2-(4-morpholinylmethyl)-8-[[3-(trifluoromethyl)pehnyl]methoxy]-4H-1-Benzopyran-4-one;

Cpd 277 8-[2-(4-methyl-1-piperazinyl)ethoxy]-2-(4-morpholinylmethyl)-4H-1-Benzopyran-4-one;

Cpd 278 8-[2-[4-(2-ethoxyphenyl)-1-piperazinyl]ethoxy]-2-(4-morpholinylmethyl)-4H-1-Benzopyran-4-one;

Cpd 279 8-ethyl-2-(4-morpholinyl)-7-[2-(1-pyrrolidinyl)ethoxy]-4H-1-Benzopyran-4-one;

Cpd 280 8-ethyl-2-(4-morpholinyl)-7-[2-(4-phenyl-1-piperidinyl)ethoxy]-4H-1-Benzopyran-4-one;

Cpd 281 (R)-8-ethyl-7-[2-[2-(hydroxymethyl)-1-pyrrolidinyl]ethoxy]-2-(4-morpholinyl)-4H-1-Benzopyran-4-one;

Cpd 282 8-ethyl-2-(4-morpholinyl)-7-[2-(4-thiomorpholinyl)ethoxy]-4H-1-Benzopyran-4-one;

Cpd 283 8-ethyl-7-[2-(4-methyl-1-piperazinyl)ethoxy]-2-(4-morpholinyl)-4H-1-Benzopyran-4-one;

Cpd 285 7-[2-(3,4-dihydro-2(1H)-isoquinolinyl)ethoxy]-8-methyl-2-(4-morpholinyl)-4H-1-Benzopyran-4-one;

Cpd 286 7-(acetyloxy)-2-(4-morpholinyl)-8-(2-propenyl)-4H-1-Benzopyran-4-one;

Cpd 287 7-(acetyloxy)-2-(4-morpholinyl)-8-propyl-4H-1-Benzopyran-4-one;

Cpd 288 7-hydroxy-2-(4-morpholinyl)-8-propyl-4H-1-Benzopyran-4-one;

Cpd 289 7-[2-(4-methyl -1-piperazinyl)ethoxy]-2-(4-morpholinyl)-8-propyl-4H-1-Benzopyran-4-one;

Cpd 290 2-(4-morpholinyl)-8-propyl-7-[2-(1-pyrrolindinyl)ethoxy]-4H-1-Benzopyran-4-one;

Cpd 291 2-(4-morpholinyl)-7-[2-(1-piperidinyl)ethoxy]-8-propyl-4H-1-Benzopyran-4-one;

Cpd 292 2-(4-morpholinyl)-7-[2-(4-phenyl-1-piperidinyl)ethoxy]-8-propyl-4H-1-Benzopyran-4-one;

Cpd 293 2-(4-morpholinyl)-8-propyl-7-[2-(4-thiomorpholinyl)ethoxy]-4H-1-Benzopyran-4-one;

Cpd 294 (R)-7-[2-[2-(hydroxymethyl)-1-pyrrolidinyl]ethoxy]-2-(4-morpholinyl)-8-propyl-4H-1-Benzopyran-4-one;

Cpd 295 8-[2-(3,4-dihydro-2(1H)-isoquinolinyl)ethoxy]-2-(4-morpholinyl)-4H-1-Benzopyran-4-one;

Cpd 298 7-(acetyloxy)-6-bromo-8-methyl-2-(4-morpholinyl)-4H-1-Benzopyran-4-one;

Cpd 299 7-(acetyloxy)-6,8-dimethyl-2-(4-morpholinyl)-4H-1-Benzopyran-4-one;

Cpd 300 7-hydroxy-6,8-dimethyl-2-(4-morpholinyl)-4H-1-Benzopyran-4-one;

Cpd 301 7-(acetyloxy)-6-iodo-8-methyl-2-(4-morpholinyl)-4H-1-Benzopyran-4-one;

Cpd 302 7-hydroxy-6-iodo-8-methyl-2-(4-morpholinyl)-4H-1-Benzopyran-4-one;

Cpd 303 6-bromo-7-hydroxy-8-methyl-2-(4-morpholinyl)-4H-1-Benzopyran-4-one;

Cpd 304 8-[2-(ethylphenylamino)ethoxyl]-2-(4-morpholinyl)-4H-1-Benzopyran-4-one;

Cpd 305 2-(4-morpholinyl)-8-(2-quinolinylmethoxy)-4H-1-Benzopyran-4-one;

Cpd 306 1-[2-[[2-(4-morpholinyl)-4-oxo-4H-1-benzopyran-8-yl]oxy]ethyl]-3-Piperidinecarboxylic acid ethyl ester;

Cpd 307 1-[2-[[2-(4-morpholinyl)-4-oxo-4H-1-benzopyran-8-yl]oxy]ethyl]-2-Piperidinecarboxylic acid ethyl ester;

Cpd 308 2-(4-morpholinyllmethyl)-8-[[1-(1-phenylethyl)-1H-tetrazol-5-yl]methoxy]-4H-1-Benzopyran-4-one;

Cpd 309 6,8-dimethyl-7-[2-(4-methyl-1-piperazinyl)-ethoxy]-2-(4-morpholinyl)-4H-1-Benzopyran-4-one;

Cpd 310 6,8-dimethyl-2-(4-morpholinyl)-7-[2-(1-piperidinyl)ethoxy]-4H-1-Benzopyran-4-one;

Cpd 311 6,8-dimethyl-2-(4-morpholinyl)-7-[2-(1-pyrrolindinyl)ethoxy]-4H-1-Benzopyran-4-one;

Cpd 312 2-(4-morpholinyl)-8-(2-propenyloxy)-4H-1-Benzopyran-4-one;

Cpd 314 6-iodo-8-methyl-2-(4-morpholinyl)-7-[2-(1-pyrrolidinyl)ethoxy]-4H-1-Benzopyran-4-one;

Cpd 315 6-iodo-8-methyl-2-(4-morpholinyl)-7-[2-(1-piperidinyl)ethoxy]-4H-1-Benzopyran-4-one;

Cpd 316 6-iodo-8-methyl-7-[2-(4-methyl-1-piperazinyl)-ethoxy]-2-(4-morpholinyl)-4H-1-Benzopyran-4-one;

Cpd 317 6-bromo-8-methyl-2-(4-morpholinyl)-7-[2-(1-pyrrolidinyl)ethoxy]-4H-1-Benzopyran-4-one;

Cpd 318 6-bromo-8-methyl-2-(4-morpholinyl)-7-[2-(1-piperidinyl)ethoxy]-4H-1-Benzopyran-4-one;

Cpd 319 6-bromo-8-methyl-7-[2-(4-methyl-1-piperazinyl)-ethoxy]-2-(4-morpholinyl)-4H-1-Benzopyran-4-one;

Cpd 320 7-[2-(4-methyl-1-piperazinyl)ethoxy]-2-2(4-morpholinyl)-8-(2-propenyl)-4H-1-Benzopyran-4-one;

Cpd 321 2-(4-morpholinyl)-8-(2-propenyl)-7-[2-(1-pyrrolidinyl)ethoxy]-4H-1-Benzopyran-4-one;

Cpd 322 2-(4-morpholinyl)-7-[2-(1-piperidinyl)ethoxy]-8-(2-propenyl)-4H-1-Benzopyran-4-one;

Cpd 323 2-(4-morpholinyl)-7-[2-(4-phenyl-1-piperidinyl)ethoxy]-8-(2-propenyl)-4H-1-Benzopyran-4-one;

Cpd 324 2-(4-morpholinyl)-8-(2-propenyl)-7-[2-(4-thiomorpholinyl)ethoxy]-4H-1-Benzopyran-4-one;

Cpd 325 (R)-7-[2-[-(hydroxymethoxy)-1-pyrrolidinyl]-ethoxy]-2-(4-morpholinyl)-8-(2-propenyl)-4H-1-Benzopyran-4-one;

Cpd 332 2-(4-morpholinyl)-8-[2-(4-thiomorophlinyl)-ethoxy]-4H-1-Benzopyran-4-one;

Cpd 334 8-methyl-2-(4-morpholinyl)-7-(2-phenoxyethoxy)-4H-1-Benzopyran-4-one;

Cpd 348 7-[(1-cyclopropyl-1H-tetrazol-5-yl) methoxy]-8-methyl-2-4-morpholinyl)-4H-1-Benzopyran-4-one;

Cpd 349 7-[(1-cyclobutyl-1H-tetrazol-5-yl) methoxy]-8-methyl-2-(4-morpholinyl)-4H-1-Benzopyran-4-one;

Cpd 350 8-[(1-cyclopropyl-1H-tetrazol-5-yl) methoxy]-2-(4-morpholinylmethyl)-4H-1-Benzopyran-4-one;

Cpd 351 7-[(1-cyclobutyl-1H-tetrazol-5-yl) methoxy]-8-methyl-2-(4-morpholinylmethyl)-4H-1-Benzopyran-4-one;

Cpd 352 7-[(1-cyclopropyl-1H-tetrazol-5-yl) methoxy]-8-methyl-2-(4-morpholinylmethyl)-4H-1-Benzopyran-4-one;

or a pharmaceutically acceptable salt or hydrate thereof.

12. A compound according to claim 1, namely 2-(4-morpholinyl)-4H-1-Benzopyran-4-one.

* * * * *